US011407995B1

(12) United States Patent
Pyzocha et al.

(10) Patent No.: US 11,407,995 B1
(45) Date of Patent: Aug. 9, 2022

(54) RNA-GUIDED NUCLEASES AND DNA BINDING PROTEINS

(71) Applicant: Inari Agriculture Technology, Inc., Cambridge, MA (US)

(72) Inventors: Neena Kenton Pyzocha, New Boston, MA (US); Adam Patrick Joyce, Stow, MA (US); Karl Kremling, Cambridge, MA (US)

(73) Assignee: INARI AGRICULTURE TECHNOLOGY, INC., Cambridge, MA (US)

( * ) Notice: Subject to any disclaimer, the term of this patent is extended or adjusted under 35 U.S.C. 154(b) by 459 days.

(21) Appl. No.: 16/662,867

(22) Filed: Oct. 24, 2019

Related U.S. Application Data

(60) Provisional application No. 62/893,941, filed on Aug. 30, 2019, provisional application No. 62/751,379, filed on Oct. 26, 2018.

(51) Int. Cl.
*C12N 15/11* (2006.01)
*C12N 9/22* (2006.01)
*C12N 15/82* (2006.01)

(52) U.S. Cl.
CPC ............ *C12N 15/11* (2013.01); *C12N 9/22* (2013.01); *C12N 15/8213* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 8,697,359 B1 | 4/2014 | Zhang | |
| 8,771,945 B1 | 7/2014 | Zhang | |
| 8,795,965 B2 | 8/2014 | Zhang | |
| 8,865,406 B2 | 10/2014 | Zhang et al. | |
| 8,871,445 B2 | 10/2014 | Cong et al. | |
| 8,889,356 B2 | 11/2014 | Zhang | |
| 8,889,418 B2 | 11/2014 | Zhang et al. | |
| 8,895,308 B1 | 11/2014 | Zhang et al. | |
| 8,906,616 B2 | 12/2014 | Zhang et al. | |
| 9,790,490 B2 | 10/2017 | Zhang et al. | |
| 9,896,696 B2 | 2/2018 | Begemann et al. | |
| 10,316,324 B2 * | 6/2019 | Begemann | C12N 15/8213 |
| 2003/0220334 A1 | 11/2003 | Wender et al. | |
| 2014/0068797 A1 | 3/2014 | Doudna et al. | |
| 2014/0170753 A1 | 6/2014 | Zhang | |
| 2014/0179006 A1 | 6/2014 | Zhang | |
| 2014/0179770 A1 | 6/2014 | Zhang et al. | |
| 2014/0186843 A1 | 7/2014 | Zhang et al. | |
| 2014/0186919 A1 | 7/2014 | Zhang et al. | |
| 2014/0186958 A1 | 7/2014 | Zhang et al. | |
| 2014/0189896 A1 | 7/2014 | Zhang et al. | |
| 2014/0227787 A1 | 8/2014 | Zhang | |
| 2014/0234972 A1 | 8/2014 | Zhang | |
| 2014/0242664 A1 | 8/2014 | Zhang et al. | |
| 2014/0242699 A1 | 8/2014 | Zhang | |
| 2014/0242700 A1 | 8/2014 | Zhang et al. | |
| 2014/0242702 A1 | 8/2014 | Chen et al. | |
| 2014/0248702 A1 | 9/2014 | Zhang et al. | |
| 2014/0256046 A1 | 9/2014 | Zhang et al. | |
| 2014/0273037 A1 | 9/2014 | Wu | |
| 2014/0273226 A1 | 9/2014 | Wu | |
| 2014/0273230 A1 | 9/2014 | Chen et al. | |
| 2014/0273231 A1 | 9/2014 | Zhang et al. | |
| 2014/0273232 A1 | 9/2014 | Zhang et al. | |
| 2014/0273233 A1 | 9/2014 | Chen et al. | |
| 2014/0273234 A1 | 9/2014 | Zhang et al. | |
| 2014/0273235 A1 | 9/2014 | Voytas et al. | |
| 2014/0287938 A1 | 9/2014 | Zhang et al. | |
| 2014/0295556 A1 | 10/2014 | Joung et al. | |
| 2014/0295557 A1 | 10/2014 | Joung et al. | |
| 2014/0298547 A1 | 10/2014 | Sastry-Dent et al. | |
| 2014/0304853 A1 | 10/2014 | Ainley et al. | |
| 2014/0309487 A1 | 10/2014 | Lee et al. | |
| 2014/0310828 A1 | 10/2014 | Lee et al. | |
| 2014/0310830 A1 | 10/2014 | Zhang et al. | |

(Continued)

FOREIGN PATENT DOCUMENTS

| | | | |
|---|---|---|---|
| WO | 2010075303 A1 | 7/2010 | |
| WO | 2012068627 A1 | 5/2012 | |

(Continued)

OTHER PUBLICATIONS

Aguilera et al., "Systemic in vivo Distribution of Activatable Cell Penetrating Peptides is Superior to Cell Penetrating Peptides", Integrative Biology, Jun. 2009, pp. 371-381, vol. 1, No. 5-6, Howard Hughes Medical Institute.

Balboa et al., "Conditionally Stabilized dCas9 Activator for Controlling Gene Expression in Human Cell Reprogramming and Differentiation", Stem Cell Reports, Sep. 8, 2015, pp. 448-459, vol. 5, The Authors.

Chaikind et al., "A Programmable Cas9-Serine Recombinase Fusion Protein that Operates on DNA Sequences in Mammalian Cells", Nucleic Acids Research, 2016, pp. 9758-9770, vol. 44, No. 20, Oxford University Press.

Choudhury et al., "CRISPR-dCas9 Mediated TET1 Targeting for Selective DNA Demethylation at BRCA1 Promoter", Oncotarget, Jun. 23, 2016, pp. 46545-46556, vol. 7, No. 29.

(Continued)

*Primary Examiner* — Suzanne M Noakes
*Assistant Examiner* — Jae W Lee
(74) *Attorney, Agent, or Firm* — McKee, Voorhees & Sease, PLC

(57) ABSTRACT

Compositions and methods related to Cas proteins, nucleic acids encoding the Cas proteins, and modified host cells comprising the Cas proteins and/or encoding nucleic acids are disclosed. Cas proteins are useful in a variety of applications. Cas proteins bind guide RNAs that in turn provide functional specificity to the Cas proteins, nucleic acids encoding the Cas guide RNAs, and modified host cells comprising the Cas guide RNAs and/or encoding nucleic acids. The Cas polypeptides and corresponding guide RNAs can be used in a variety of applications.

20 Claims, 3 Drawing Sheets

Specification includes a Sequence Listing.

(56) References Cited

U.S. PATENT DOCUMENTS

| | | |
|---|---|---|
| 2014/0315985 A1 | 10/2014 | May et al. |
| 2014/0335063 A1 | 11/2014 | Cannon et al. |
| 2014/0335620 A1 | 11/2014 | Zhang et al. |
| 2014/0342456 A1 | 11/2014 | Mali et al. |
| 2014/0342457 A1 | 11/2014 | Mali et al. |
| 2014/0342458 A1 | 11/2014 | Mali et al. |
| 2014/0349400 A1 | 11/2014 | Jakimo et al. |
| 2014/0349405 A1 | 11/2014 | Sontheimer et al. |
| 2014/0356867 A1 | 12/2014 | Peter et al. |
| 2014/0356956 A1 | 12/2014 | Church et al. |
| 2014/0356958 A1 | 12/2014 | Mali et al. |
| 2014/0356959 A1 | 12/2014 | Church et al. |
| 2014/0357523 A1 | 12/2014 | Zeiner et al. |
| 2014/0357530 A1 | 12/2014 | Zhang et al. |
| 2014/0364333 A1 | 12/2014 | Wu et al. |
| 2014/0377868 A1 | 12/2014 | Joung et al. |
| 2015/0082478 A1 | 3/2015 | Cigan et al. |
| 2018/0282713 A1 | 10/2018 | Van Der Oost |
| 2019/0241954 A1 | 8/2019 | Doudna et al. |

FOREIGN PATENT DOCUMENTS

| | | |
|---|---|---|
| WO | 2013155555 A1 | 10/2013 |
| WO | 2017/064546 A1 | 4/2017 |

OTHER PUBLICATIONS

Du et al., "An Introduction to CRISPR Technology for Genome Activation and Repression in Mammalian Cells", Cold Spring Harbor Protocols, 2016, 4 pages, doi: 10.1101/pdb.top086835.

Gilbert et al., "CRISPR-Mediated Modular RNA-Guided Regulation of Transcription in Eukaryotes", Cell, Jul. 18, 2013, pp. 442-451, vol. 154, No. 2, Elsevier Inc.

Hara et al., "Generation of Mutant Mice Via the CRISPR/Cas9 System Using FokI-dCas9", Scientific Reports, Jun. 9, 2015, pp. 1-9.

Hilton et al., "Epigenome Editing by a CRISPR/Cas9-based Acetyltransferase Activates Genes from Promoters and Enhancers", Nature Biotechnology, May 2015, pp. 510-517, vol. 33, No. 5.

Komor et al., "Programmable Editing of a Target Base in Genomic DNA Without Double-Stranded DNA Cleavage", Nature, 2016, pp. 420-424, vol. 533.

Mendenhall et al., "Locus-Specific Editing of Histone Modifications at Endogenous Enhancers Using Programmable TALE-LSD1 Fusions", Nature Biotechnology, Dec. 2013, pp. 1133-1136, vol. 31, No. 12.

Pham et al., "Post-Transcriptional Gene Regulation: Transcriptional Regulation with CRISPR/Cas9 Effectors in Mammalian Cells", Methods in Molecular Biology, 2016, pp. 43-57, vol. 1358, Edited by Erik Dassi.

Piatek et al., "RNA-Guided Transcriptional Regulation in planta Via Synthetic dCas9-Based Transcription Factors", Plant Biotechnology Journal, 2015, pp. 578-589, vol. 13, Society for Experimental Biology, Association of Applied Biologists and John Wiley & Sons Ltd.

Rivenbark et al., "Epigenetic Reprogramming of Cancer Cells Via Targeted DNA Methylation", Epigenetics, Apr. 2012, pp. 350-360, vol. 7, No. 4, Landes Bioscience.

Sanjana et al., "A Transcription Activator-Like Effector (TALE) Toolbox for Genome Engineering", Nature Protocols, 2012, pp. 171-192, vol. 7, No. 1.

Vojta et al., "Repurposing the CRISPR-Cas9 System for Targeted DNA Methylation", Nucleic Acids Research, 2016, pp. 5615-5628, vol. 44, No. 12, Oxford University Press.

Xu et al., "A CRISPR-Based Approach for Targeted DNA Demethylation", Cell Discovery, 2016, pp. 1-12, vol. 2.

* cited by examiner

SEQ ID NO: 1

MQQYQVSKTVRFGLTLKNSEKKHATHLLLKDLVNVSEERIKNEITKDDKNQSELSFFNE
VIETLDLMDKYIKDWENCFYRTDQIQLTKEYYKVIAKKACFDWFWTNDRGMKFPTSSII
SFNSLKSSDKSKTSDNLDRKKKILDYWKGNIFKTQKAIKDVLDITEDIQKAIEEKKSHREI
NRVNHRKMGIHLIHLINDTLVPLCNGSIFFGNISKLDFCESENEKLIDFASTEKQDERKFL
LSKINEIKQYFEDNGGNVPFARATLNRHTANQKPDRYNEEIKKLVNELGVNSLVRSLKS
KTIEEIKTHFEFENKNKINELKNSFVLSIVEKIQLFKYKTIPASVRFLLADYFEEQKLSTKE
EALTIFEEIGKPQNIGFDYIQLKEKDNFTLKKYPLKQAFDYAWENLARLDQNPKANQFSV
DECKRFFKEVFSMEMDNINFKTYALLLALKEKTTAFDKKGEGAAKNKSEIIEQIKGVFEE
LDQPFKIIANTLREEVIKKEDELNVLKRQYRETDRKIKTLQNEIKKIKNQIKNLENSKKYS
FPEIIKWIDLTEQEQLLDKNKQAKSNYQKAKGDLGLIRGSQKTSINDYFYLTDKVYRKL
AQDFGKKMADLREKLLDKNDVNKIKYLSYIVKDNQGYQYTLLKPLEDKNAEIIELKSEP
NGDLKLFEIKSLTSKTLNKFIKNKGAYKEFHSAEFEHKKIKEDWKNYKYNSDFIVKLKK
CLSHSDMANTQNWKAFGWDLDKCKSYETIEKEIDQKSYQLVEIKLSKTTIEKWVKENN
YLLLPIVNQDITAEKLKVNTNQFTKDWQHIFEKNPNHRLHPEFNIAYRQPTKDYAKEGE
KRYSRFQLTGQFMYEYIPQDANYISRKEQITLFNDKEEQKIQVETFNNQIAKILNAEDFY
V<u>IGIDRG</u>ITQLATLCVLNKNGVIQGGFEIFTREFDYTNKQWKHTKLKENRNILDISNLKVE
TTVNGEKVLVDLSEVKTYLRDENGEPMKNEKGVILTKDNLQKIKLKQLAYDRKLQYK
MQHEPELVLSFLDRLENKEQIPNLLASTKLISAYKEGTAYADIDIEQFWNILQTFQTIVDK
FGGIENAKKTMEFRQYTELDASFDLKNGVVANMVGVVKFIMEKYNYKTF<u>IALEDL</u>TFA
FGQSIDGINGERLRSTKEDKEVDFKEQENSTLAGLGTYHFFEMQLLKKLSKTQIGNEIKH
FVPAFRSTENYEKIVRKDKNVKAKIVSYPFGIVSFVNPRNTSISCPNCKNANKSNRIKKEN
DRILCKHNIEKTKGNCGFDTANFDENKLRAENKGKNFKY<u>ISSGDANAA</u>YNIAVKLLEDK
IFEINKK

FIG. 1

DR Sequence (Seq ID NO:2): 5' GTTTAAAAACCTTTAAAATTTCTACTATTGTAGAT 3'

FIG 2

SEQUENCE LISTING

```
<160> NUMBER OF SEQ ID NOS: 60

<210> SEQ ID NO 1
<211> LENGTH: 1320
<212> TYPE: PRT
<213> ORGANISM: Unknown
<220> FEATURE:
<223> OTHER INFORMATION: bacterial

<400> SEQUENCE: 1

Met Gln Gln Tyr Gln Val Ser Lys Thr Val Arg Phe Gly Leu Thr Leu
1               5                   10                  15

Lys Asn Ser Glu Lys Lys His Ala Thr His Leu Leu Lys Asp Leu
            20                  25                  30

Val Asn Val Ser Glu Glu Arg Ile Lys Asn Glu Ile Thr Lys Asp Asp
        35                  40                  45

Lys Asn Gln Ser Glu Leu Ser Phe Phe Asn Glu Val Ile Glu Thr Leu
    50                  55                  60

Asp Leu Met Asp Lys Tyr Ile Lys Asp Trp Glu Asn Cys Phe Tyr Arg
65                  70                  75                  80

Thr Asp Gln Ile Gln Leu Thr Lys Glu Tyr Tyr Lys Val Ile Ala Lys
```

85                  90                  95
Lys Ala Cys Phe Asp Trp Phe Trp Thr Asn Asp Arg Gly Met Lys Phe
                100                 105                 110

Pro Thr Ser Ser Ile Ile Ser Phe Asn Ser Leu Lys Ser Ser Asp Lys
                115                 120                 125

Ser Lys Thr Ser Asp Asn Leu Asp Arg Lys Lys Ile Leu Asp Tyr
        130                 135                 140

Trp Lys Gly Asn Ile Phe Lys Thr Gln Lys Ala Ile Lys Asp Val Leu
145                 150                 155                 160

Asp Ile Thr Glu Asp Ile Gln Lys Ala Ile Glu Glu Lys Lys Ser His
                165                 170                 175

Arg Glu Ile Asn Arg Val Asn His Arg Lys Met Gly Ile His Leu Ile
                180                 185                 190

His Leu Ile Asn Asp Thr Leu Val Pro Leu Cys Asn Gly Ser Ile Phe
                195                 200                 205

Phe Gly Asn Ile Ser Lys Leu Asp Phe Cys Glu Ser Glu Asn Glu Lys
        210                 215                 220

Leu Ile Asp Phe Ala Ser Thr Glu Lys Gln Asp Glu Arg Lys Phe Leu
225                 230                 235                 240

Leu Ser Lys Ile Asn Glu Ile Lys Gln Tyr Phe Glu Asp Asn Gly Gly
                245                 250                 255

Asn Val Pro Phe Ala Arg Ala Thr Leu Asn Arg His Thr Ala Asn Gln
                260                 265                 270

Lys Pro Asp Arg Tyr Asn Glu Ile Lys Lys Leu Val Asn Glu Leu
        275                 280                 285

Gly Val Asn Ser Leu Val Arg Ser Leu Lys Ser Lys Thr Ile Glu Glu
                290                 295                 300

Ile Lys Thr His Phe Glu Phe Glu Asn Lys Asn Lys Ile Asn Glu Leu
305                 310                 315                 320

Lys Asn Ser Phe Val Leu Ser Ile Val Glu Lys Ile Gln Leu Phe Lys
                325                 330                 335

Tyr Lys Thr Ile Pro Ala Ser Val Arg Phe Leu Leu Ala Asp Tyr Phe
                340                 345                 350

Glu Glu Gln Lys Leu Ser Thr Lys Glu Ala Leu Thr Ile Phe Glu
        355                 360                 365

Glu Ile Gly Lys Pro Gln Asn Ile Gly Phe Asp Tyr Ile Gln Leu Lys
                370                 375                 380

Glu Lys Asp Asn Phe Thr Leu Lys Lys Tyr Pro Leu Lys Gln Ala Phe
385                 390                 395                 400

Asp Tyr Ala Trp Glu Asn Leu Ala Arg Leu Asp Gln Asn Pro Lys Ala
                405                 410                 415

Asn Gln Phe Ser Val Asp Glu Cys Lys Arg Phe Phe Lys Glu Val Phe
                420                 425                 430

Ser Met Glu Met Asp Asn Ile Asn Phe Lys Thr Tyr Ala Leu Leu Leu
        435                 440                 445

Ala Leu Lys Glu Lys Thr Thr Ala Phe Asp Lys Lys Gly Glu Gly Ala
        450                 455                 460

Ala Lys Asn Lys Ser Glu Ile Ile Glu Gln Ile Lys Gly Val Phe Glu
465                 470                 475                 480

Glu Leu Asp Gln Pro Phe Lys Ile Ile Ala Asn Thr Leu Arg Glu Glu
                485                 490                 495

Val Ile Lys Lys Glu Asp Glu Leu Asn Val Leu Lys Arg Gln Tyr Arg
                500                 505                 510

```
Glu Thr Asp Arg Lys Ile Lys Thr Leu Gln Asn Glu Ile Lys Lys Ile
            515                 520                 525
Lys Asn Gln Ile Lys Asn Leu Glu Asn Ser Lys Lys Tyr Ser Phe Pro
        530                 535                 540
Glu Ile Ile Lys Trp Ile Asp Leu Thr Glu Gln Glu Leu Leu Asp
545                 550                 555                 560
Lys Asn Lys Gln Ala Lys Ser Asn Tyr Gln Lys Ala Lys Gly Asp Leu
                565                 570                 575
Gly Leu Ile Arg Gly Ser Gln Lys Thr Ser Ile Asn Asp Tyr Phe Tyr
            580                 585                 590
Leu Thr Asp Lys Val Tyr Arg Lys Leu Ala Gln Asp Phe Gly Lys Lys
        595                 600                 605
Met Ala Asp Leu Arg Glu Lys Leu Leu Asp Lys Asn Asp Val Asn Lys
    610                 615                 620
Ile Lys Tyr Leu Ser Tyr Ile Val Lys Asp Asn Gln Gly Tyr Gln Tyr
625                 630                 635                 640
Thr Leu Leu Lys Pro Leu Glu Asp Lys Asn Ala Glu Ile Ile Glu Leu
                645                 650                 655
Lys Ser Glu Pro Asn Gly Asp Leu Lys Leu Phe Glu Ile Lys Ser Leu
            660                 665                 670
Thr Ser Lys Thr Leu Asn Lys Phe Ile Lys Asn Lys Gly Ala Tyr Lys
        675                 680                 685
Glu Phe His Ser Ala Glu Phe Glu His Lys Lys Ile Lys Glu Asp Trp
    690                 695                 700
Lys Asn Tyr Lys Tyr Asn Ser Asp Phe Ile Val Lys Leu Lys Lys Cys
705                 710                 715                 720
Leu Ser His Ser Asp Met Ala Asn Thr Gln Asn Trp Lys Ala Phe Gly
                725                 730                 735
Trp Asp Leu Asp Lys Cys Lys Ser Tyr Glu Thr Ile Glu Lys Glu Ile
            740                 745                 750
Asp Gln Lys Ser Tyr Gln Leu Val Glu Ile Lys Leu Ser Lys Thr Thr
        755                 760                 765
Ile Glu Lys Trp Val Lys Glu Asn Asn Tyr Leu Leu Pro Ile Val
    770                 775                 780
Asn Gln Asp Ile Thr Ala Glu Lys Leu Lys Val Asn Thr Asn Gln Phe
785                 790                 795                 800
Thr Lys Asp Trp Gln His Ile Phe Glu Lys Asn Pro Asn His Arg Leu
                805                 810                 815
His Pro Glu Phe Asn Ile Ala Tyr Arg Gln Pro Thr Lys Asp Tyr Ala
            820                 825                 830
Lys Glu Gly Glu Lys Arg Tyr Ser Arg Phe Gln Leu Thr Gly Gln Phe
        835                 840                 845
Met Tyr Glu Tyr Ile Pro Gln Asp Ala Asn Tyr Ile Ser Arg Lys Glu
    850                 855                 860
Gln Ile Thr Leu Phe Asn Asp Lys Glu Glu Gln Lys Ile Gln Val Glu
865                 870                 875                 880
Thr Phe Asn Asn Gln Ile Ala Lys Ile Leu Asn Ala Glu Asp Phe Tyr
                885                 890                 895
Val Ile Gly Ile Asp Arg Gly Ile Thr Gln Leu Ala Thr Leu Cys Val
            900                 905                 910
Leu Asn Lys Asn Gly Val Ile Gln Gly Gly Phe Glu Ile Phe Thr Arg
        915                 920                 925
```

```
Glu Phe Asp Tyr Thr Asn Lys Gln Trp Lys His Thr Lys Leu Lys Glu
    930             935             940
Asn Arg Asn Ile Leu Asp Ile Ser Asn Leu Lys Val Glu Thr Thr Val
945             950             955             960
Asn Gly Glu Lys Val Leu Val Asp Leu Ser Glu Val Lys Thr Tyr Leu
                965             970             975
Arg Asp Glu Asn Gly Glu Pro Met Lys Asn Glu Lys Gly Val Ile Leu
            980             985             990
Thr Lys Asp Asn Leu Gln Lys Ile Lys Leu Lys Gln Leu Ala Tyr Asp
        995             1000            1005
Arg Lys Leu Gln Tyr Lys Met Gln His Glu Pro Glu Leu Val Leu
    1010            1015            1020
Ser Phe Leu Asp Arg Leu Glu Asn Lys Glu Gln Ile Pro Asn Leu
    1025            1030            1035
Leu Ala Ser Thr Lys Leu Ile Ser Ala Tyr Lys Glu Gly Thr Ala
    1040            1045            1050
Tyr Ala Asp Ile Asp Ile Glu Gln Phe Trp Asn Ile Leu Gln Thr
    1055            1060            1065
Phe Gln Thr Ile Val Asp Lys Phe Gly Gly Ile Glu Asn Ala Lys
    1070            1075            1080
Lys Thr Met Glu Phe Arg Gln Tyr Thr Glu Leu Asp Ala Ser Phe
    1085            1090            1095
Asp Leu Lys Asn Gly Val Val Ala Asn Met Val Gly Val Val Lys
    1100            1105            1110
Phe Ile Met Glu Lys Tyr Asn Tyr Lys Thr Phe Ile Ala Leu Glu
    1115            1120            1125
Asp Leu Thr Phe Ala Phe Gly Gln Ser Ile Asp Gly Ile Asn Gly
    1130            1135            1140
Glu Arg Leu Arg Ser Thr Lys Glu Asp Lys Glu Val Asp Phe Lys
    1145            1150            1155
Glu Gln Glu Asn Ser Thr Leu Ala Gly Leu Gly Thr Tyr His Phe
    1160            1165            1170
Phe Glu Met Gln Leu Leu Lys Lys Leu Ser Lys Thr Gln Ile Gly
    1175            1180            1185
Asn Glu Ile Lys His Phe Val Pro Ala Phe Arg Ser Thr Glu Asn
    1190            1195            1200
Tyr Glu Lys Ile Val Arg Lys Asp Lys Asn Val Lys Ala Lys Ile
    1205            1210            1215
Val Ser Tyr Pro Phe Gly Ile Val Ser Phe Val Asn Pro Arg Asn
    1220            1225            1230
Thr Ser Ile Ser Cys Pro Asn Cys Lys Asn Ala Asn Lys Ser Asn
    1235            1240            1245
Arg Ile Lys Lys Glu Asn Asp Arg Ile Leu Cys Lys His Asn Ile
    1250            1255            1260
Glu Lys Thr Lys Gly Asn Cys Gly Phe Asp Thr Ala Asn Phe Asp
    1265            1270            1275
Glu Asn Lys Leu Arg Ala Glu Asn Lys Gly Lys Asn Phe Lys Tyr
    1280            1285            1290
Ile Ser Ser Gly Asp Ala Asn Ala Ala Tyr Asn Ile Ala Val Lys
    1295            1300            1305
Leu Leu Glu Asp Lys Ile Phe Glu Ile Asn Lys Lys
    1310            1315            1320
```

-continued

<210> SEQ ID NO 2
<211> LENGTH: 36
<212> TYPE: DNA
<213> ORGANISM: Unknown
<220> FEATURE:
<223> OTHER INFORMATION: bacterial

<400> SEQUENCE: 2
gtttaaaaaa cctttaaaat ttctactatt gtagat        36

<210> SEQ ID NO 3
<211> LENGTH: 84
<212> TYPE: PRT
<213> ORGANISM: Artificial Sequence
<220> FEATURE:
<223> OTHER INFORMATION: synthetic

<400> SEQUENCE: 3

Met Ala Ser Met Ile Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30

Met Thr Gly Phe Pro Val Arg Lys Val Asn Thr Asp Ile Thr Ser Ile
        35                  40                  45

Thr Ser Asn Gly Gly Arg Val Lys Cys Met Gln Val Trp Pro Pro Ile
    50                  55                  60

Gly Lys Lys Lys Phe Glu Thr Leu Ser Tyr Leu Pro Pro Leu Thr Arg
65                  70                  75                  80

Asp Ser Arg Ala

<210> SEQ ID NO 4
<211> LENGTH: 57
<212> TYPE: PRT
<213> ORGANISM: Artificial Sequence
<220> FEATURE:
<223> OTHER INFORMATION: synthetic

<400> SEQUENCE: 4

Met Ala Ser Met Ile Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30

Met Thr Gly Phe Pro Val Arg Lys Val Asn Thr Asp Ile Thr Ser Ile
        35                  40                  45

Thr Ser Asn Gly Gly Arg Val Lys Ser
    50                  55

<210> SEQ ID NO 5
<211> LENGTH: 85
<212> TYPE: PRT
<213> ORGANISM: Artificial Sequence
<220> FEATURE:
<223> OTHER INFORMATION: synthetic

<400> SEQUENCE: 5

Met Ala Ser Ser Met Leu Ser Ser Ala Thr Met Val Ala Ser Pro Ala
1               5                   10                  15

Gln Ala Thr Met Val Ala Pro Phe Asn Gly Leu Lys Ser Ser Ala Ala
            20                  25                  30

Phe Pro Ala Thr Arg Lys Ala Asn Asn Asp Ile Thr Ser Ile Thr Ser
        35                  40                  45

Asn Gly Gly Arg Val Asn Cys Met Gln Val Trp Pro Pro Ile Glu Lys
    50                  55                  60

Lys Lys Phe Glu Thr Leu Ser Tyr Leu Pro Asp Leu Thr Asp Ser Gly
65                  70                  75                  80

Gly Arg Val Asn Cys
                85

<210> SEQ ID NO 6
<211> LENGTH: 76
<212> TYPE: PRT
<213> ORGANISM: Artificial Sequence
<220> FEATURE:
<223> OTHER INFORMATION: synthetic

<400> SEQUENCE: 6

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
                20                  25                  30

Ser Leu Lys Thr Gln Gln His Pro Arg Ala Tyr Pro Ile Ser Ser Ser
            35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys
65                  70                  75

<210> SEQ ID NO 7
<211> LENGTH: 76
<212> TYPE: PRT
<213> ORGANISM: Artificial Sequence
<220> FEATURE:
<223> OTHER INFORMATION: synthetic

<400> SEQUENCE: 7

Met Ala Gln Val Ser Arg Ile Cys Asn Gly Val Trp Asn Pro Ser Leu
1               5                   10                  15

Ile Ser Asn Leu Ser Lys Ser Ser Gln Arg Lys Ser Pro Leu Ser Val
                20                  25                  30

Ser Leu Lys Thr Gln Gln His Pro Arg Ala Tyr Pro Ile Ser Ser Ser
            35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys
65                  70                  75

<210> SEQ ID NO 8
<211> LENGTH: 72
<212> TYPE: PRT
<213> ORGANISM: Artificial Sequence
<220> FEATURE:
<223> OTHER INFORMATION: synthetic

<400> SEQUENCE: 8

Met Ala Gln Ile Asn Asn Met Ala Gln Gly Ile Gln Thr Leu Asn Pro
1               5                   10                  15

Asn Ser Asn Phe His Lys Pro Gln Val Pro Lys Ser Ser Phe Leu
                20                  25                  30

Val Phe Gly Ser Lys Lys Leu Lys Asn Ser Ala Asn Ser Met Leu Val
            35                  40                  45

Leu Lys Lys Asp Ser Ile Phe Met Gln Leu Phe Cys Ser Phe Arg Ile

```
                    50                  55                  60

Ser Ala Ser Val Ala Thr Ala Cys
 65                  70

<210> SEQ ID NO 9
<211> LENGTH: 69
<212> TYPE: PRT
<213> ORGANISM: Artificial Sequence
<220> FEATURE:
<223> OTHER INFORMATION: synthetic

<400> SEQUENCE: 9

Met Ala Ala Leu Val Thr Ser Gln Leu Ala Thr Ser Gly Thr Val Leu
 1               5                  10                  15

Ser Val Thr Asp Arg Phe Arg Arg Pro Gly Phe Gln Gly Leu Arg Pro
                20                  25                  30

Arg Asn Pro Ala Asp Ala Ala Leu Gly Met Arg Thr Val Gly Ala Ser
                35                  40                  45

Ala Ala Pro Lys Gln Ser Arg Lys Pro His Arg Phe Asp Arg Arg Cys
    50                  55                  60

Leu Ser Met Val Val
 65

<210> SEQ ID NO 10
<211> LENGTH: 77
<212> TYPE: PRT
<213> ORGANISM: Artificial Sequence
<220> FEATURE:
<223> OTHER INFORMATION: synthetic

<400> SEQUENCE: 10

Met Ala Ala Leu Thr Thr Ser Gln Leu Ala Thr Ser Ala Thr Gly Phe
 1               5                  10                  15

Gly Ile Ala Asp Arg Ser Ala Pro Ser Ser Leu Leu Arg His Gly Phe
                20                  25                  30

Gln Gly Leu Lys Pro Arg Ser Pro Ala Gly Gly Asp Ala Thr Ser Leu
                35                  40                  45

Ser Val Thr Thr Ser Ala Arg Ala Thr Pro Lys Gln Gln Arg Ser Val
    50                  55                  60

Gln Arg Gly Ser Arg Arg Phe Pro Ser Val Val Val Cys
 65                  70                  75

<210> SEQ ID NO 11
<211> LENGTH: 57
<212> TYPE: PRT
<213> ORGANISM: Artificial Sequence
<220> FEATURE:
<223> OTHER INFORMATION: synthetic

<400> SEQUENCE: 11

Met Ala Ser Ser Val Leu Ser Ser Ala Ala Val Ala Thr Arg Ser Asn
 1               5                  10                  15

Val Ala Gln Ala Asn Met Val Ala Pro Phe Thr Gly Leu Lys Ser Ala
                20                  25                  30

Ala Ser Phe Pro Val Ser Arg Lys Gln Asn Leu Asp Ile Thr Ser Ile
                35                  40                  45

Ala Ser Asn Gly Gly Arg Val Gln Cys
    50                  55

<210> SEQ ID NO 12
```

```
<211> LENGTH: 65
<212> TYPE: PRT
<213> ORGANISM: Artificial Sequence
<220> FEATURE:
<223> OTHER INFORMATION: synthetic

<400> SEQUENCE: 12

Met Glu Ser Leu Ala Ala Thr Ser Val Phe Ala Pro Ser Arg Val Ala
1               5                   10                  15

Val Pro Ala Ala Arg Ala Leu Val Arg Ala Gly Thr Val Val Pro Thr
            20                  25                  30

Arg Arg Thr Ser Ser Thr Ser Gly Thr Ser Gly Val Lys Cys Ser Ala
        35                  40                  45

Ala Val Thr Pro Gln Ala Ser Pro Val Ile Ser Arg Ser Ala Ala Ala
    50                  55                  60

Ala
65

<210> SEQ ID NO 13
<211> LENGTH: 72
<212> TYPE: PRT
<213> ORGANISM: Artificial Sequence
<220> FEATURE:
<223> OTHER INFORMATION: synthetic

<400> SEQUENCE: 13

Met Gly Ala Ala Ala Thr Ser Met Gln Ser Leu Lys Phe Ser Asn Arg
1               5                   10                  15

Leu Val Pro Pro Ser Arg Arg Leu Ser Pro Val Pro Asn Asn Val Thr
            20                  25                  30

Cys Asn Asn Leu Pro Lys Ser Ala Ala Pro Val Arg Thr Val Lys Cys
        35                  40                  45

Cys Ala Ser Ser Trp Asn Ser Thr Ile Asn Gly Ala Ala Ala Thr Thr
    50                  55                  60

Asn Gly Ala Ser Ala Ala Ser Ser
65                  70

<210> SEQ ID NO 14
<211> LENGTH: 89
<212> TYPE: RNA
<213> ORGANISM: Unknown
<220> FEATURE:
<223> OTHER INFORMATION: bacterial

<400> SEQUENCE: 14
aguuacuauu guaacaauug caaaccuagg ucuuaauauu cuauaauaug acaaaaagca      60
uaaaaacaag ccaagaagca uuguuuuuu                                       89

<210> SEQ ID NO 15
<211> LENGTH: 18
<212> TYPE: DNA
<213> ORGANISM: Unknown
<220> FEATURE:
<223> OTHER INFORMATION: bacterial

<400> SEQUENCE: 15
atttctacta ttgtagat                                                   18

<210> SEQ ID NO 16
<211> LENGTH: 20
<212> TYPE: PRT
<213> ORGANISM: Artificial Sequence
```

```
<220> FEATURE:
<223> OTHER INFORMATION: synthetic
<220> FEATURE:
<221> NAME/KEY: VARIANT
<222> LOCATION: (4)..(4)
<223> OTHER INFORMATION: Xaa is independently selected from lysine,
      histidine, and arginine
<220> FEATURE:
<221> NAME/KEY: VARIANT
<222> LOCATION: (8)..(8)
<223> OTHER INFORMATION: Xaa is independently selected from lysine,
      histidine, and arginine
<220> FEATURE:
<221> NAME/KEY: VARIANT
<222> LOCATION: (11)..(11)
<223> OTHER INFORMATION: Xaa is independently selected from lysine,
      histidine, and arginine
<220> FEATURE:
<221> NAME/KEY: VARIANT
<222> LOCATION: (15)..(15)
<223> OTHER INFORMATION: Xaa is independently selected from lysine,
      histidine, and arginine
<220> FEATURE:
<221> NAME/KEY: VARIANT
<222> LOCATION: (19)..(19)
<223> OTHER INFORMATION: Xaa is independently selected from lysine,
      histidine, and arginine

<400> SEQUENCE: 16

Gly Leu Phe Xaa Ala Leu Leu Xaa Leu Leu Xaa Ser Leu Trp Xaa Leu
1               5                   10                  15

Leu Leu Xaa Ala
            20

<210> SEQ ID NO 17
<211> LENGTH: 20
<212> TYPE: PRT
<213> ORGANISM: Artificial Sequence
<220> FEATURE:
<223> OTHER INFORMATION: synthetic

<400> SEQUENCE: 17

Gly Leu Phe His Ala Leu Leu His Leu Leu His Ser Leu Trp His Leu
1               5                   10                  15

Leu Leu His Ala
            20

<210> SEQ ID NO 18
<211> LENGTH: 16
<212> TYPE: PRT
<213> ORGANISM: Artificial Sequence
<220> FEATURE:
<223> OTHER INFORMATION: synthetic

<400> SEQUENCE: 18

Lys Arg Pro Ala Ala Thr Lys Lys Ala Gly Gln Ala Lys Lys Lys Lys
1               5                   10                  15

<210> SEQ ID NO 19
<211> LENGTH: 9
<212> TYPE: PRT
<213> ORGANISM: Artificial Sequence
<220> FEATURE:
<223> OTHER INFORMATION: synthetic

<400> SEQUENCE: 19

Pro Ala Ala Lys Arg Val Lys Leu Asp
1               5
```

```
<210> SEQ ID NO 20
<211> LENGTH: 11
<212> TYPE: PRT
<213> ORGANISM: Artificial Sequence
<220> FEATURE:
<223> OTHER INFORMATION: synthetic

<400> SEQUENCE: 20

Arg Gln Arg Arg Asn Glu Leu Lys Arg Ser Pro
1               5                   10

<210> SEQ ID NO 21
<211> LENGTH: 38
<212> TYPE: PRT
<213> ORGANISM: Artificial Sequence
<220> FEATURE:
<223> OTHER INFORMATION: synthetic

<400> SEQUENCE: 21

Asn Gln Ser Ser Asn Phe Gly Pro Met Lys Gly Gly Asn Phe Gly Gly
1               5                   10                  15

Arg Ser Ser Gly Pro Tyr Gly Gly Gly Gln Tyr Phe Ala Lys Pro
            20                  25                  30

Arg Asn Gln Gly Gly Tyr
        35

<210> SEQ ID NO 22
<211> LENGTH: 42
<212> TYPE: PRT
<213> ORGANISM: Artificial Sequence
<220> FEATURE:
<223> OTHER INFORMATION: synthetic

<400> SEQUENCE: 22

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 23
<211> LENGTH: 8
<212> TYPE: PRT
<213> ORGANISM: Artificial Sequence
<220> FEATURE:
<223> OTHER INFORMATION: synthetic

<400> SEQUENCE: 23

Val Ser Arg Lys Arg Pro Arg Pro
1               5

<210> SEQ ID NO 24
<211> LENGTH: 8
<212> TYPE: PRT
<213> ORGANISM: Artificial Sequence
<220> FEATURE:
<223> OTHER INFORMATION: synthetic

<400> SEQUENCE: 24

Pro Pro Lys Lys Ala Arg Glu Asp
1               5

<210> SEQ ID NO 25
<211> LENGTH: 8
```

```
<212> TYPE: PRT
<213> ORGANISM: Homo sapiens

<400> SEQUENCE: 25

Pro Gln Pro Lys Lys Lys Pro Leu
1               5

<210> SEQ ID NO 26
<211> LENGTH: 12
<212> TYPE: PRT
<213> ORGANISM: Mus musculus

<400> SEQUENCE: 26

Ser Ala Leu Ile Lys Lys Lys Lys Lys Met Ala Pro
1               5                   10

<210> SEQ ID NO 27
<211> LENGTH: 5
<212> TYPE: PRT
<213> ORGANISM: Artificial Sequence
<220> FEATURE:
<223> OTHER INFORMATION: synthetic

<400> SEQUENCE: 27

Asp Arg Leu Arg Arg
1               5

<210> SEQ ID NO 28
<211> LENGTH: 7
<212> TYPE: PRT
<213> ORGANISM: Influenza virus

<400> SEQUENCE: 28

Pro Lys Gln Lys Lys Arg Lys
1               5

<210> SEQ ID NO 29
<211> LENGTH: 10
<212> TYPE: PRT
<213> ORGANISM: Hepatitis B virus

<400> SEQUENCE: 29

Arg Lys Leu Lys Lys Lys Ile Lys Lys Leu
1               5                   10

<210> SEQ ID NO 30
<211> LENGTH: 10
<212> TYPE: PRT
<213> ORGANISM: Mus musculus

<400> SEQUENCE: 30

Arg Glu Lys Lys Lys Phe Leu Lys Arg Arg
1               5                   10

<210> SEQ ID NO 31
<211> LENGTH: 20
<212> TYPE: PRT
<213> ORGANISM: Homo sapiens

<400> SEQUENCE: 31

Lys Arg Lys Gly Asp Glu Val Asp Gly Val Asp Glu Val Ala Lys Lys
1               5                   10                  15

Lys Ser Lys Lys
            20
```

<210> SEQ ID NO 32
<211> LENGTH: 17
<212> TYPE: PRT
<213> ORGANISM: Homo sapiens

<400> SEQUENCE: 32

Arg Lys Cys Leu Gln Ala Gly Met Asn Leu Glu Ala Arg Lys Thr Lys
1               5                   10                  15

Lys

<210> SEQ ID NO 33
<211> LENGTH: 11
<212> TYPE: PRT
<213> ORGANISM: Human immunodeficiency virus type 1

<400> SEQUENCE: 33

Tyr Gly Arg Lys Lys Arg Arg Gln Arg Arg Arg
1               5                   10

<210> SEQ ID NO 34
<211> LENGTH: 12
<212> TYPE: PRT
<213> ORGANISM: Artificial Sequence
<220> FEATURE:
<223> OTHER INFORMATION: synthetic

<400> SEQUENCE: 34

Arg Arg Gln Arg Arg Thr Ser Lys Leu Met Lys Arg
1               5                   10

<210> SEQ ID NO 35
<211> LENGTH: 27
<212> TYPE: PRT
<213> ORGANISM: Artificial Sequence
<220> FEATURE:
<223> OTHER INFORMATION: synthetic

<400> SEQUENCE: 35

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 36
<211> LENGTH: 33
<212> TYPE: PRT
<213> ORGANISM: Artificial Sequence
<220> FEATURE:
<223> OTHER INFORMATION: synthetic

<400> SEQUENCE: 36

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 37
<211> LENGTH: 16
<212> TYPE: PRT
<213> ORGANISM: Artificial sequence
<220> FEATURE:
<223> OTHER INFORMATION: synthetic

```
<400> SEQUENCE: 37

Arg Gln Ile Lys Ile Trp Phe Gln Asn Arg Arg Met Lys Trp Lys Lys
1               5                   10                  15

<210> SEQ ID NO 38
<211> LENGTH: 11
<212> TYPE: PRT
<213> ORGANISM: Artificial sequence
<220> FEATURE:
<223> OTHER INFORMATION: synthetic

<400> SEQUENCE: 38

Tyr Gly Arg Lys Lys Arg Arg Gln Arg Arg Arg
1               5                   10

<210> SEQ ID NO 39
<211> LENGTH: 9
<212> TYPE: PRT
<213> ORGANISM: Artificial sequence
<220> FEATURE:
<223> OTHER INFORMATION: synthetic

<400> SEQUENCE: 39

Arg Lys Lys Arg Arg Gln Arg Arg Arg
1               5

<210> SEQ ID NO 40
<211> LENGTH: 11
<212> TYPE: PRT
<213> ORGANISM: Artificial sequence
<220> FEATURE:
<223> OTHER INFORMATION: synthetic

<400> SEQUENCE: 40

Tyr Gly Arg Lys Lys Arg Arg Gln Arg Arg Arg
1               5                   10

<210> SEQ ID NO 41
<211> LENGTH: 8
<212> TYPE: PRT
<213> ORGANISM: Artificial sequence
<220> FEATURE:
<223> OTHER INFORMATION: synthetic

<400> SEQUENCE: 41

Arg Lys Lys Arg Arg Gln Arg Arg
1               5

<210> SEQ ID NO 42
<211> LENGTH: 11
<212> TYPE: PRT
<213> ORGANISM: Artificial sequence
<220> FEATURE:
<223> OTHER INFORMATION: synthetic

<400> SEQUENCE: 42

Tyr Ala Arg Ala Ala Ala Arg Gln Ala Arg Ala
1               5                   10

<210> SEQ ID NO 43
<211> LENGTH: 11
<212> TYPE: PRT
<213> ORGANISM: Artificial sequence
<220> FEATURE:
<223> OTHER INFORMATION: synthetic

<400> SEQUENCE: 43
```

```
Thr His Arg Leu Pro Arg Arg Arg Arg Arg
1               5                   10

<210> SEQ ID NO 44
<211> LENGTH: 11
<212> TYPE: PRT
<213> ORGANISM: Artificial sequence
<220> FEATURE:
<223> OTHER INFORMATION: synthetic

<400> SEQUENCE: 44

Gly Gly Arg Arg Ala Arg Arg Arg Arg Arg
1               5                   10

<210> SEQ ID NO 45
<211> LENGTH: 5
<212> TYPE: PRT
<213> ORGANISM: Artificial sequence
<220> FEATURE:
<223> OTHER INFORMATION: synthetic

<400> SEQUENCE: 45

Gly Ser Gly Gly Ser
1               5

<210> SEQ ID NO 46
<211> LENGTH: 6
<212> TYPE: PRT
<213> ORGANISM: Artificial sequence
<220> FEATURE:
<223> OTHER INFORMATION: synthetic

<400> SEQUENCE: 46

Gly Gly Ser Gly Gly Ser
1               5

<210> SEQ ID NO 47
<211> LENGTH: 4
<212> TYPE: PRT
<213> ORGANISM: Artificial sequence
<220> FEATURE:
<223> OTHER INFORMATION: synthetic

<400> SEQUENCE: 47

Gly Gly Gly Ser
1

<210> SEQ ID NO 48
<211> LENGTH: 4
<212> TYPE: PRT
<213> ORGANISM: Artificial sequence
<220> FEATURE:
<223> OTHER INFORMATION: synthetic

<400> SEQUENCE: 48

Gly Gly Ser Gly
1

<210> SEQ ID NO 49
<211> LENGTH: 5
<212> TYPE: PRT
<213> ORGANISM: Artificial sequence
<220> FEATURE:
<223> OTHER INFORMATION: synthetic

<400> SEQUENCE: 49
```

```
Gly Gly Ser Gly Gly
1               5

<210> SEQ ID NO 50
<211> LENGTH: 5
<212> TYPE: PRT
<213> ORGANISM: Artificial sequence
<220> FEATURE:
<223> OTHER INFORMATION: synthetic

<400> SEQUENCE: 50

Gly Ser Gly Ser Gly
1               5

<210> SEQ ID NO 51
<211> LENGTH: 5
<212> TYPE: PRT
<213> ORGANISM: Artificial sequence
<220> FEATURE:
<223> OTHER INFORMATION: synthetic

<400> SEQUENCE: 51

Gly Ser Gly Gly Gly
1               5

<210> SEQ ID NO 52
<211> LENGTH: 5
<212> TYPE: PRT
<213> ORGANISM: Artificial sequence
<220> FEATURE:
<223> OTHER INFORMATION: synthetic

<400> SEQUENCE: 52

Gly Gly Gly Ser Gly
1               5

<210> SEQ ID NO 53
<211> LENGTH: 5
<212> TYPE: PRT
<213> ORGANISM: Artificial sequence
<220> FEATURE:
<223> OTHER INFORMATION: synthetic

<400> SEQUENCE: 53

Gly Ser Ser Ser Gly
1               5

<210> SEQ ID NO 54
<211> LENGTH: 7
<212> TYPE: PRT
<213> ORGANISM: Artificial sequence
<220> FEATURE:
<223> OTHER INFORMATION: synthetic

<400> SEQUENCE: 54

Ile Gly Ile Asp Arg Gly Ile
1               5

<210> SEQ ID NO 55
<211> LENGTH: 6
<212> TYPE: PRT
<213> ORGANISM: Artificial sequence
<220> FEATURE:
<223> OTHER INFORMATION: synthetic

<400> SEQUENCE: 55

Ile Ala Leu Glu Asp Leu
```

```
<210> SEQ ID NO 56
<211> LENGTH: 8
<212> TYPE: PRT
<213> ORGANISM: Artificial sequence
<220> FEATURE:
<223> OTHER INFORMATION: synthetic

<400> SEQUENCE: 56

Ser Ser Gly Asp Ala Asn Ala Ala
1               5

<210> SEQ ID NO 57
<211> LENGTH: 7
<212> TYPE: PRT
<213> ORGANISM: Simian virus 40

<400> SEQUENCE: 57

Pro Lys Lys Lys Arg Lys Val
1               5

<210> SEQ ID NO 58
<211> LENGTH: 16
<212> TYPE: PRT
<213> ORGANISM: Artificial sequence
<220> FEATURE:
<223> OTHER INFORMATION: synthetic

<400> SEQUENCE: 58

Arg Gln Ile Lys Ile Trp Phe Gln Asn Arg Arg Met Lys Trp Lys Lys
1               5                   10                  15

<210> SEQ ID NO 59
<211> LENGTH: 70
<212> TYPE: RNA
<213> ORGANISM: Unknown
<220> FEATURE:
<223> OTHER INFORMATION: bacterial

<400> SEQUENCE: 59
uuuuaugcuu uuugucauau uauagaauau uaagaccuag guuugcaauu guuacaauag      60
uaacuuuuuu                                                            70

<210> SEQ ID NO 60
<211> LENGTH: 19
<212> TYPE: RNA
<213> ORGANISM: Unknown
<220> FEATURE:
<223> OTHER INFORMATION: bacterial

<400> SEQUENCE: 60
aauuucuacu auuguagau                                                  19
```

RNA-GUIDED NUCLEASES AND DNA BINDING PROTEINS

REFERENCE TO RELATED APPLICATIONS

This application claims benefit of priority to U.S. Provisional Patent Application No. 62/751,379 filed 26 Oct. 2018, and to U.S. Provisional Patent Application No. 62/893,941 filed 30 Aug. 2019, which are each incorporated herein by reference in their entireties.

INCORPORATION OF SEQUENCE LISTING

A sequence listing containing the file named "10017US1_ST25.txt" which is 30,110 bytes (measured in MS-Windows®), comprises 60 biological sequences, and was created on Oct. 24, 2019, is electronically filed herewith via the USPTO's EFS system, and is incorporated herein by reference in its entirety.

FIELD

The invention is generally related to CRISPR (clustered regularly interspaced short palindromic repeat) effector systems.

BACKGROUND

The CRISPR/Cas system of bacterial acquired immunity against phages and viruses has been adapted into potent new technologies for genomic modifications, as well as other research tools. A few Class 2 nucleases have been intensively used and characterized, yet a need remains for alternative nucleases with different properties that may provide optimal performance or options in a variety genome modification or diagnostic applications.

SUMMARY

The present disclosure provides RNA-guided endonuclease polypeptides and RNA-guided DNA binding proteins, referred to herein as "CasJ" polypeptides (also referred to as "CasJ proteins"); nucleic acids encoding the CasJ polypeptides; and modified host cells comprising the CasJ polypeptides and/or nucleic acids encoding same. CasJ polypeptides are useful in a variety of applications, which are provided.

The present disclosure provides guide RNAs (referred to herein as "CasJ guide RNAs") that bind to and provide sequence specificity to the CasJ proteins; nucleic acids encoding the CasJ guide RNAs; and modified host cells comprising the CasJ guide RNAs and/or nucleic acids encoding same. CasJ guide RNAs are useful in a variety of applications, which are provided.

Also provided are DNA detection systems comprising: (i) a CasJ polypeptide or CasJ fusion polypeptide provided herein; (ii) one or more CasJ guide RNAs each comprising a guide sequence that can hybridize to a corresponding target nucleic acid molecule and an activator sequence that can bind to the CasJ polypeptide or CasJ fusion polypeptide; and (iii) a DNA reporter molecule. In certain embodiments, the guide sequence cannot hybridize to the DNA reporter molecule.

Also provided are methods of detecting a target DNA molecule comprising: contacting the target DNA molecule with: (i) a CasJ polypeptide or a CasJ fusion polypeptide provided herein; (ii) one or more CasJ guide RNAs each comprising a guide sequence that can hybridize to the target DNA molecule and an activator sequence that can bind to the CasJ polypeptide or CasJ fusion polypeptide; and (iii) a DNA reporter molecule wherein the CasJ comprises endonuclease enzyme activity, and wherein the reporter molecule does not comprise the target DNA molecule sequence; and assaying for an output of the reporter molecule.

BRIEF DESCRIPTION OF THE DRAWINGS

FIG. 1 depicts the CasJ protein sequence of SEQ ID NO: 1. The RuvC subdomains of RuvC-I (SEQ ID NO: 54), RuvC-II (SEQ ID NO:55), and RuvC-III (SEQ ID NO:56) are underlined.

FIG. 2 shows a Direct Repeat in the CasJ locus (SEQ ID NO: 2).

DETAILED DESCRIPTION

Definitions

Figure 3:
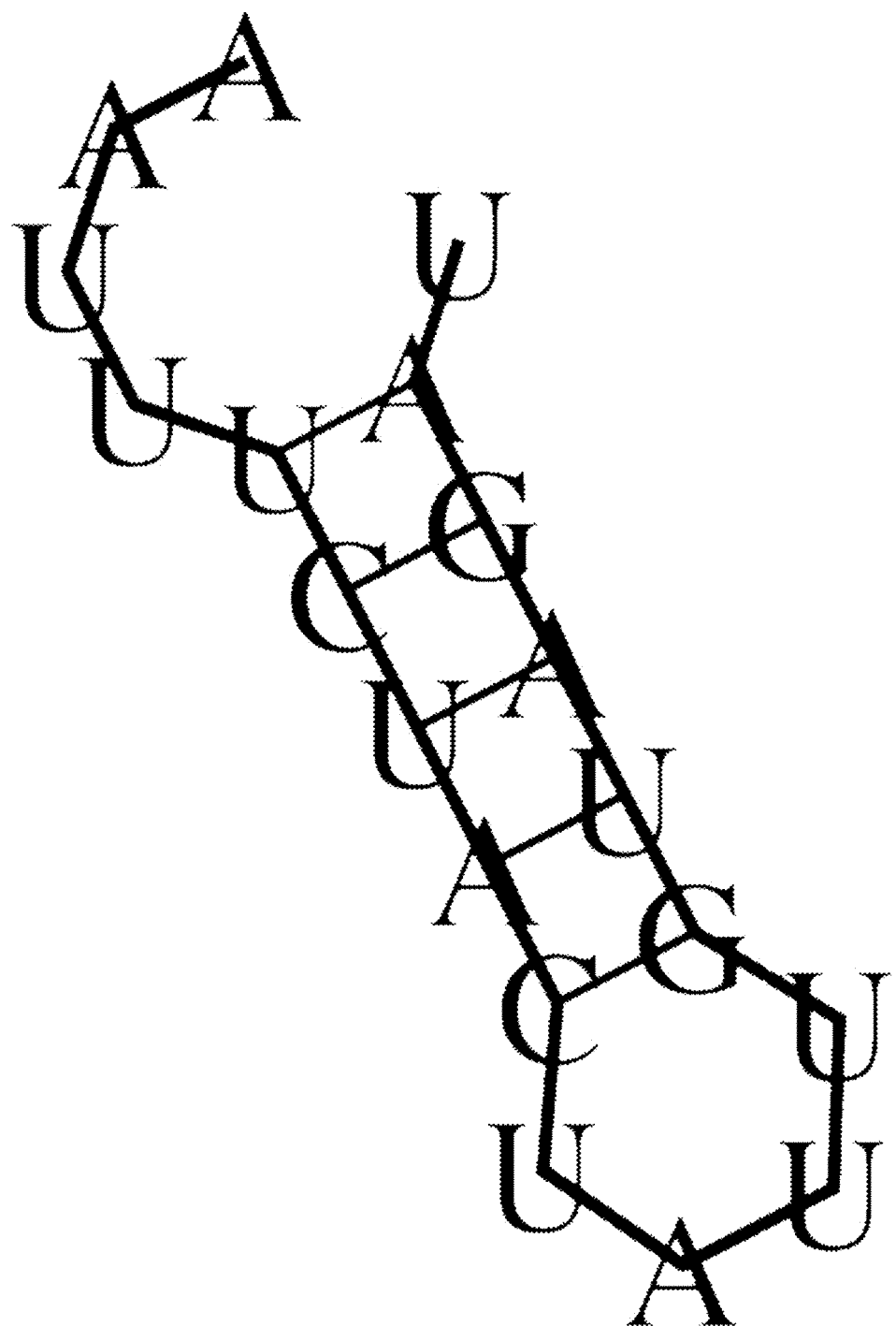
FIG. 3 shows a functional activator sequence for CasJ-binding guide RNA (SEQ ID NO: 60).

The term "and/or" where used herein is to be taken as specific disclosure of each of the two or more specified features or components with or without the other specified features. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the phrase "DNA donor template" refers to a DNA molecule having homology to the target editing site. DNA donor template molecules can be used to edit a target editing site in a genome by homology-directed repair.

"Heterologous," as used herein, means a nucleotide or polypeptide sequence that is not found in the native nucleic acid or protein, respectively. For example, relative to a CasJ polypeptide, a heterologous polypeptide comprises an amino acid sequence from a protein other than the CasJ polypeptide. In some cases, a portion of a CasJ protein from one species is fused to a portion of a Cas protein from a different species. The Cas sequence from each species could therefore be considered to be heterologous relative to one another. As another example, a CasJ protein (e.g., a dCasJ protein) can be fused to an active domain from a non-CasJ protein (e.g., a histone deacetylase), and the sequence of the active domain could be considered a heterologous polypeptide (it is heterologous to the CasJ protein).

The phrase "CasJ fusion polypeptide" as used herein refers to a polypeptide comprising a CasJ polypeptide fused to a heterologous polypeptide. In certain embodiments, the CasJ polypeptide is operably linked to the heterologous polypeptide in the CasJ fusion polypeptide.

As used herein, the terms "correspond," "corresponding," and the like, when used in the context of an amino acid position, mutation, and/or substitution in any given CasJ polypeptide with respect to the reference CasJ polypeptide sequence of SEQ ID NO: 1, all refer to the position, mutation, and/or substitution of the amino acid residue in the given CasJ sequence that has identity or similarity to the amino acid residue in the reference CasJ polypeptide sequence of SEQ ID NO: 1 when the given CasJ polypeptide is aligned to the reference CasJ polypeptide sequence of SEQ ID NO: 1 using a pairwise alignment algorithm (e.g. CLUSTAL O 1.2.4 with default parameters).

As used herein, the terms "include," "includes," and "including" are to be construed as at least having the features to which they refer while not excluding any additional unspecified features.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms "polynucleotide" and "nucleic acid" should be understood to include, as applicable to the embodiment being described, single-stranded (such as sense or antisense) and double-stranded polynucleotides.

The terms "polypeptide," "peptide," and "protein", are used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The term "naturally-occurring" as used herein as applied to a nucleic acid, a protein, a cell, or an organism, refers to a nucleic acid, cell, protein, or organism that is found in nature.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or "recombinant" nucleic acid refers to one which is not naturally-occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally-occurring, e.g., is made by the artificial combination of two otherwise separated segments of amino sequence through human intervention. Thus, e.g., a polypeptide that comprises a heterologous amino acid sequence is recombinant.

By "construct" or "vector" is meant a recombinant nucleic acid, generally recombinant DNA, which has been generated for the purpose of the expression and/or propagation of a specific nucleotide sequence(s), or is to be used in the construction of other recombinant nucleotide sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (e.g., DNA exogenous to the cell) into the cell. Genetic change ("modification") can be accomplished either by incorporation of the new nucleic acid into the genome of the host cell, or by transient or stable maintenance of the new nucleic acid as an episomal element. Where the cell is a eukaryotic cell, a permanent genetic change is generally achieved by introduction of new DNA into the genome of the cell. In prokaryotic cells, permanent changes can be introduced into the chromosome or via extrachromosomal elements such as plasmids and expression vectors, which may contain one or more selectable markers to aid in their maintenance in the recombinant host cell. Suitable methods of genetic modification include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (e.g., in vitro, ex vivo, or in vivo). A general discussion of these methods can be found in Ausubel, et al, Short Protocols in Molecular Biology, 3rd ed., Wiley & Sons, 1995.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject prokaryotic host cell is a genetically modified prokaryotic host cell (e.g., a bacterium), by virtue of introduction into a suitable prokaryotic host cell of a heterologous nucleic acid, e.g., an exogenous nucleic acid that is foreign to (not normally found in nature in) the prokaryotic host cell, or a recombinant nucleic acid that is not normally found in the prokaryotic host cell; and a subject eukaryotic host cell is a genetically modified eukaryotic host cell, by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), /. Mol. Biol. 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. See /. Mol. Biol. 48: 443-453 (1970).

As used herein, the terms "treatment," "treating," and the like, refer to obtaining a desired trait, pharmacologic and/or physiologic effect. The effect can be to confer a desired trait (e.g., improved yield, resistance to insects, fungi, bacterial pathogens, and/or nematodes, herbicide tolerance, abiotic stress tolerance (e.g., drought, cold, salt, and/or heat tolerance), protein quantity and/or quality, starch quantity and/or quality, lipid quantity and/or quality, secondary metabolite quantity and/or quality, and the like, all in comparison to a control plant that lacks the modification. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a plant or mammal, e.g., in a human, and includes: (a) preventing the disease from occurring in a subject which may be predisposed to the disease but has not yet been diagnosed as having it; (b) inhibiting the disease, e.g., arresting its development; and (c) relieving the disease, e.g., causing regression of the disease.

The terms "individual," "subject," "host," and "patient," used interchangeably herein, refer to an individual organism, e.g., a mammal, including, but not limited to, murines, simians, humans, mammalian farm animals, mammalian sport animals, and mammalian pets.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a CasJ polypeptide" includes a plurality of such polypeptides and reference to "the guide RNA" includes reference to one or more guide RNAs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

DESCRIPTION

The present disclosure provides RNA-guided endonuclease polypeptides and RNA-guided DNA binding proteins, referred to herein as "CasJ" polypeptides (also referred to as "CasJ proteins"); nucleic acids encoding the CasJ polypeptides; and modified host cells comprising the CasJ polypeptides and/or nucleic acids encoding same. CasJ polypeptides are useful in a variety of applications, which are provided.

The present disclosure provides guide RNAs (referred to herein as "CasJ guide RNAs") that bind to and provide sequence specificity to the CasJ proteins; nucleic acids encoding the CasJ guide RNAs; and modified host cells comprising the CasJ guide RNAs and/or nucleic acids encoding same. CasJ guide RNAs are useful in a variety of applications, which are provided.

A CRISPR/Cas endonuclease (e.g., a CasJ protein) interacts with (binds to) a corresponding guide RNA (e.g., a CasJ guide RNA) to form a ribonucleoprotein (RNP) complex that is targeted to a particular site in a target nucleic acid via base pairing between the guide RNA and a target sequence within the target nucleic acid molecule. A guide RNA includes a nucleotide sequence (a guide sequence) that is complementary to a sequence (the target site) of a target nucleic acid. Thus, a CasJ protein forms a complex with a CasJ guide RNA and the guide RNA provides sequence specificity to the RNP complex via the guide sequence. The CasJ protein of the complex provides the site-specific activity. In other words, the CasJ protein is guided to a target site (e.g., stabilized at a target site) within a target nucleic acid sequence (e.g., a chromosomal sequence or an extrachromosomal sequence, e.g., an episomal sequence, a minicircle sequence, a mitochondrial sequence, a chloroplast sequence, etc.) by virtue of its association with the guide RNA.

The present disclosure provides compositions comprising a CasJ polypeptide (and/or a nucleic acid encoding the CasJ polypeptide) (e.g., where the CasJ polypeptide can be a naturally-occurring protein, a nickase CasJ protein, a dCasJ protein, a chimeric CasJ protein, or CasJ fusion polypeptide, etc.). The present disclosure provides compositions comprising a CasJ guide RNA (and/or a nucleic acid encoding the CasJ guide RNA) (e.g., where the CasJ guide RNA can be in dual or single guide format). The present disclosure provides compositions comprising (a) a CasJ polypeptide (and/or a nucleic acid encoding the CasJ polypeptide) (e.g., where the CasJ polypeptide can be a naturally-occurring protein, a nickase CasJ protein, a dCasJ protein, a chimeric CasJ protein, a CasJ fusion polypeptide, etc.) and (b) a CasJ guide RNA (and/or a nucleic acid encoding the CasJ guide RNA) (e.g., where the CasJ guide RNA can be in dual or single guide format). The present disclosure provides a nucleic acid/protein complex (RNP complex) comprising: (a) a CasJ polypeptide of the present disclosure (e.g., where the CasJ polypeptide can be a naturally-occurring protein, a nickase CasJ protein, a dCasJ protein, a chimeric CasJ protein, a CasJ fusion polypeptide, etc.); and (b) a CasJ guide RNA (e.g., where the CasJ guide RNA can be in dual or single guide format).

A CasJ polypeptide (this term is used interchangeably with the term "CasJ protein") can bind and/or modify (e.g., cleave, nick, methylate, demethylate, etc.) a target nucleic acid and/or a polypeptide associated with target nucleic acid (e.g., methylation or acetylation of a histone tail) (e.g., in some cases the CasJ protein includes a fusion partner with an activity, and in some cases the CasJ protein provides nuclease activity). In some cases, the CasJ protein is a naturally-occurring protein (e.g., naturally-occurs in prokaryotic cells). In other cases, the CasJ protein is not a naturally-occurring polypeptide (e.g., the CasJ protein is a variant CasJ protein, a chimeric protein, a CasJ fusion polypeptide, and the like).

Assays to determine whether given protein interacts with a CasJ guide RNA can be any convenient binding assay that tests for binding between a protein and a nucleic acid. Suitable binding assays (e.g., gel shift assays) will be known to one of ordinary skill in the art (e.g., assays that include adding a CasJ guide RNA and a protein to a target nucleic acid). Assays to determine whether a protein has an activity (e.g., to determine if the protein has nuclease activity that cleaves a target nucleic acid and/or some heterologous activity) can be any convenient assay (e.g., any convenient nucleic acid cleavage assay that tests for nucleic acid cleavage). Suitable assays (e.g., cleavage assays) will be known to one of ordinary skill in the art.

A naturally-occurring CasJ protein functions as an endonuclease that catalyzes a strand break (double or single strand) at a specific sequence in a targeted DNA. The sequence specificity is provided by the associated guide RNA, which hybridizes to a target sequence within the target DNA. The naturally-occurring guide RNA may include a tracrRNA hybridized to a crRNA or, where the crRNA includes a guide sequence that hybridizes to a target sequence in the target DNA.

As used herein, CasJ endonuclease activity refers to CRISPR endonuclease activity wherein, a guide RNA associated with a CasJ polypeptide causes the CasJ-guide RNA complex to bind to a pre-determined nucleotide sequence that is complementary to the gRNA; and wherein CasJ endonuclease activity can introduce a strand break at or near the site targeted by the gRNA. In certain embodiments, this is a double-stranded break, and it may be a blunt or a staggered DNA double-stranded break. As used herein a "staggered DNA double-stranded break" can result in a double strand break with about 1, about 2, about 3, about 4, about 5, about 6, about 7, about 8, about 9, or about 10 nucleotides of overhang on either the 3' or 5' ends following cleavage. The double strand break can occur at or near the sequence to which the guide sequence is targeted.

In some embodiments, the CasJ protein of the subject methods and/or compositions is (or is derived from) a naturally-occurring (wild type) protein. The sequence of a naturally-occurring CasJ protein is shown in SEQ ID NO: 1.

In some cases, a CasJ protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasJ protein sequence set forth as SEQ ID NO: 1. For example, in some cases, a CasJ protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasJ protein sequence set forth as SEQ ID NO: 1. In some cases, a CasJ protein includes an amino acid sequence having 80% or more sequence identity (e.g., 85% or more, 90% or more, 95% or more, 97% or more, 98% or more, 99% or more, or 100% sequence identity) with the CasJ protein sequence set forth as SEQ ID NO: 1. In some cases, a CasJ protein includes an amino acid sequence having 90% or more sequence identity (e.g., 95% or more, 97% or more, 98% or more, 99% or more, 99.5%, 99.8%, 99.9%, or 100% sequence identity) with the CasJ protein sequence set forth as SEQ ID NO: 1. In some cases, a CasJ protein includes an amino acid sequence having the CasJ protein sequence set forth as SEQ ID NO: 1. In some cases, a CasJ protein includes an amino acid sequence having the CasJ protein sequence set forth as SEQ ID NO: 1, with the exception that the sequence includes an amino acid substitution (e.g., 1, 2, or 3 amino acid substitutions) that reduces the naturally-occurring catalytic activity of the protein (e.g., such as at amino acid positions described below). A CasJ fusion polypeptide can comprise any of the aforementioned CasJ proteins.

CasJ protein includes 3 partial RuvC domains (RuvC-I, RuvC-II, and RuvC-III, also referred to herein as subdomains) that are not contiguous with respect to the primary amino acid sequence of the CasJ protein, but form a RuvC domain once the protein is produced and folds.

In some cases, a CasJ protein (of the subject compositions and/or methods) includes a split RuvC domain (e.g., 3 partial RuvC domains—RuvC-I, RuvC-II, and RuvC-III) with amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the split RuvC domain of SEQ ID NO: 1. The catalytic residues of the RuvC domain of CasJ are SEQ ID NO: 54 for RuvC-I, SEQ ID NO: 55 for RuvC-II, and SEQ ID NO: 56 for RuvC-III. In certain embodiments, CasJ proteins provided herein include proteins comprising an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, 99.5% or more, or 100% sequence identity with the CasJ protein sequence set forth as SEQ ID NO: 1, wherein at least one of the RuvC subdomains of SEQ ID NO: 54, SEQ ID NO: 55, and/or SEQ ID NO: 56 are present. A CasJ fusion polypeptide can comprise any of the aforementioned CasJ proteins.

A variant CasJ protein has an amino acid sequence that is different by at least one amino acid (e.g., has a deletion, insertion, substitution, fusion) when compared to the amino acid sequence of the corresponding wild type CasJ protein. A CasJ protein that cleaves one strand but not the other of a double stranded target nucleic acid is referred to herein as a "nickase" (e.g., a "nickase CasJ"). A CasJ protein that has substantially no nuclease activity is referred to herein as a dead CasJ protein ("dCasJ") (with the caveat that nuclease activity can be provided by a heterologous polypeptide—a fusion partner—in the case of a chimeric CasJ protein or a CasJ fusion polypeptide—which is described in more detail below). For any of the CasJ variant proteins described herein (e.g., nickase CasJ, dCasJ, chimeric CasJ, CasJ fusion polypeptide), the CasJ variant can include a CasJ protein sequence with the same parameters described above (e.g., domains that are present, percent identity, and the like).

In certain embodiments, the CasJ protein is a variant CasJ protein, e.g., mutated relative to the naturally-occurring catalytically active sequence, and exhibits reduced cleavage activity (e.g., exhibits 90%, or less, 80% or less, 70% or less, 60% or less, 50% or less, 40% or less, 30% or less, 20% or less, 10% or less, 5% or less, or 1% or less cleavage activity) when compared to the corresponding naturally-occurring sequence. In some cases, such a variant CasJ protein is a catalytically 'dead' protein (has substantially no cleavage activity) and can be referred to as a 'dCasJ.' In some cases, the variant CasJ protein is a nickase (cleaves only one strand of a double stranded target nucleic acid, e.g., a double stranded target DNA). As described in more detail herein, in some cases, a CasJ protein (in some case a CasJ protein with wild type cleavage activity and in some cases a variant CasJ with reduced cleavage activity, e.g., a dCasJ or a nickase CasJ) is fused (conjugated) to a heterologous polypeptide that has an activity of interest (e.g., a catalytic activity of interest) to form a fusion protein (e.g., a chimeric CasJ protein or a CasJ fusion polypeptide).

Conserved catalytic residues of CasJ include the RuvC subdomain residues identified above. D901, E1128 and D1298, numbered according to SEQ ID NO: 1, are residues that can be mutated, for example as D901A, E1128A, or D1298A, to decrease the catalytic activity of a CasJ polypeptide. Thus, in some cases, the CasJ protein has reduced activity in one or more of the above described amino acids (or one or more corresponding amino acids of any CasJ protein) are mutated (e.g., substituted with an alanine). In some cases, the variant CasJ protein is a catalytically 'dead' protein (is catalytically inactive) and is referred to as 'dCasJ.' A dCasJ protein can be fused to a fusion partner that provides an activity, and in some cases, the dCasJ (e.g., one without a fusion partner that provides catalytic activity—but which can have an NLS when expressed in a eukaryotic cell) can bind to target DNA and can block RNA polymerase from translating from a target DNA or the function of other endogenous DNA binding or processing proteins. In some cases, the variant CasJ protein is a nickase (cleaves only one strand of a double stranded target nucleic acid, e.g., a double stranded target DNA). A CasJ fusion polypeptide can comprise any of the aforementioned dCasJ proteins.

A variant CasJ polypeptide can include one or more mutations that enhance protein function. In certain embodiments, CasJ protein enhancement mutations alter the level of gene editing by the CasJ scaffold protein polypeptide, as compared to a CasJ polypeptide lacking the mutations. In certain embodiments, the effect of the CasJ enhancement mutations may include: altered translation, folding, and/or stability of the protein or RNP; altered affinity and/or specificity of target binding; altered nuclease efficiency on target and/or non-target strands; altered PAM recognition specificity; altered half-life as it may be measured in vivo and/or in vitro; and altered DNA repair outcomes (e.g., increased frequencies of target gene editing and/or decreased frequencies of non-target gene mutations). In certain embodiments, characteristics altered by the CasJ enhancement mutations include: higher solubility, longer active lifespan in vivo or in vitro (e.g., increased half-life), or improved enzymatic activity as may be measured by higher Kcat and or/lower Km, or higher substrate specificity. CasJ protein enhancement mutations include mutations comprising or corresponding to K356F, L593N, D604K, K1113A, K1122N, D1139F, D1139Q, T1185L, S1200L, Y1221K, and L1309G in SEQ ID NO: 1.

A variant CasJ polypeptide can include but is not limited to one or more mutations that enhance the variant CasJ protein's ability to bind, process, and/or stabilize guide RNA. In certain embodiments, mutations that confer improved ability to bind/stabilize guide RNA may alter target DNA binding affinity and/or sequence specificity of the mutated CasJ polypeptide, and/or DNA editing outcome as compared to a wild-type CasJ polypeptide lacking the mutation(s). An enhanced CasJ polypeptide guide RNA binding, processing, and/or stabilization mutation includes a mutation comprising or corresponding to E834I in SEQ ID NO: 1.

To initiate DNA cleavage, a CasJ polypeptide complexes with one or more RNA molecules (guide RNA) comprising a sequence complementary to the intended target site. To cleave DNA in vitro, a purified wild-type or mutated CasJ polypeptide is pre-complexed to guide RNA and incubated with linear double-stranded DNA (e.g., linearized plasmid DNA) having a sequence region complementary to that of the guide RNA. The extent of the cleavage reaction is monitored at different time points or enzyme concentrations by, for example, polyacrylamide gel electrophoresis (Kleinstiver et al., Nat Biotechnol. 2019, 37(3):276-282. doi: 10.1038/s41587-018-0011-0). Compared to the wild type CasJ polypeptide, digestion by the mutant CasJ polypeptide comprising one or more of the CasJ protein mutations that include mutations comprising or corresponding to K356F, L593N, D604K, K1113A, K1122N, D1139F, D1139Q, T1185L, S1200L, Y1221K, L1309G, and/or E834I in SEQ ID NO: 1 may differ in reaction rate, specificity toward the target sequence, enzymatic turnover, product composition (e.g., nicked dsDNA), and/or temperature optimality. In certain embodiments, a mutant CasJ polypeptide comprising one or more of the CasJ protein mutations that include mutations comprising or corresponding to K356F, L593N, D604K, K1113A, K1122N, D1139F, D1139Q, T1185L, S1200L, Y1221K, L1309G, and/or E834I in SEQ ID NO: 1 may differ from the wild-type CasJ polypeptide in processing or binding the guide RNA, or may enable non-natural modifications, insertions, 5' or 3' extensions, or 5' or 3' truncations of the guide RNA. In certain embodiments, such mutant CasJ polypeptides including those comprising one or more of the CasJ protein mutations that include mutations comprising or corresponding to K356F, L593N, D604K, K1113A, K1122N, D1139F, D1139Q, T1185L, S1200L, Y1221K, and/or E834I in SEQ ID NO:1 may demonstrate enhanced efficiency of RNP formation, reduced sensitivity to reaction temperature, or reduced dependence on cofactors for complex assembly.

As noted above, in some cases, a CasJ protein (in some cases a CasJ protein with wild type cleavage activity and in some cases a variant CasJ with reduced cleavage activity, e.g., a dCasJ or a nickase CasJ) is fused (conjugated) to a heterologous polypeptide that has an activity of interest (e.g., a catalytic activity of interest) to form a fusion protein (a chimeric CasJ protein or CasJ fusion polypeptide). A heterologous polypeptide to which a CasJ protein can be fused is referred to herein as a 'fusion partner.'

In some cases the fusion partner can modulate transcription (e.g., inhibit transcription, increase transcription) of a target DNA. For example, in some cases the fusion partner is a protein (or a domain from a protein) that inhibits transcription (e.g., a transcriptional repressor, a protein that functions via recruitment of transcription inhibitor proteins, modification of target DNA such as methylation, recruitment of a DNA modifier, modulation of histones associated with target DNA, recruitment of a histone modifier such as those that modify acetylation and/or methylation of histones, and the like). In some cases the fusion partner is a protein (or a domain from a protein) that increases transcription (e.g., a transcription activator, a protein that acts via recruitment of transcription activator proteins, modification of target DNA such as demethylation, recruitment of a DNA modifier, modulation of histones associated with target DNA, recruitment of a hi stone modifier such as those that modify acetylation and/or methylation of histones, and the like).

In some cases, a chimeric CasJ protein or CasJ fusion polypeptide includes a heterologous polypeptide that has enzymatic activity that modifies a target nucleic acid (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In some cases, a chimeric CasJ protein or CasJ fusion polypeptide includes a heterologous polypeptide that has enzymatic activity that modifies a polypeptide (e.g., a histone) associated with a target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Examples of proteins (or fragments thereof) that can be used in increase transcription include but are not limited to: transcriptional activators such as VP16, VP64, VP48, VP160, p65 subdomain (e.g., from NFkB), and activation domain of EDLL and/or TAL activation domain (e.g., for activity in plants); histone lysine methyltransferases such as SET1A, SET1B, MLL1 to 5, ASH1, SYMD2, NSD1, and the like; histone lysine demethylases such as JHDM2a/b, UTX, JMJD3, and the like; histone acetyltransferases such as GCN5, PCAF, CBP, p300, TAF1, TIP60/PLIP, MOZ/MYST3, MORF/MYST4, SRC1, ACTR, P160, CLOCK, and the like; and DNA demethylases such as Ten-Eleven Translocation (TET) dioxygenase 1 (TET1CD), TET1, DME, DML1, DML2, ROS1, and the like.

Examples of proteins (or fragments thereof) that can be used in decrease transcription include but are not limited to: transcriptional repressors such as the Kruppel associated box (KRAB or SKD); KOX1 repression domain; the Mad mSIN3 interaction domain (SID); the ERF repressor domain (ERD), the SRDX repression domain (e.g., for repression in plants), and the like; histone lysine methyltransferases such as Pr-SET7/8, SUV4-20H1, RIZ1, and the like; histone lysine demethylases such as JMJD2A/JHDM3A, JMJD2B, JMJD2C/GASC1, JMJD2D, JARID1A/RBP2, JARID1B/PLU-1, JARID1C/SMCX, JARID1D/SMCY, and the like; histone lysine deacetylases such as HDAC1, HDAC2, HDAC3, HDAC8, HDAC4, HDAC5, HDAC7, HDAC9, SIRT1, SIRT2, HDAC11, and the like; DNA methylases such as HhaI DNA m5c-methyltransferase (M.HhaI), DNA methyltransferase 1 (DNMT1), DNA methyltransferase 3a (DNMT3a), DNA methyltransferase 3b (DNMT3b), MET1, DRM3 (plants), ZMET2, CMT1, CMT2 (plants), and the like; and periphery recruitment elements such as Lamin A, Lamin B, and the like.

In some cases the fusion partner used in a CasJ fusion polypeptide has enzymatic activity that modifies the target nucleic acid (e.g., ssRNA, dsRNA, ssDNA, dsDNA). Examples of enzymatic activity that can be provided by the fusion partner include but are not limited to: nuclease activity such as that provided by a restriction enzyme (e.g., Fok1 nuclease), methyltransferase activity such as that provided by a methyltransferase (e.g., HhaI DNA m5c-methyltransferase, M.HhaI), DNA methyltransferase 1 (DNMT1), DNA methyltransferase 3a (DNMT3a), DNA methyltransferase 3b (DNMT3b), MET1, DRM3 (plants), ZMET2, CMT1, CMT2 (plants), and the like); demethylase activity such as that provided by a demethylase (e.g., Ten-Eleven Translocation (TET) dioxygenase 1 (TET1CD), TET1, DME, DML1, DML2, ROS 1, and the like), DNA repair activity, DNA damage activity, deamination activity such as that provided by a deaminase (e.g., a cytosine deaminase enzyme such as rat APOBEC1), dismutase activity, alkylation activity, depurination activity, oxidation activity, pyrimidine dimer forming activity, integrase activity such as that provided by an integrase and/or resolvase (e.g., Gin invertase such as the hyperactive mutant of the Gin invertase, GinH106Y; human immunodeficiency virus type 1 integrase (IN); Tn3 resolvase; and the like), transposase activity, recombinase activity such as that provided by a recombinase (e.g., catalytic domain of Gin recombinase), polymerase activity, ligase activity, helicase activity, photolyase activity, and glycosylase activity).

In some cases the fusion partner used in a CasJ fusion polypeptide has enzymatic activity that modifies a protein associated with the target nucleic acid (e.g., ssRNA, dsRNA, ssDNA, dsDNA) (e.g., a histone, an RNA binding protein, a DNA binding protein, and the like). Examples of enzymatic activity (that modifies a protein associated with a target nucleic acid) that can be provided by the fusion partner include but are not limited to: methyltransferase activity such as that provided by a histone methyltransferase (HMT) (e.g., suppressor of variegation 3-9 homolog 1 (SUV39H1, also known as KMTIA), euchromatic histone lysine methyltransferase 2 (G9A, also known as KMT1C and EHMT2), SUV39H2, ESET/SETDB 1, and the like, SET1A, SET1B, MLL1 to 5, ASH1, SYMD2, NSD1, DOT1L, Pr-SET7/8, SUV4-20H1, EZH2, RIZ1), demethylase activity such as that provided by a histone demethylase (e.g., Lysine Demethylase 1A (KDM1A also known as LSD1), JHDM2a/b, JMJD2A/JHDM3A, JMJD2B, JMJD2C/GASC1, JMJD2D, JARID1A/RBP2, JARID1B/PLU-1, JARID1C/SMCX, JARID1D/SMCY, UTX, JMJD3, and the like), acetyltransferase activity such as that provided by a histone acetylase transferase (e.g., catalytic core/fragment of the human acetyltransferase p300, GCN5, PCAF, CBP, TAF1, TIP60/PLIP, MOZ/MYST3, MORF/MYST4, HB01/MYST2, HMOF/MYST1, SRC1, ACTR, P160, CLOCK, and the like), deacetylase activity such as that provided by a histone deacetylase (e.g., HDAC1, HDAC2, HDAC3, HDAC8, HDAC4, HDAC5, HDAC7, HDAC9, SIRT1, SIRT2, HDAC11, and the like), kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, and demyristoylation activity.

An additional examples of a suitable fusion partners used in a CasJ fusion polypeptide are dihydrofolate reductase (DHFR) destabilization domain (e.g., to generate a chemically controllable chimeric CasJ protein or CasJ fusion polypeptide), and a chloroplast transit peptide. Suitable chloroplast transit peptides (CTPs) include, but are not limited to, CTPs having an amino acid sequence with at least 98%, 99%, or 100% sequence identity to SEQ ID NO: 3, 4, 5, 6, 7, 8, 9, 10, 11, 12, and 13.

In some case, a CasJ fusion polypeptide of the present disclosure comprises: a) a CasJ polypeptide of the present disclosure; and b) a chloroplast transit peptide. Thus, for example, a CRISPR-CasJ complex can be targeted to the chloroplast. In some cases, this targeting may be achieved by the presence of an N-terminal extension, called a chloroplast transit peptide (CTP) or plastid transit peptide. Chromosomal transgenes from bacterial sources must have a sequence encoding a CTP sequence fused to a sequence encoding an expressed polypeptide if the expressed polypeptide is to be compartmentalized in the plant plastid (e.g., chloroplast).

Accordingly, localization of an exogenous polypeptide to a chloroplast is often 1 accomplished by means of operably linking a polynucleotide sequence encoding a CTP sequence to the 5' region of a polynucleotide encoding the exogenous polypeptide. The CTP is removed in a processing step during translocation into the plastid. Processing efficiency may, however, be affected by the amino acid sequence of the CTP and nearby sequences at the amino terminus of the peptide. Other options for targeting to the chloroplast which have been described are the maize cab-m7 signal sequence (U.S. Pat. No. 7,022,896, WO 97/41228) a pea glutathione reductase signal sequence (WO 97/41228) and the CTP described in US2009029861.

The CasJ polypeptide disclosed herein can further comprise at least one plastid targeting signal peptide, at least one mitochondrial targeting signal peptide, or a signal peptide targeting the CasJ polypeptide to both plastids and mitochondria. Plastid, mitochondrial, and dual-targeting signal peptide localization signals are known in the art (see, e.g., Nassoury and Morse (2005) Biochim Biophys Acta 1743: 5-19; Kunze and Berger (2015) Front Physiol dx.doi.org/10.3389/fphys.2015.00259; Herrmann and Neupert (2003) IUBMB Life 55:219-225; Soll (2002) Curr Opin Plant Biol 5:529-535; Carrie and Small (2013) Biochim Biophys Acta 1833:253-259; Carrie et al. (2009) FEBS J 276:1187-1195; Silva-Filho (2003) Curr Opin Plant Biol 6:589-595; Peeters and Small (2001) Biochim Biophys Acta 1541:54-63; Murcha et al. (2014) J Exp Bot 65:6301-6335; Mackenzie (2005) Trends Cell Biol 15:548-554; Glaser et al. (1998) Plant Mol Biol 38:311-338). The plastid, mitochondrial, or dual-targeting signal peptide can be located at the N-terminus, the C-terminus, or in an internal location of the CasJ polypeptide.

In some cases, a CasJ fusion polypeptide of the present disclosure can comprise: a) a CasJ polypeptide of the present disclosure; and b) an endosomal escape peptide (EEP). In some cases, an endosomal escape polypeptide comprises the amino acid sequence of SEQ ID NO: 16 or SEQ ID NO: 17.

For examples of the above fusion partners (and more) used in the context of fusions with Cas9, Zinc Finger, and/or TALE proteins (for site specific target nucleic modification, modulation of transcription, and/or target protein modification, e.g., histone modification), see, e.g.: Nomura et al J Am Chem Soc. 2007 Jul. 18; 129(28):8676-7; Rivenbark et al., Epigenetics. 2012 April; 7(4):350-60; Nucleic Acids Res. 2016 Jul. 8; 44(12):5615-28; Gilbert et al, Cell. 2013 Jul. 18; 154(2):442-51; Kearns et al, Nat Methods. 2015 May; 12(5):401-3; Mendenhall et al, Nat Biotechnol. 2013 December; 31(12): 1133-6; Hilton et al., Nat Biotechnol. 2015 May; 33(5):510-7; Gordley et al., Proc Natl Acad Sci USA. 2009 Mar. 31; 106(13):5053-8; Akopian et al., Proc Natl Acad Sci USA. 2003 Jul. 22; 100(15):8688-91; Tan et al., J Virol. 2006 February; 80(4): 1939-48; Tan et al., Proc Natl Acad Sci USA. 2003 Oct. 14; 100(21): 11997-2002; Papworth et al., Proc Natl Acad Sci USA. 2003 Feb. 18; 100(4): 1621-6; Sanjana et al., Nat Protoc. 2012 Jan. 5; 7(1): 171-92; Beerli et al., Proc Natl Acad Sci USA. 1998 Dec. 8; 95(25): 14628-33; Snowden et al., Curr Biol. 2002 Dec. 23; 12(24):2159-66; Xu et.al., Cell Discov. 2016 May 3; 2: 16009; Komor et al., Nature. 2016 Apr. 20; 533(7603):420-4; Chaikind et al., Nucleic Acids Res. 2016 Aug. 11; Choudhury at. al., Oncotarget. 2016 Jun. 23; Du et al., Cold Spring Harb Protoc. 2016 Jan. 4; Pham et al, Methods Mol Biol. 2016; 1358:43-57; Balboa et al., Stem Cell Reports. 2015 Sep. 8; 5(3):448-59; Hara et al., Sci Rep. 2015 Jun. 9; 5: 11221; Piatek et al., Plant Biotechnol J. 2015 May; 13(4):578-89; Hu et al., Nucleic Acids Res. 2014 April; 42(7):4375-90; Cheng et al., Cell Res. 2013 October; 23(10): 1163-71; Cheng et al, Cell Res. 2013 October; 23(10):1 163-71; and Maeder et al., Nat Methods. 2013 October; 10(10):977-9.

Additional suitable heterologous polypeptides that can be used in a CasJ fusion polypeptide include, but are not limited to, a polypeptide that directly and/or indirectly provides for increased transcription and/or translation of a target nucleic acid (e.g., a transcription activator or a fragment thereof, a protein or fragment thereof that recruits a transcription activator, a small molecule/drug-responsive transcription and/or translation regulator, a translation-regulating protein, etc.). Non-limiting examples of heterologous polypeptides to accomplish increased or decreased transcription include transcription activator and transcription repressor domains. In some such cases, a chimeric CasJ polypeptide or CasJ fusion polypeptide is targeted by the guide nucleic acid (guide RNA) to a specific location (i.e., sequence) in the target nucleic acid and exerts locus-specific regulation such as blocking RNA polymerase binding to a promoter (which selectively inhibits transcription activator function), and/or modifying the local chromatin status (e.g., when a fusion sequence is used that modifies the target nucleic acid or modifies a polypeptide associated with the target nucleic acid). In some cases, the changes are transient (e.g., transcription repression or activation). In some cases, the changes are inheritable (e.g., when epigenetic modifications are made to the target nucleic acid or to proteins associated with the target nucleic acid, e.g., nucleosomal histones).

Non-limiting examples of heterologous polypeptides for use when targeting ssRNA target nucleic acids include but are not limited to: splicing factors (e.g., RS domains); protein translation components (e.g., translation initiation, elongation, and/or release factors; e.g., eIF4G); RNA methylases; RNA editing enzymes (e.g., RNA deaminases, e.g., adenosine deaminase acting on RNA (ADAR), including A to I and/or C to U editing enzymes); helicases; RNA-binding proteins; and the like. It is understood that a heterologous polypeptide can include the entire protein or in some cases can include a fragment of the protein (e.g., a functional domain).

The heterologous polypeptide of a subject chimeric CasJ polypeptide or CasJ fusion polypeptide can be any domain capable of interacting with ssRNA (which, for the purposes of this disclosure, includes intramolecular and/or intermolecular secondary structures, e.g., double-stranded RNA duplexes such as hairpins, stem-loops, etc.), whether transiently or irreversibly, directly or indirectly, including but not limited to an effector domain selected from the group comprising: Endonucleases (for example RNase III, the CRR22 DYW domain, Dicer, and PIN (PilT N-terminus) domains from proteins such as SMG5 and SMG6); proteins and protein domains responsible for stimulating RNA cleavage (for example CPSF, CstF, CFIm and CFIIm); Exonucleases (for example XRN-1 or Exonuclease T); Deadenylases (for example HNT3); proteins and protein domains responsible for nonsense mediated RNA decay (for example UPF1, UPF2, UPF3, UPF3b, RNP SI, Y14, DEK, REF2, and SRm160); proteins and protein domains responsible for stabilizing RNA (for example PABP); proteins and protein domains responsible for repressing translation (for example Ago2 and Ago4); proteins and protein domains responsible for stimulating translation (for example Staufen); proteins and protein domains responsible for (e.g., capable of) modulating translation (e.g., translation factors such as initiation factors, elongation factors, release factors, etc., e.g., eIF4G); proteins and protein domains responsible for polyadenylation of RNA (for example PAP1, GLD-2, and Star-PAP); proteins and protein domains responsible for polyuridinylation of RNA (for example CI Dl and terminal uridylate transferase); proteins and protein domains responsible for RNA localization (for example from IMP1, ZBP1, She2p, She3p, and Bicaudal-D); proteins and protein domains responsible for nuclear retention of RNA (for example Rrp6); proteins and protein domains responsible for nuclear export of RNA (for example TAP, NXF1, THO, TREX, REF, and Aly); proteins and protein domains responsible for repression of RNA splicing (for example PTB, Sam68, and hnRNP A1); proteins and protein domains responsible for stimulation of RNA splicing (for example Serine/Arginine-rich (SR) domains); proteins and protein domains responsible for reducing the efficiency of transcription (for example FUS (TLS)); and proteins and protein domains responsible for stimulating transcription (for example CDK7 and HIV Tat). Alternatively, the effector domain may be selected from the group comprising Endonucleases; proteins and protein domains capable of stimulating RNA cleavage; Exonucleases; Deadenylases; proteins and protein domains having nonsense mediated RNA decay activity; proteins and protein domains capable of stabilizing RNA; proteins and protein domains capable of repressing translation; proteins and protein domains capable of stimulating translation; proteins and protein domains capable of modulating translation (e.g., translation factors such as initiation factors, elongation factors, release factors, etc., e.g., eIF4G); proteins and protein domains capable of polyadenylation of RNA; proteins and protein domains capable of polyuridinylation of RNA; proteins and protein domains having RNA localization activity; proteins and protein domains capable of nuclear retention of RNA; proteins and protein domains having RNA nuclear export activity; proteins and protein domains capable of repression of RNA splicing; proteins and protein domains capable of stimulation of RNA splicing; proteins and protein domains capable of reducing the efficiency of transcription; and proteins and protein domains capable of stimulating transcription. Another suitable heterologous polypeptide is a PUF RNA-binding domain, which is described in more detail in WO2012068627, which is hereby incorporated by reference in its entirety.

Some RNA splicing factors that can be used (in whole or as fragments thereof) as heterologous polypeptides for a chimeric CasJ polypeptide or CasJ fusion polypeptide have modular organization, with separate sequence-specific RNA binding modules and splicing effector domains. For example, members of the Serine/Arginine-rich (SR) protein family contain N-terminal RNA recognition motifs (RRMs) that bind to exonic splicing enhancers (ESEs) in pre-mRNAs and C-terminal RS domains that promote exon inclusion. As another example, the hnRNP protein hnRNP A1 binds to exonic splicing silencers (ESSs) through its RRM domains and inhibits exon inclusion through a C-terminal Glycine-rich domain. Some splicing factors can regulate alternative use of splice site (ss) by binding to regulatory sequences between the two alternative sites. For example, ASF/SF2 can recognize ESEs and promote the use of intron proximal sites, whereas hnRNP A1 can bind to ESSs and shift splicing towards the use of intron distal sites. One application for such factors is to generate ESFs that modulate alternative splicing of endogenous genes, particularly disease associated genes. For example, Bcl-x pre-mRNA produces two splicing isoforms with two alternative 5' splice sites to encode proteins of opposite functions. The long splicing isoform Bcl-xL is a potent apoptosis inhibitor expressed in long-lived postmitotic cells and is up-regulated in many cancer cells, protecting cells against apoptotic signals. The short isoform Bcl-xS is a pro-apoptotic isoform and expressed at high levels in cells with a high turnover rate (e.g., developing lymphocytes). The ratio of the two Bcl-x splicing isoforms is regulated by multiple cc-elements that are located in either the core exon region or the exon extension region (i.e., between the two alternative 5' splice sites). For more examples, see WO2010075303, which is hereby incorporated by reference in its entirety.

Further suitable fusion partners or CasJ fusion peptide CasJ fusion polypeptide include, but are not limited to proteins (or fragments thereof) that are boundary elements (e.g., CTCF), proteins and fragments thereof that provide periphery recruitment (e.g., Lamin A, Lamin B, etc.), protein docking elements (e.g., FKBP/FRB, Pill/Abyl, etc.).

Examples of various additional suitable heterologous polypeptide (or fragments thereof) that can be adapted for use in a subject chimeric CasJ polypeptide or CasJ fusion polypeptide include, but are not limited to those described in the following applications (which publications are related to other CRISPR endonucleases such as Cas9, but the described fusion partners can also be used with CasJ instead): PCT patent applications: WO2010075303, WO2012068627, and WO2013155555, and can be found, for example, in U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

In some cases, a heterologous polypeptide (a fusion partner) or CasJ fusion polypeptide provides for subcellular localization, e.g., the heterologous polypeptide contains a subcellular localization sequence (e.g., a nuclear localization signal (NLS) for targeting to the nucleus, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an ER retention signal, and the like). In some embodiments, a CasJ fusion polypeptide does not include a NLS so that the protein is not targeted to the nucleus (which can be advantageous, e.g., when the target nucleic acid is an RNA that is present in the cytosol). In some embodiments, the heterologous polypeptide can provide a tag (e.g., the heterologous polypeptide is a detectable label) for ease of tracking and/or purification (e.g., a fluorescent protein, e.g., green fluorescent protein (GFP), YFP, RFP, CFP, mCherry, tdTomato, mScarlett, and the like; a histidine tag, e.g., a 6×His tag; a hemagglutinin (HA) tag; a FLAG tag; a Myc tag; and the like).

In some cases a CasJ protein (e.g., a wild type CasJ protein, a variant CasJ protein, a chimeric CasJ protein, CasJ fusion polypeptide, a dCasJ protein, a chimeric CasJ protein or CasJ fusion polypeptide where the CasJ portion has reduced nuclease activity—such as a dCasJ protein fused to a fusion partner, and the like) includes (is fused to) a nuclear localization signal (NLS) (e.g, in some cases 2 or more, 3 or more, 4 or more, or 5 or more NLSs). Thus, in some cases, a CasJ polypeptide includes one or more NLSs (e.g., 2 or more, 3 or more, 4 or more, or 5 or more NLSs). In some cases, one or more NLSs (2 or more, 3 or more, 4 or more, or 5 or more NLSs) are positioned at or near (e.g., within 50 amino acids of) the N-terminus and/or the C-terminus. In some cases, one or more NLSs (2 or more, 3 or more, 4 or more, or 5 or more NLSs) are positioned at or near (e.g., within 50 amino acids of) the N-terminus. In some cases, one or more NLSs (2 or more, 3 or more, 4 or more, or 5 or more NLSs) are positioned at or near (e.g., within 50 amino acids of) the C-terminus. In some cases, one or more NLSs (3 or more, 4 or more, or 5 or more NLSs) are positioned at or near (e.g., within 50 amino acids of) both the N-terminus and the C-terminus. In some cases, an NLS is positioned at the N-terminus and an NLS is positioned at the C-terminus.

In some cases a CasJ protein (e.g., a wild type CasJ protein, a variant CasJ protein, a chimeric CasJ protein, or CasJ fusion polypeptide, a dCasJ protein, a chimeric CasJ protein or CasJ fusion polypeptide where the CasJ portion has reduced nuclease activity—such as a dCasJ protein fused to a fusion partner, and the like) includes (is fused to) between 1 and 10 NLSs (e.g., 1-9, 1-8, 1-7, 1-6, 1-5, 2-10, 2-9, 2-8, 2-7, 2-6, or 2-5 NLSs). In some cases a CasJ protein (e.g., a wild type CasJ protein, a variant CasJ protein, a chimeric CasJ protein, a dCasJ protein, a chimeric CasJ protein or CasJ fusion polypeptide where the CasJ portion has reduced nuclease activity—such as a dCasJ protein fused to a fusion partner, and the like) includes (is fused to) between 2 and 5 NLSs (e.g., 2-4, or 2-3 NLSs).

Non-limiting examples of NLSs include an NLS sequence derived from: the NLS of the SV40 virus large T-antigen, having the amino acid sequence of SEQ ID NO: 57; the NLS from nucleoplasmin (e.g., the nucleoplasmin bipartite NLS with the sequence of SEQ ID NO: 18); the c-myc NLS having the amino acid sequence of SEQ ID NO: 19 or SEQ ID NO: 20; the hRNPA1 M9 NLS having the sequence of SEQ ID NO: 21; the sequence of SEQ ID NO: 22 of the IBB domain from importin-alpha; the sequences of SEQ ID NO: 23 or SEQ ID NO: 24 of the myoma T protein; the sequence of SEQ ID NO: 25 of human p53; the sequence of SEQ ID NO: 26 of mouse c-ab1 IV; the sequences of SEQ ID NO: 27 or SEQ ID NO: 28 of the influenza virus NS1; the sequence of SEQ ID NO: 29 of the Hepatitis virus delta antigen; the sequence of SEQ ID NO: 30 of the mouse Mx1 protein; the sequence of SEQ ID NO: 31 of the human poly(ADP-ribose) polymerase; and the sequence of SEQ ID NO: 32 of a steroid hormone receptor (e.g., human glucocorticoid receptor). In general, NLS (or multiple NLSs) are of sufficient strength to drive accumulation of the CasJ protein in a detectable amount in the nucleus of a eukaryotic cell. Detection of accumulation in the nucleus may be performed by any suitable technique. For example, a detectable marker may be fused to the CasJ protein such that location within a cell may be visualized. Cell nuclei may also be isolated from cells, the contents of which may then be analyzed by any suitable process for detecting protein, such as immunohistochemistry, Western blot, or enzyme activity assay. Accumulation in the nucleus may also be determined indirectly.

In some cases, a CasJ fusion polypeptide includes a "Protein Transduction Domain" or PTD (also known as a CPP—cell penetrating peptide), which refers to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD is covalently linked to the amino terminus a polypeptide (e.g., linked to a wild type CasJ to generate a fusion protein, or linked to a variant CasJ protein such as a dCasJ, nickase CasJ, or chimeric CasJ protein or CasJ fusion polypeptide to generate a fusion protein). In some embodiments, a PTD is covalently linked to the carboxyl terminus of a polypeptide (e.g., linked to a wild type CasJ to generate a fusion protein, or linked to a variant CasJ protein such as a dCasJ, nickase CasJ, or chimeric CasJ protein or CasJ fusion polypeptide to generate a fusion protein). In some cases, the PTD is inserted internally in the CasJ fusion polypeptide (i.e., is not at the N- or C-terminus of the CasJ fusion polypeptide) at a suitable insertion site. In some cases, a subject CasJ fusion polypeptide includes (is conjugated to, is fused to) one or more PTDs (e.g., two or more, three or more, four or more PTDs). In some cases a PTD includes a nuclear localization signal (NLS) (e.g, in some cases 2 or more, 3 or more, 4 or more, or 5 or more NLSs). Thus, in some cases, a CasJ fusion polypeptide includes one or more NLSs (e.g., 2 or more, 3 or more, 4 or more, or 5 or more NLSs). In some embodiments, a PTD is covalently linked to a nucleic acid (e.g., a CasJ guide nucleic acid, a polynucleotide encoding a CasJ guide nucleic acid, a polynucleotide encoding a CasJ fusion polypeptide, a donor polynucleotide, etc.). Examples of PTDs include but are not limited to a minimal undecapeptide protein transduction domain (corresponding to residues 47-57 of HIV-1 TAT comprising YGRKKRRQRRR (SEQ ID NO: 33); a polyarginine sequence comprising a number of arginines sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); an *Drosophila* Antennapedia protein transduction domain (Noguchi et al. (2003) Diabetes 52(7): 1732-1737); a truncated human calcitonin peptide (Trehin et al. (2004) Pharm. Research 21: 1248-1256); polylysine (Wender et al. (2000) Proc. Natl. Acad. Sci. USA 97: 13003-13008); RRQRRTSKLMKR (SEQ ID NO: 34); Transportan (e.g., SEQ ID NO: 35, SEQ ID NO: 36, or SEQ ID NO: 37). Exemplary PTDs include but are not limited to, SEQ ID NO: 38, SEQ ID NO: 39; an arginine homopolymer of from 3 arginine residues to 50 arginine residues; Exemplary PTD domain amino acid sequences include, but are not limited to, any of the following: SEQ ID NO: 40; SEQ ID NO: 41; SEQ ID NO: 42; SEQ ID NO: 43; and SEQ ID NO: 44. In some embodiments, the PTD is an activatable CPP (ACPP) (Aguilera et al. (2009) Integr Biol (Camb) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

In some embodiments, a subject CasJ protein can fused to a fusion partner via a linker polypeptide (e.g., one or more linker polypeptides). The linker polypeptide may have any of a variety of amino acid sequences. Proteins can be joined by a spacer peptide, generally of a flexible nature, although other chemical linkages are not excluded. Suitable linkers include polypeptides of between 4 amino acids and 40 amino acids in length, or between 4 amino acids and 25 amino acids in length. These linkers can be produced by using synthetic, linker-encoding oligonucleotides to couple the proteins, or can be encoded by a nucleic acid sequence encoding the fusion protein. Peptide linkers with a degree of flexibility can be used. The linking peptides may have virtually any amino acid sequence, bearing in mind that the preferred linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use.

Examples of linker polypeptides include glycine polymers $(G)_n$, glycine-serine polymers (including, for example, $(GS)_n$, $GSGGS_n$ (SEQ ID NO: 45), $GGSGGS_n$ (SEQ ID NO: 46), and $GGGS_n$ (SEQ ID NO: 47), where n is an integer of at least one), glycine-alanine polymers, alanine-serine polymers. Exemplary linkers can comprise amino acid sequences including, but not limited to, the amino acid sequences of SEQ ID NO: 48, SEQ ID NO: 49, SEQ ID NO: 50, SEQ ID NO: 51, SEQ ID NO: 52, SEQ ID NO: 53, and the like. The ordinarily skilled artisan will recognize that design of a peptide conjugated to any desired element can include linkers that are all or partially flexible, such that the linker can include a flexible linker as well as one or more portions that confer less flexible structure.

In some cases, a CasJ polypeptide or CasJ fusion polypeptide of the present disclosure comprises a detectable label. Suitable detectable labels and/or moieties that can provide a detectable signal can include, but are not limited to, an enzyme, a radioisotope, a member of a specific binding pair; a fluorophore; a fluorescent protein; a quantum dot; and the like.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dEGFP), destabilised ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, Renilla GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mScarlett, mTangerine, mStrawberry, mCherry, mGrape1, mRaspberry, mGrape2, mPlum (Shaner et al. (2005) Nat. Methods 2:905-909), and the like. Any of a variety of fluorescent and colored proteins from Anthozoan species, as described in, e.g., Matz et al. (1999) Nature Biotechnol. 17:969-973, is suitable for use.

Suitable enzymes include, but are not limited to, horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase, glucose oxidase (GO), and the like A CasJ protein binds to target DNA at a target sequence defined by the region of complementarity between the DNA-targeting RNA and the target DNA. As is the case for many CRISPR endonucleases, site-specific binding (and/or cleavage) of a double stranded target DNA occurs at locations determined by both (i) base-pairing complementarity between the guide RNA and the target DNA; and (ii) a short motif, referred to as the protospacer adjacent motif (PAM), in the target DNA.

In some embodiments, the PAM for a CasJ protein is immediately 5' of the target sequence of the non-complementary strand of the target DNA (the complementary strand hybridizes to the guide sequence of the guide RNA while the non-complementary strand does not directly hybridize with the guide RNA and is the reverse complement of the complementary strand). In some embodiments (e.g., when CasJ as described herein is used), the PAM consensus sequence of the non-complementary strand is T-rich. Examples of PAM sequences include, but are not limited to, TTN, CTN, TCN, CCN, TTTN, TCTN, TTCN, CTTN, ATTN, TCCN, TTGN, GTTN, CCCN, CCTN, TTAN, TCGN, CTCN, ACTN, GCTN, TCAN, GCCN, and CCGN (wherein N is defined as any nucleotide).

In some cases, different CasJ proteins (e.g., CasJ proteins from various species) may be advantageous to use in the various provided methods in order to capitalize on various enzymatic characteristics of the different CasJ proteins (e.g., for different PAM sequence preferences; for increased or decreased enzymatic activity; for an increased or decreased level of cellular toxicity; to change the balance between NHEJ, homology-directed repair, single strand breaks, double strand breaks, etc.; to take advantage of a short total sequence; and the like). CasJ proteins may require different PAM sequences in the target DNA. Thus, for a particular CasJ protein of choice, the PAM sequence requirement may be different than the T-rich sequence described above. Various methods (including in silico and/or wet lab methods) for identification of the appropriate PAM sequence are known in the art and are routine, and any convenient method can be used. A PAM sequence can be identified using a PAM depletion assay.

A nucleic acid molecule that binds to a CasJ protein, forming a ribonucleoprotein complex (RNP), and targets the complex to a specific location within a target nucleic acid (e.g., a target DNA) is referred to herein as a "CasJ guide RNA" or simply as a "guide RNA." It is to be understood that in some cases, a hybrid DNA/RNA can be made such that a CasJ guide RNA includes DNA bases in addition to RNA bases, but the term "CasJ guide RNA" is still used to encompass such a molecule herein.

A CasJ guide RNA can be said to include two segments, a targeting segment and a protein-binding segment. The targeting segment of a CasJ guide RNA includes a nucleotide sequence (a guide sequence) that is complementary to (and therefore hybridizes with) a specific sequence (a target site) within a target nucleic acid (e.g., a target ssRNA, a target ssDNA, the complementary strand of a double stranded target DNA, etc.). Site-specific binding and/or cleavage of a target nucleic acid (e.g., genomic DNA) can occur at locations (e.g., target sequence of a target locus) determined by base-pairing complementarity between the CasJ guide RNA (the guide sequence of the CasJ guide RNA) and the target nucleic acid.

The protein-binding segment (or "protein-binding sequence") interacts with (binds to) a CasJ polypeptide.

In some cases the protein-binding segment is made up of a short sequence of 17-20 nucleotides, such as a sequence of 18 or 19 nucleotides. This protein binding segment forms a double-stranded RNA duplex of five paired residues in length. The 5' terminus has about three residues upstream from the first RNA duplexed residue. A stem structure of 4-5 residues separates the double stranded regions. A protein binding segment can be made up, for example, of residues 19-36 of an RNA encoded by SEQ ID NO: 2 (i.e., an RNA encoded by SEQ ID NO: 15).

In some cases the protein-binding segment of a subject CasJ guide RNA includes two complementary stretches of nucleotides that hybridize to one another to form a double stranded RNA duplex (dsRNA duplex).

A CasJ guide RNA and a CasJ protein, e.g., a fusion CasJ polypeptide, form a complex (e.g., bind via non-covalent interactions). The CasJ guide RNA provides target specificity to the complex by including a targeting segment, which includes a guide sequence (a nucleotide sequence that is complementary to a sequence of a target nucleic acid). The CasJ protein of the complex provides the site-specific activity (e.g., cleavage activity provided by the CasJ protein or CasJ fusion polypeptide and/or an activity provided by the fusion partner in the case of a chimeric CasJ protein or CasJ fusion polypeptide). In other words, the CasJ protein is guided to a target nucleic acid sequence (e.g., a target sequence) by virtue of its association with the CasJ guide RNA.

The "guide sequence" also referred to as the "targeting sequence" of a CasJ guide RNA can be made so that the CasJ guide RNA can target a CasJ protein (e.g., a naturally-occurring CasJ protein, a fusion CasJ polypeptide (chimeric CasJ), and the like) to any desired sequence of any desired target nucleic acid, with the exception (e.g., as described herein) that the PAM sequence can be taken into account. Thus, for example, a CasJ guide RNA can have a guide sequence with complementarity to (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

In some embodiments a subject CasJ guide RNA can also be said to include an "activator" and a "targeter" (e.g., an "activator-RNA" and a "targeter-RNA," respectively). When the "activator" and a "targeter" are two separate molecules the guide RNA is referred to herein as a "dual guide RNA", a "dgRNA," a "double-molecule guide RNA", or a "two-molecule guide RNA." (e.g., a "CasJ dual guide RNA"). In some embodiments, the activator and targeter are covalently linked to one another (e.g., via intervening nucleotides) and the guide RNA is referred to herein as a "single guide RNA", an "sgRNA," a "single-molecule guide RNA," or a "one-molecule guide RNA" (e.g., a "CasJ single guide RNA"). Thus, a subject CasJ single guide RNA comprises a targeter (e.g., targeter-RNA) and an activator (e.g., activator-RNA) that are linked to one another (e.g., by intervening nucleotides), and may hybridize to one another to form the double stranded RNA duplex (dsRNA duplex) of the protein-binding segment of the guide RNA, thus resulting in a stem-loop structure. Thus, the targeter and the activator each have a duplex-forming segment, where the duplex forming segment of the targeter and the duplex-forming segment of the activator have complementarity with one another and hybridize to one another.

In some embodiments, the linker of a CasJ single guide RNA is a stretch of nucleotides. In some cases, the targeter and activator of a CasJ single guide RNA are linked to one another by intervening nucleotides and the linker can have a length of from 3 to 20 nucleotides (nt) (e.g., from 3 to 15, 3 to 12, 3 to 10, 3 to 8, 3 to 6, 3 to 5, 3 to 4, 4 to 20, 4 to 15, 4 to 12, 4 to 10, 4 to 8, 4 to 6, or 4 to 5 nt). In some embodiments, the linker of a CasJ single guide RNA can have a length of from 3 to 100 nucleotides (nt) (e.g., from 3 to 80, 3 to 50, 3 to 30, 3 to 25, 3 to 20, 3 to 15, 3 to 12, 3 to 10, 3 to 8, 3 to 6, 3 to 5, 3 to 4, 4 to 100, 4 to 80, 4 to 50, 4 to 30, 4 to 25, 4 to 20, 4 to 15, 4 to 12, 4 to 10, 4 to 8, 4 to 6, or 4 to 5 nt). In some embodiments, the linker of a CasJ single guide RNA can have a length of from 3 to 10 nucleotides (nt) (e.g., from 3 to 9, 3 to 8, 3 to 7, 3 to 6, 3 to 5, 3 to 4, 4 to 10, 4 to 9, 4 to 8, 4 to 7, 4 to 6, or 4 to 5 nt).

The targeting segment of a subject CasJ guide RNA includes a guide sequence (i.e., a targeting sequence), which is a nucleotide sequence that is complementary to a sequence (a target site) in a target nucleic acid. In other words, the targeting segment of a CasJ guide RNA can interact with a target nucleic acid (e.g., double stranded DNA (dsDNA), single stranded DNA (ssDNA), single stranded RNA (ssRNA), or double stranded RNA (dsRNA)) in a sequence-specific manner via hybridization (i.e., base pairing). The guide sequence of a CasJ guide RNA can be modified (e.g., by genetic engineering)/designed to hybridize to any desired target sequence (e.g., while taking the PAM into account, e.g., when targeting a dsDNA target) within a target nucleic acid (e.g., a eukaryotic target nucleic acid such as genomic DNA).

In some embodiments, the percent complementarity between the guide sequence and the target site of the target nucleic acid is 60% or more (e.g., 65% or more, 70% or more, 75% or more, 80% or more, 85% or more, 90% or more, 95% or more, 97% or more, 98% or more, 99% or more, or 100%). In some cases, the percent complementarity between the guide sequence and the target site of the target nucleic acid is 80% or more (e.g., 85% or more, 90% or more, 95% or more, 97% or more, 98% or more, 99% or more, or 100%). In some cases, the percent complementarity between the guide sequence and the target site of the target nucleic acid is 90% or more (e.g., 95% or more, 97% or more, 98% or more, 99% or more, or 100%). In some cases, the percent complementarity between the guide sequence and the target site of the target nucleic acid is 100%.

In some cases, the percent complementarity between the guide sequence and the target site of the target nucleic acid is 100% over the seven contiguous 3'-most nucleotides of the target site of the target nucleic acid.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 19 or more (e.g., 20 or more, 21 or more, 22 or more, 23 or more, 24 or more, 25 or more) contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 19 or more (e.g., 20 or more, 21 or more, 22 or more, 23 or more, 24 or more, 25 or more) contiguous nucleotides. In some cases, the percent complementarity between the guide sequence and the target site of the target nucleic acid is 90% or more (e.g., 95% or more, 97% or more, 98% or more, 99% or more, or 100%) over 19 or more (e.g., 20 or more, 21 or more, 22 or more, 23 or more, 24 or more, 25 or more) contiguous nucleotides. In some cases, the percent complementarity between the guide sequence and the target site of the target nucleic acid is 100% over 19 or more (e.g., 20 or more, 21 or more, 22 or more, 23 or more, 24 or more, 25 or more) contiguous nucleotides.

In some cases, the guide sequence has a length in a range of from 19-30 nucleotides (e.g., from 19-25, 19-22, 19-20, 20-30, 20-25, or 20-22 nt). In some cases, the guide sequence has a length in a range of from 19-25 nucleotides (e.g., from 19-22, 19-20, 20-25, 20-25, or 20-22 nt). In some cases, the guide sequence has a length of 19 or more nt (e.g., 20 or more, 21 or more, or 22 or more nt; 19 nt, 20 nt, 21 nt, 22 nt, 23 nt, 24 nt, 25 nt, etc.). In some cases the guide sequence has a length of 17 nt. In some cases the guide sequence has a length of 18 nt. In some cases the guide sequence has a length of 19 nt. In some cases the guide sequence has a length of 20 nt. In some cases the guide sequence has a length of 21 nt. In some cases the guide sequence has a length of 22 nt. In some cases the guide sequence has a length of 23 nt.

The protein-binding segment of a subject CasJ guide RNA interacts with a CasJ protein. The CasJ guide RNA guides the bound CasJ protein to a specific nucleotide sequence within target nucleic acid via the above mentioned guide sequence. In some embodiments, the protein-binding segment of a CasJ guide RNA comprises two stretches of nucleotides (the duplex-forming segment of the activator and the duplex-forming segment of the targeter) that are complementary to one another and hybridize to form a double stranded RNA duplex (dsRNA duplex). Thus, the protein-binding segment includes a dsRNA duplex.

The duplex region of a subject CasJ guide RNA (in dual guide or single guide RNA format) can include one or more (1, 2, 3, 4, 5, etc) mutations relative to a naturally-occurring duplex region. For example, in some cases a base pair can be maintained while the nucleotides contributing to the base pair from each segment (targeter and activator) can be different. In some cases, the duplex region of a subject CasJ guide RNA includes more paired bases, less paired bases, a smaller bulge, a larger bulge, fewer bulges, more bulges, or any convenient combination thereof, as compared to a naturally-occurring duplex region (of a naturally-occurring CasJ guide RNA).

In some cases, the activator (e.g., activator-RNA) of a subject CasJ guide RNA (in dual or single guide RNA format) includes at least two internal RNA duplexes (i.e., two internal hairpins in addition to the activator/targeter dsRNA). The internal RNA duplexes (hairpins) of the activator can be positioned 5' of the activator/targeter dsRNA duplex. In some cases, the activator includes one hairpin positioned 5' of the activator/targeter dsRNA duplex. In some cases, the activator includes two hairpins positioned 5' of the activator/targeter dsRNA duplex. In some cases, the activator includes three hairpins positioned 5' of the activator/targeter dsRNA duplex. In some cases, the activator includes two or more hairpins (e.g., 3 or more or 4 or more hairpins) positioned 5' of the activator/targeter dsRNA duplex. In some cases, the activator includes 2 to 5 hairpins (e.g., 2 to 4, or 2 to 3 hairpins) positioned 5' of the activator/targeter dsRNA duplex.

In some cases, the activator-RNA (e.g., in dual or single guide RNA format) comprises at least 2 nucleotides (nt) (e.g., at least 3 or at least 4 nt) 5' of the 5'-most hairpin stem. In some cases, the activator-RNA (e.g., in dual or single guide RNA format) comprises at least 4 nt 5' of the 5'-most hairpin stem.

In some cases, the activator-RNA (e.g., in dual or single guide format) includes 45 or more nucleotides (nt) (e.g., 46 or more, 47 or more, 48 or more, 49 or more, 50 or more, 51 or more, 52 or more, 53 or more, 54 or more, or 55 or more nt) 5' of the dsRNA duplex formed between the activator and the targeter (the activator/targeter dsRNA duplex). In some cases, the activator is truncated at the 5' end relative to a naturally-occurring CasJ activator. In some cases, the activator is extended at the 5' end relative to a naturally-occurring CasJ activator.

In some cases, the term "activator" or "activator RNA" is used herein to mean a tracrRNA-like molecule (tracrRNA: "trans-acting CRISPR RNA") of a CasJ dual guide RNA (and therefore of a CasJ single guide RNA when the "activator" and the "targeter" are linked together by, e.g., intervening nucleotides). Thus, for example, a CasJ guide RNA (dgRNA or sgRNA) comprises an activator sequence (e.g., a tracrRNA sequence). A tracr molecule (a tracrRNA) is a naturally existing molecule that hybridizes with a CRISPR RNA molecule (a crRNA) to form a CasJ dual guide RNA. A tracrRNA of the CasJ locus is shown as SEQ ID NO: 14 and SEQ ID NO: 59. The term "activator" is used herein to encompass naturally-occurring tracrRNAs, but also to encompass tracrRNAs with modifications (e.g., truncations, extensions, sequence variations, base modifications, backbone modifications, linkage modifications, etc.) where the activator retains at least one function of a tracrRNA (e.g., contributes to the dsRNA duplex to which CasJ protein binds). In some cases the activator provides one or more stem loops that can interact with CasJ protein. An activator can be referred to as having a tracr sequence (tracrRNA sequence) and in some cases is a tracrRNA, but the term "activator" is not limited to naturally-occurring tracrRNAs.

In some cases (e.g., in some cases where the guide RNA is in single guide format), the activator-RNA is truncated (shorter) relative to the corresponding wild type tracrRNA. In some cases (e.g., in some cases where the guide RNA is in single guide format) the activator-RNA is not truncated (shorter) relative to the corresponding wild type tracrRNA. In some cases (e.g., in some cases where the guide RNA is in single guide format) the activator-RNA has a length that is greater than 50 nt (e.g., greater than 55 nt, greater than 60 nt, greater than 65 nt, greater than 70 nt, greater than 75 nt, greater than 80 nt). In some cases (e.g., in some cases where the guide RNA is in single guide format) the activator-RNA has a length that is greater than 80 nt. In some cases (e.g., in some cases where the guide RNA is in single guide format) the activator-RNA has a length in a range of from 51 to 90 nt (e.g., from 51-85, 51-84, 55-90, 55-85, 55-84, 60-90, 60-85, 60-84, 65-90, 65-85, 65-84, 70-90, 70-85, 70-84, 75-90, 75-85, 75-84, 80-90, 80-85, or 80-84 nt). In some cases (e.g., in some cases where the guide RNA is in single guide format) the activator-RNA has a length in a range of from 80-90 nt.

The term "targeter" or "targeter RNA" is used herein to refer to a crRNA-like molecule (crRNA: "CRISPR RNA" or CR) of a CasJ dual guide RNA (and therefore of a CasJ single guide RNA when the "activator" and the "targeter" are linked together, e.g., by intervening nucleotides). Thus, for example, a CasJ guide RNA (dgRNA or sgRNA) comprises a guide sequences and a duplex-forming segment (e.g., a duplex forming segment of a crRNA, which can also be referred to as a crRNA repeat). Because the sequence of a targeting segment (the segment that hybridizes with a target sequence of a target nucleic acid) of a targeter is modified by a user to hybridize with a desired target nucleic acid, the sequence of a targeter will often be a non-naturally-occurring sequence. However, the duplex-forming segment of a targeter (described in more detail herein), which hybridizes with the duplex-forming segment of an activator, can include a naturally-occurring sequence (e.g., can include the sequence of a duplex-forming segment of a naturally-occurring crRNA, which can also be referred to as a crRNA repeat). Thus, the term targeter is used herein to distinguish from naturally occurring crRNAs, despite the fact that part of a targeter (e.g., the duplex-forming segment) often includes a naturally-occurring sequence from a crRNA. However, the term "targeter" encompasses naturally-occurring crRNAs. As noted above, a targeter comprises both the guide sequence of the CasJ guide RNA and a stretch (a "duplex-forming segment") of nucleotides that forms one half of the dsRNA duplex of the protein-binding segment of the CasJ guide RNA. A corresponding tracrRNA-like molecule (activator) comprises a stretch of nucleotides (a duplex-forming segment) that forms the other half of the dsRNA duplex of the protein-binding segment of the CasJ guide RNA. In other words, a stretch of nucleotides of the targeter is complementary to and hybridizes with a stretch of nucleotides of the activator to form the dsRNA duplex of the protein-binding segment of a CasJ guide RNA. As such, each targeter can be said to have a corresponding activator (which has a region that hybridizes with the targeter). The targeter molecule additionally provides the guide sequence. Thus, a targeter and an activator (as a corresponding pair) hybridize to form a CasJ guide RNA. The particular sequence of a given naturally-occurring crRNA or tracrRNA molecule can be characteristic of the species in which the RNA molecules are found.

The present disclosure provides an engineered, non-naturally-occurring CasJ system. In certain embodiments, a CasJ system of the present disclosure can comprise: a) a CasJ polypeptide of the present disclosure and a CasJ guide RNA; b) a CasJ polypeptide of the present disclosure, a CasJ guide RNA, and a donor template nucleic acid; c) a CasJ fusion polypeptide of the present disclosure and a CasJ guide RNA; d) a CasJ fusion polypeptide of the present disclosure, a CasJ guide RNA, and a donor template nucleic acid; e) an mRNA encoding a CasJ polypeptide of the present disclosure; and a CasJ guide RNA; f) an mRNA encoding a CasJ polypeptide of the present disclosure, a CasJ guide RNA, and a donor template nucleic acid; g) an mRNA encoding a CasJ fusion polypeptide of the present disclosure; and a CasJ guide RNA; h) an mRNA encoding a CasJ fusion polypeptide of the present disclosure, a CasJ guide RNA, and a donor template nucleic acid; i) a recombinant expression vector comprising a nucleotide sequence encoding a CasJ polypeptide of the present disclosure and a nucleotide sequence encoding a CasJ guide RNA; j) a recombinant expression vector comprising a nucleotide sequence encoding a CasJ polypeptide of the present disclosure, a nucleotide sequence encoding a CasJ guide RNA, and a nucleotide sequence encoding a donor template nucleic acid; k) a recombinant expression vector comprising a nucleotide sequence encoding a CasJ fusion polypeptide of the present disclosure and a nucleotide sequence encoding a CasJ guide RNA; 1) a recombinant expression vector comprising a nucleotide sequence encoding a CasJ fusion polypeptide of the present disclosure, a nucleotide sequence encoding a CasJ guide RNA, and a nucleotide sequence encoding a donor template nucleic acid; m) a first recombinant expression vector comprising a nucleotide sequence encoding a CasJ polypeptide of the present disclosure, and a second recombinant expression vector comprising a nucleotide sequence encoding a CasJ guide RNA; n) a first recombinant expression vector comprising a nucleotide sequence encoding a CasJ polypeptide of the present disclosure, and a second recombinant expression vector comprising a nucleotide sequence encoding a CasJ guide RNA; and a donor template nucleic acid; o) a first recombinant expression vector comprising a nucleotide sequence encoding a CasJ fusion polypeptide of the present disclosure, and a second recombinant expression vector comprising a nucleotide sequence encoding a CasJ guide RNA; p) a first recombinant expression vector comprising a nucleotide sequence encoding a CasJ fusion polypeptide of the present disclosure, and a second recombinant expression vector comprising a nucleotide sequence encoding a CasJ guide RNA; and a donor template nucleic acid; q) a recombinant expression vector comprising a nucleotide sequence encoding a CasJ polypeptide of the present disclosure, a nucleotide sequence encoding a first CasJ guide RNA, and a nucleotide sequence encoding a second CasJ guide RNA; or r) a recombinant expression vector comprising a nucleotide sequence encoding a CasJ fusion polypeptide of the present disclosure, a nucleotide sequence encoding a first CasJ guide RNA, and a nucleotide sequence encoding a second CasJ guide RNA; or some variation of one of (a) through (r).

The present disclosure provides one or more nucleic acids comprising one or more of: a donor polynucleotide sequence, a nucleotide sequence encoding a CasJ polypeptide (e.g., a wild type CasJ protein, a nickase CasJ protein, a dCasJ protein, chimeric CasJ protein, CasJ fusion polypeptide, and the like), a CasJ guide RNA, and a nucleotide sequence encoding a CasJ guide RNA (which can include two separate nucleotide sequences in the case of dual guide RNA format or which can include a single nucleotide sequence in the case of single guide RNA format). The present disclosure provides a nucleic acid comprising a nucleotide sequence encoding a CasJ fusion polypeptide. The present disclosure provides a recombinant expression vector that comprises a nucleotide sequence encoding a CasJ polypeptide. The present disclosure provides a recombinant expression vector that comprises a nucleotide sequence encoding a CasJ fusion polypeptide. The present disclosure provides a recombinant expression vector that comprises: a) a nucleotide sequence encoding a CasJ polypeptide; and b) a nucleotide sequence encoding a CasJ guide RNA(s). The present disclosure provides a recombinant expression vector that comprises: a) a nucleotide sequence encoding a CasJ fusion polypeptide; and b) a nucleotide sequence encoding a CasJ guide RNA(s). In some cases, the nucleotide sequence encoding the CasJ protein and/or the nucleotide sequence encoding the CasJ guide RNA is operably linked to a promoter that is operable in a cell type of choice (e.g., a prokaryotic cell, a eukaryotic cell, a plant cell, an animal cell, a mammalian cell, a primate cell, a rodent cell, a human cell, etc.).

In some cases, a nucleotide sequence encoding a CasJ polypeptide of the present disclosure is codon optimized. This type of optimization can entail a mutation of a CasJ-encoding nucleotide sequence to mimic the codon preferences of the intended host organism or cell while encoding the same protein. Thus, the codons can be changed, but the encoded protein remains unchanged. For example, if the intended target cell was a human cell, a human codon-optimized CasJ-encoding nucleotide sequence could be used. As another non-limiting example, if the intended host cell were a mouse cell, then a mouse codon-optimized CasJ-encoding nucleotide sequence could be generated. As another non-limiting example, if the intended host cell were a plant cell, then a plant codon-optimized CasJ-encoding nucleotide sequence could be generated. As another non-limiting example, if the intended host cell were an insect cell, then an insect codon-optimized CasJ-encoding nucleotide sequence could be generated.

The present disclosure provides one or more recombinant expression vectors that include (in different recombinant expression vectors in some cases, and in the same recombinant expression vector in some cases): (i) a nucleotide sequence of a donor template nucleic acid (where the donor template comprises a nucleotide sequence having homology to a target sequence of a target nucleic acid (e.g., a target genome)); (ii) a nucleotide sequence that encodes a CasJ guide RNA that hybridizes to a target sequence of the target locus of the targeted genome (e.g., a single or dual guide RNA) (e.g., operably linked to a promoter that is operable in a target cell such as a eukaryotic cell); and (iii) a nucleotide sequence encoding a CasJ protein (e.g., operably linked to a promoter that is operable in a target cell such as a eukaryotic cell). The present disclosure provides one or more recombinant expression vectors that include (in different recombinant expression vectors in some cases, and in the same recombinant expression vector in some cases): (i) a nucleotide sequence of a donor template nucleic acid (where the donor template comprises a nucleotide sequence having homology to a target sequence of a target nucleic acid (e.g., a target genome)); and (ii) a nucleotide sequence that encodes a CasJ guide RNA that hybridizes to a target sequence of the target locus of the targeted genome (e.g., a single or dual guide RNA) (e.g., operably linked to a promoter that is operable in a target cell such as a eukaryotic cell). The present disclosure provides one or more recombinant expression vectors that include (in different recombinant expression vectors in some cases, and in the same recombinant expression vector in some cases): (i) a nucleotide sequence that encodes a CasJ guide RNA that hybridizes to a target sequence of the target locus of the targeted genome (e.g., a single or dual guide RNA) (e.g., operably linked to a promoter that is operable in a target cell such as a eukaryotic cell); and (ii) a nucleotide sequence encoding a CasJ protein (e.g., operably linked to a promoter that is operable in a target cell such as a eukaryotic cell).

Suitable expression vectors include viral expression vectors (e.g., viral vectors based on vaccinia virus; poliovirus; adenovirus (see, e.g., Li et al., Invest Opthalmol Vis Sci 35:2543 2549, 1994; Borras et al, Gene Ther 6:515 524, 1999; Li and Davidson, PNAS 92:7700 7704, 1995; Sakamoto et al., H Gene Ther 5: 1088 1097, 1999; WO 94/12649, WO 93/03769; WO 93/19191; WO 94/28938; WO 95/11984 and WO 95/00655); adeno-associated virus (AAV) (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90: 10613-10617); SV40; herpes simplex virus; human immunodeficiency virus (see, e.g., Miyoshi et al., PNAS 94: 10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, a recombinant expression vector of the present disclosure is a recombinant adeno-associated virus (AAV) vector. In some cases, a recombinant expression vector of the present disclosure is a recombinant lentivirus vector. In some cases, a recombinant expression vector of the present disclosure is a recombinant retroviral vector.

Depending on the host/vector system utilized, any of a number of suitable transcription and translation control elements, including constitutive and inducible promoters, transcription enhancer elements, transcription terminators, etc. may be used in the expression vector.

In some embodiments, a nucleotide sequence encoding a CasJ guide RNA is operably linked to a control element, e.g., a transcriptional control element, such as a promoter. In some embodiments, a nucleotide sequence encoding a CasJ protein or a CasJ fusion polypeptide is operably linked to a control element, e.g., a transcriptional control element, such as a promoter.

The transcriptional control element can be a promoter. In some cases, the promoter is a constitutively active promoter. In some cases, the promoter is a regulatable promoter. In some cases, the promoter is an inducible promoter. In some cases, the promoter is a tissue-specific promoter. In some cases, the promoter is a cell type-specific promoter. In some cases, the transcriptional control element (e.g., the promoter) is functional in a targeted cell type or targeted cell population. For example, in some cases, the transcriptional control element can be functional in eukaryotic cells, e.g., hematopoietic stem cells (e.g., mobilized peripheral blood (mPB) CD34(+) cell, bone marrow (BM) CD34(+) cell, etc.).

Nonlimiting examples of eukaryotic promoters (promoters functional in a eukaryotic cell) include EF1a, those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g., 6×His tag, hemagglutinin tag, fluorescent protein, etc.) that can be fused to the CasJ protein, thus resulting in a chimeric CasJ polypeptide or CasJ fusion polypeptide.

In some embodiments, a nucleotide sequence encoding a CasJ guide RNA and/or a CasJ fusion polypeptide is operably linked to an inducible promoter. In some embodiments, a nucleotide sequence encoding a CasJ guide RNA and/or a CasJ fusion protein is operably linked to a constitutive promoter.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (e.g., transcriptional control element, enhancer, etc.)(e.g., tissue specific promoter, cell type specific promoter, etc.), and it may be a temporally restricted promoter (e.g., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human HI promoter (HI), and the like.

In some cases, a nucleotide sequence encoding a CasJ guide RNA is operably linked to (under the control of) a promoter operable in a eukaryotic cell (e.g., a U6 promoter, an enhanced U6 promoter, an HI promoter, and the like). As would be understood by one of ordinary skill in the art, when expressing an RNA (e.g., a guide RNA) from a nucleic acid (e.g., an expression vector) using a U6 promoter (e.g., in a eukaryotic cell), or another PolIII promoter, the RNA may need to be mutated if there are several Ts in a row (coding for Us in the RNA). This is because a string of Ts (e.g., 5 Ts) in DNA can act as a terminator for polymerase III (PolIII). Thus, in order to ensure transcription of a guide RNA (e.g., the activator portion and/or targeter portion, in dual guide or single guide format) in a eukaryotic cell it may sometimes be necessary to modify the sequence encoding the guide RNA to eliminate runs of Ts. In some cases, a nucleotide sequence encoding a CasJ protein (e.g., a wild type CasJ protein, a nickase CasJ protein, a dCasJ protein, a chimeric CasJ protein, CasJ fusion polypeptide, and the like) is operably linked to a promoter operable in a eukaryotic cell (e.g., a CMV promoter, an EF1a promoter, an estrogen receptor-regulated promoter, and the like).

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; estrogen and/or an estrogen analog; IPTG; etc.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is a spatially restricted promoter (e.g., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used as long as the promoter is functional in the targeted host cell (e.g., eukaryotic cell; prokaryotic cell). In some cases, the promoter is a reversible promoter. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including Tet Activators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

Methods of introducing a nucleic acid (e.g., a nucleic acid comprising a donor polynucleotide sequence, one or more nucleic acids encoding a CasJ protein and/or a CasJ guide RNA, and the like) into a host cell are known in the art, and any convenient method can be used to introduce a nucleic acid (e.g., an expression construct) into a cell. Suitable methods include e.g., viral infection, transfection, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct microinjection, nanoparticle-mediated nucleic acid delivery, and the like.

Introducing the recombinant expression vector into cells can occur in any culture media and under any culture conditions that promote the survival of the cells. Introducing the recombinant expression vector into a target cell can be carried out in vivo or ex vivo. Introducing the recombinant expression vector into a target cell can be carried out in vitro.

In some embodiments, a CasJ protein can be provided as RNA. The RNA can be provided by direct chemical synthesis or may be transcribed in vitro from a DNA (e.g., encoding the CasJ protein). Once synthesized, the RNA may be introduced into a cell by any of the well-known techniques for introducing nucleic acids into cells (e.g., microinjection, electroporation, transfection, etc.).

Nucleic acids may be provided to the cells using well-developed transfection techniques; see, e.g., Angel and Yanik (2010) PLoS ONE 5(7): e1756, and the commercially available TransMessenger® reagents from Qiagen, Stemfect™ RNA Transfection Kit from Stemgent, and TransIT®-mRNA Transfection Kit from Mirus Bio LLC. See also Beumer et al. (2008) PNAS 105(50): 19821-19826.

Vectors may be provided directly to a target host cell. In other words, the cells are contacted with vectors comprising the subject nucleic acids (e.g., recombinant expression vectors having the donor template sequence and encoding the CasJ guide RNA; recombinant expression vectors encoding the CasJ protein; etc.) such that the vectors are taken up by the cells. Methods for contacting cells with nucleic acid vectors that are plasmids, include electroporation, calcium chloride transfection, microinjection, and lipofection are well known in the art. For viral vector delivery, cells can be contacted with viral particles comprising the subject viral expression vectors.

Retroviruses, for example, lentiviruses, are suitable for use in methods of the present disclosure. Commonly used retroviral vectors are "defective", e.g., unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing subject vector expression vectors into packaging cell lines and of collecting the viral particles that are generated by the packaging lines are well known in the art. Nucleic acids can also introduced by direct micro-injection (e.g., injection of RNA).

Vectors used for providing the nucleic acids encoding CasJ guide RNA and/or a CasJ polypeptide to a target host cell can include suitable promoters for driving the expression, that is, transcriptional activation, of the nucleic acid of interest. In other words, in some cases, the nucleic acid of interest will be operably linked to a promoter. This may include ubiquitously acting promoters, for example, the CMV-actin promoter, or inducible promoters, such as promoters that are active in particular cell populations or that respond to the presence of drugs such as tetracycline. By transcriptional activation, it is intended that transcription will be increased above basal levels in the target cell by 10 fold, by 100 fold, more usually by 1000 fold. In addition, vectors used for providing a nucleic acid encoding a CasJ guide RNA and/or a CasJ protein to a cell may include nucleic acid sequences that encode for selectable markers in the target cells, so as to identify cells that have taken up the CasJ guide RNA and/or CasJ protein.

A nucleic acid comprising a nucleotide sequence encoding a CasJ polypeptide, or a CasJ fusion polypeptide, is in some cases an RNA. Thus, a CasJ fusion protein can be introduced into cells as RNA. Methods of introducing RNA into cells are known in the art and may include, for example, direct injection, transfection, or any other method used for the introduction of DNA. A CasJ protein may instead be provided to cells as a polypeptide. Such a polypeptide may optionally be fused to a polypeptide domain that increases solubility of the product. The domain may be linked to the polypeptide through a defined protease cleavage site, e.g., a TEV sequence, which is cleaved by TEV protease. The linker may also include one or more flexible sequences, e.g., from 1 to 10 glycine residues. In some embodiments, the cleavage of the fusion protein is performed in a buffer that maintains solubility of the product, e.g., in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g., IF2 domain, GST domain, GRPE domain, and the like. The polypeptide may be formulated for improved stability. For example, the peptides may be PEGylated, where the polyethyleneoxy group provides for enhanced lifetime in the blood stream.

Additionally or alternatively, a CasJ polypeptide of the present disclosure may be fused to a polypeptide permeant domain to promote uptake by the cell. A number of permeant domains are known in the art and may be used in the non-integrating polypeptides of the present disclosure, including peptides, peptidomimetics, and non-peptide carriers. For example, a permeant peptide may be derived from the third alpha helix of *Drosophila melanogaster* transcription factor Antennapaedia, referred to as penetratin, which comprises the amino acid sequence of SEQ ID NO: 58. As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A 2000 Nov. 21; 97(24): 13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site will be determined by routine experimentation.

A CasJ polypeptide of the present disclosure may be produced in vitro or by eukaryotic cells or by prokaryotic cells, and it may be further processed by unfolding, e.g., heat denaturation, dithiothreitol reduction, etc. and may be further refolded, using methods known in the art. Modifications of interest that do not alter primary sequence include chemical derivatization of polypeptides, e.g., acylation, acetylation, carboxylation, amidation, etc. Also included are modifications of glycosylation, e.g., those made by modifying the glycosylation patterns of a polypeptide during its synthesis and processing or in further processing steps; e.g., by exposing the polypeptide to enzymes which affect glycosylation, such as mammalian glycosylating or deglycosylating enzymes. Also embraced are sequences that have phosphorylated amino acid residues, e.g., phosphotyrosine, phosphoserine, or phosphothreonine.

Also suitable for inclusion in embodiments of the present disclosure are nucleic acids (e.g., encoding a CasJ guide RNA, encoding a CasJ fusion protein, etc.) and proteins (e.g., a CasJ fusion protein derived from a wild type protein or a variant protein) that have been modified using ordinary molecular biological techniques and synthetic chemistry so as to improve their resistance to proteolytic degradation, to change the target sequence specificity, to optimize solubility properties, to alter protein activity (e.g., transcription modulatory activity, enzymatic activity, etc.) or to render them more suitable. Analogs of such polypeptides include those containing residues other than naturally-occurring L-amino acids, e.g., D-amino acids or non-naturally-occurring synthetic amino acids. D-amino acids may be substituted for some or all of the amino acid residues.

A CasJ polypeptide of the present disclosure may be prepared by in vitro synthesis, using conventional methods as known in the art. Various commercial synthetic apparatuses are available, for example, automated synthesizers by Applied Biosystems, Inc., Beckman, etc. By using synthesizers, naturally-occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

A CasJ polypeptide of the present disclosure may also be isolated and purified in accordance with conventional methods of recombinant synthesis. A lysate may be prepared of the expression host and the lysate purified using high performance liquid chromatography (HPLC), exclusion chromatography, gel electrophoresis, affinity chromatography, or other purification technique. For the most part, the compositions which are used will comprise 20% or more by weight of the desired product, more usually 75% or more by weight, preferably 95% or more by weight, and for therapeutic purposes, usually 99.5% or more by weight, in relation to contaminants related to the method of preparation of the product and its purification. Usually, the percentages will be based upon total protein. Thus, in some cases, a CasJ polypeptide, or a CasJ fusion polypeptide, of the present disclosure is at least 80% pure, at least 85% pure, at least 90% pure, at least 95% pure, at least 98% pure, or at least 99% pure (e.g., free of contaminants, non-CasJ proteins or other macromolecules, etc.).

To induce cleavage or any desired modification to a target nucleic acid (e.g., genomic DNA), or any desired modification to a polypeptide associated with target nucleic acid, the CasJ guide RNA and/or the CasJ polypeptide of the present disclosure and/or the donor template sequence, whether they be introduced as nucleic acids or polypeptides, are provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the subject cells one or more times, e.g., one time, twice, three times, or more than three times, and the cells allowed to incubate with the agent(s) for some amount of time following each contacting event e.g., 16-24 hours, after which time the media is replaced with fresh media and the cells are cultured further.

In cases in which two or more different targeting complexes are provided to the cell (e.g., two different CasJ guide RNAs that are complementary to different sequences within the same or different target nucleic acid), the complexes may be provided simultaneously (e.g., as two polypeptides and/or nucleic acids), or delivered simultaneously. Alternatively, they may be provided consecutively, e.g., the targeting complex being provided first, followed by the second targeting complex, etc. or vice versa.

To improve the delivery of a DNA vector into a target cell, the DNA can be protected from damage and its entry into the cell facilitated, for example, by using lipoplexes and polyplexes. Thus, in some cases, a nucleic acid of the present disclosure (e.g., a recombinant expression vector of the present disclosure) can be covered with lipids in an organized structure like a micelle or a liposome. When the organized structure is complexed with DNA it is called a lipoplex. There are three types of lipids, anionic (negatively-charged), neutral, or cationic (positively-charged). Lipoplexes that utilize cationic lipids have proven utility for gene transfer. Cationic lipids, due to their positive charge, naturally complex with the negatively charged DNA. Also as a result of their charge, they interact with the cell membrane. Endocytosis of the lipoplex then occurs, and the DNA is released into the cytoplasm. The cationic lipids also protect against degradation of the DNA by the cell.

Complexes of polymers with DNA are called polyplexes. Most polyplexes consist of cationic polymers and their production is regulated by ionic interactions. One large difference between the methods of action of polyplexes and lipoplexes is that polyplexes cannot release their DNA load into the cytoplasm, so to this end, co-transfection with endosome-lytic agents (to lyse the endosome that is made during endocytosis) such as inactivated adenovirus must occur. However, this is not always the case; polymers such as polyethylenimine have their own method of endosome disruption as does chitosan and trimethylchitosan.

Dendrimers, a highly branched macromolecule with a spherical shape, may be also be used to genetically modify stem cells. The surface of the dendrimer particle may be functionalized to alter its properties. In particular, it is possible to construct a cationic dendrimer (i.e., one with a positive surface charge). When in the presence of genetic material such as a DNA plasmid, charge complementarity leads to a temporary association of the nucleic acid with the cationic dendrimer. On reaching its destination, the dendrimer-nucleic acid complex can be taken up into a cell by endocytosis.

In some cases, a nucleic acid of the disclosure (e.g., an expression vector) includes an insertion site for a guide sequence of interest. For example, a nucleic acid can include an insertion site for a guide sequence of interest, where the insertion site is immediately adjacent to a nucleotide sequence encoding the portion of a CasJ guide RNA that does not change when the guide sequence is changed to hybridize to a desired target sequence (e.g., sequences that contribute to the CasJ binding aspect of the guide RNA, e.g, the sequences that contribute to the dsRNA duplex(es) of the CasJ guide RNA—this portion of the guide RNA can also be referred to as the 'scaffold' or 'constant region' of the guide RNA). Thus, in some cases, a subject nucleic acid (e.g., an expression vector) includes a nucleotide sequence encoding a CasJ guide RNA, except that the portion encoding the guide sequence portion of the guide RNA is an insertion sequence (an insertion site). An insertion site is any nucleotide sequence used for the insertion of a the desired sequence. "Insertion sites" for use with various technologies are known to those of ordinary skill in the art and any convenient insertion site can be used. An insertion site can be for any method for manipulating nucleic acid sequences. For example, in some cases the insertion site is a multiple cloning site (MCS) (e.g., a site including one or more restriction enzyme recognition sequences), a site for ligation independent cloning, a site for recombination based cloning (e.g., recombination based on att sites), a nucleotide sequence recognized by a CRISPR/Cas (e.g., Cas9) based technology, and the like.

An insertion site can be any desirable length, and can depend on the type of insertion site (e.g., can depend on whether (and how many) the site includes one or more restriction enzyme recognition sequences, whether the site includes a target site for a CRISPR/Cas protein, etc.). In some cases, an insertion site of a subject nucleic acid is 3 or more nucleotides (nt) in length (e.g., 5 or more, 8 or more, 10 or more, 15 or more, 17 or more, 18 or more, 19 or more, 20 or more or 25 or more, or 30 or more nt in length). In some cases, the length of an insertion site of a subject nucleic acid has a length in a range of from 2 to 50 nucleotides (nt) (e.g., from 2 to 40 nt, from 2 to 30 nt, from 2 to 25 nt, from 2 to 20 nt, from 5 to 50 nt, from 5 to 40 nt, from 5 to 30 nt, from 5 to 25 nt, from 5 to 20 nt, from 10 to 50 nt, from 10 to 40 nt, from 10 to 30 nt, from 10 to 25 nt, from 10 to 20 nt, from 17 to 50 nt, from 17 to 40 nt, from 17 to 30 nt, from 17 to 25 nt). In some cases, the length of an insertion site of a subject nucleic acid has a length in a range of from 5 to 40 nt.

In some embodiments, a subject nucleic acid (e.g., a CasJ guide RNA) has one or more modifications, e.g., a base modification, a backbone modification, etc., to provide the nucleic acid with a new or enhanced feature (e.g., improved stability). A nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Suitable nucleic acid modifications include, but are not limited to: 2'Omethyl modified nucleotides, 2' Fluoro modified nucleotides, locked nucleic acid (LNA) modified nucleotides, peptide nucleic acid (PNA) modified nucleotides, nucleotides with phosphorothioate linkages, and a 5' cap (e.g., a 7-methylguanylate cap (m7G)). Additional details and additional modifications are described below.

A 2'-O-Methyl modified nucleotide (also referred to as 2'-O-Methyl RNA) is a naturally-occurring modification of RNA found in tRNA and other small RNAs that arises as a post-transcriptional modification. Oligonucleotides can be directly synthesized that contain 2'-O-Methyl RNA. This modification increases Tm of RNA:RNA duplexes but results in only small changes in RNA:DNA stability. It is stabile with respect to attack by single-stranded ribonucleases and is typically 5 to 10-fold less susceptible to DNases than DNA. It is commonly used in antisense oligos as a means to increase stability and binding affinity to the target message.

2' Fluoro modified nucleotides (e.g., 2' Fluoro bases) have a fluorine modified ribose which increases binding affinity (Tm) and also confers some relative nuclease resistance when compared to native RNA. These modifications are commonly employed in ribozymes and siRNAs to improve stability in serum or other biological fluids.

LNA bases have a modification to the ribose backbone that locks the base in the C3'-endo position, which favors RNA A-type helix duplex geometry. This modification significantly increases Tm and is also very nuclease resistant. Multiple LNA insertions can be placed in an oligo at any position except the 3'-end. Applications have been described ranging from antisense oligos to hybridization probes to SNP detection and allele specific PCR. Due to the large increase in Tm conferred by LNAs, they also can cause an increase in primer dimer formation as well as self-hairpin formation. In some cases, the number of LNAs incorporated into a single oligo is 10 bases or less.

The phosphorothioate (PS) bond (i.e., a phosphorothioate linkage) substitutes a sulfur atom for a non-bridging oxygen in the phosphate backbone of a nucleic acid (e.g., an oligo). This modification renders the internucleotide linkage resistant to nuclease degradation. Phosphorothioate bonds can be introduced between the last 3-5 nucleotides at the 5'- or 3'-end of the oligo to inhibit exonuclease degradation. Including phosphorothioate bonds within the oligo (e.g., throughout the entire oligo) can help reduce attack by endonucleases as well. In some embodiments, a subject nucleic acid has one or more nucleotides that are 2'-O-Methyl modified nucleotides. In some embodiments, a subject nucleic acid (e.g., a dsRNA, a siNA, etc.) has one or more 2' Fluoro modified nucleotides. In some embodiments, a subject nucleic acid (e.g., a dsRNA, a siNA, etc.) has one or more LNA bases. In some embodiments, a subject nucleic acid (e.g., a dsRNA, a siNA, etc.) has one or more nucleotides that are linked by a phosphorothioate bond (i.e., the subject nucleic acid has one or more phosphorothioate linkages). In some embodiments, a subject nucleic acid (e.g., a dsRNA, a siNA, etc.) has a 5' cap (e.g., a 7-methylguanylate cap (m7G)). In some embodiments, a subject nucleic acid (e.g., a dsRNA, a siNA, etc) has a combination of modified nucleotides. For example, a subject nucleic acid (e.g., a dsRNA, a siNA, etc.) can have a 5' cap (e.g., a 7-methylguanylate cap (m7G)) in addition to having one or more nucleotides with other modifications (e.g., a 2'-O-Methyl nucleotide and/or a 2' Fluoro modified nucleotide and/or a LNA base and/or a phosphorothioate linkage).

Examples of suitable nucleic acids (e.g., a CasJ guide RNA) containing modifications include nucleic acids containing modified backbones or non-natural internucleoside linkages. Nucleic acids having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage e.g., a single inverted nucleoside residue which may be a basic (the nucleobase is missing or has a hydroxyl group in place thereof). Various salts (such as, for example, potassium or sodium), mixed salts and free acid forms are also included.

In some embodiments, a subject nucleic acid comprises one or more phosphorothioate and/or heteroatom internucleoside linkages, in particular —CH$_2$—NH—O—CH$_2$—, —CH$_2$—N(CH$_3$)—O—CH$_2$— (known as a methylene (methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P(=O)(OH)—O—CH$_2$—). MMI type internucleoside linkages are disclosed in the above referenced U.S. Pat. No. 5,489,677, the disclosure of which is incorporated herein by reference in its entirety. Suitable amide internucleoside linkages are disclosed in U.S. Pat. No. 5,602,240, the disclosure of which is incorporated herein by reference in its entirety.

Also suitable are nucleic acids having morpholino backbone structures as described in, e.g., U.S. Pat. No. 5,034,506. For example, in some embodiments, a subject nucleic acid comprises a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

A subject nucleic acid can be a nucleic acid mimetic. The term "mimetic" as it is applied to polynucleotides is intended to include polynucleotides wherein only the furanose ring or both the furanose ring and the internucleotide linkage are replaced with non-fur anose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262, the disclosures of which are incorporated herein by reference in their entirety.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, Biochemistry, 2002, 41(14), 4503-4510). Morpholino-based polynucleotides are disclosed in U.S. Pat. No. 5,034,506, the disclosure of which is incorporated herein by reference in its entirety. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., Am. Chem. Soc, 2000, 122, 8595-8602, the disclosure of which is incorporated herein by reference in its entirety). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—$CH_2$—), group bridging the 2' oxygen atom and the 4' carbon atom wherein n is 1 or 2 (Singh et al., Chem. Commun., 1998, 4, 455-456, the disclosure of which is incorporated herein by reference in its entirety). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (e.g., Wahlestedt et al., Proc. Natl. Acad. Sci. U.S.A., 2000, 97, 5633-5638, the disclosure of which is incorporated herein by reference in its entirety).

The synthesis and preparation of the LNA monomers adenine, cytosine, guanine, 5-methyl-cytosine, thymine and uracil, along with their oligomerization, and nucleic acid recognition properties have been described (e.g., Koshkin et al., Tetrahedron, 1998, 54, 3607-3630, the disclosure of which is incorporated herein by reference in its entirety). LNAs and preparation thereof are also described in WO 98/39352 and WO 99/14226, as well as U.S. applications 20120165514, 20100216983, 20090041809, 20060117410, 20040014959, 20020094555, and 20020086998, the disclosures of which are incorporated herein by reference in their entirety.

A subject nucleic acid can also include one or more substituted sugar moieties. Suitable polynucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C.sub. 1 to do alkyl or $C_2$ to do alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other suitable polynucleotides comprise a sugar substituent group selected from: d to $C_{10}$ lower alkyl, substituted lower alkyl, alkenyl, alkynyl, alkaryl, aralkyl, O-alkaryl or O-aralkyl, SH, $SCH_3$, OCN, CI, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504, the disclosure of which is incorporated herein by reference in its entirety) e.g., an alkoxyalkoxy group. A further suitable modification includes 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—N($CH_3$)$_2$.

Other suitable sugar substituent groups include methoxy (—O—$CH_3$), aminopropoxy (—O $CH_2CH_2CH_2NH_2$), allyl (—$CH_2$—CH=$CH_2$), —O-allyl (—O—$CH_2$—CH=$CH_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mime tics such as cyclobutyl moieties in place of the pentofuranosyl sugar.

A subject nucleic acid may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH₃) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrirnido(5,4-b)(1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g., 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993; the disclosures of which are incorporated herein by reference in their entirety. Certain of these nucleobases are useful for increasing the binding affinity of an oligomeric compound. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications, CRC Press, Boca Raton, 1993, pp. 276-278; the disclosure of which is incorporated herein by reference in its entirety) and are suitable base substitutions, e.g., when combined with 2'-O-methoxyethyl sugar modifications.

Another possible modification of a subject nucleic acid involves chemically linking to the polynucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a subject nucleic acid.

Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al, FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., /. Pharmacol. Exp. Ther., 1996, 277, 923-937).

A conjugate may include a "Protein Transduction Domain" or PTD (also known as a CPP—cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle (e.g., the nucleus). In some embodiments, a PTD is covalently linked to the 3' end of an exogenous polynucleotide. In some embodiments, a PTD is covalently linked to the 5' end of an exogenous polynucleotide. Examples of PTDs include but are not limited to a minimal undecapeptide protein transduction domain (corresponding to residues 47-57 of HIV-1 TAT comprising SEQ ID NO:33); a polyarginine sequence comprising a number of arginines sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); an *Drosophila* Antennapedia protein transduction domain (Noguchi et al. (2003) Diabetes 52(7): 1732-1737); a truncated human calcitonin peptide (Trehin et al. (2004) Pharm. Research 21: 1248-1256); polylysine (Wender et al. (2000) Proc. Natl. Acad. Sci. USA 97: 13003-13008); SEQ ID NO:34; Transportan (SEQ ID NO:35); SEQ ID NO:36; and SEQ ID NO:37. Useful PTDs include but are not limited to, SEQ ID NO:38 or 39; an arginine homopolymer of from 3 arginine residues to 50 arginine residues; useful PTD domain amino acid sequences include, but are not limited to, any of the following: SEQ ID NO:40-43, and 44. In some embodiments, the PTD is an activatable CPP (ACPP) (Aguilera et al. (2009) Integr Biol (Camb) June; 1(5-6): 371-381). ACPPs comprise a polycationic CPP (e.g., Arg9 or "R9")

connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

A CasJ guide RNA (or a nucleic acid comprising a nucleotide sequence encoding same) and/or a CasJ polypeptide of the present disclosure (or a nucleic acid comprising a nucleotide sequence encoding same) and/or a CasJ fusion polypeptide of the present disclosure (or a nucleic acid that includes a nucleotide sequence encoding a CasJ fusion polypeptide of the present disclosure) and/or a donor polynucleotide (donor template) can be introduced into a host cell by any of a variety of well-known methods.

Any of a variety of compounds and methods can be used to deliver to a target cell a CasJ system of the present disclosure (e.g., where a CasJ system comprises: a) a CasJ polypeptide of the present disclosure and a CasJ guide RNA; b) a CasJ polypeptide of the present disclosure, a CasJ guide RNA, and a donor template nucleic acid; c) a CasJ fusion polypeptide of the present disclosure and a CasJ guide RNA; d) a CasJ fusion polypeptide of the present disclosure, a CasJ guide RNA, and a donor template nucleic acid; e) an mRNA encoding a CasJ polypeptide of the present disclosure; and a CasJ guide RNA; f) an mRNA encoding a CasJ polypeptide of the present disclosure, a CasJ guide RNA, and a donor template nucleic acid; g) an mRNA encoding a CasJ fusion polypeptide of the present disclosure; and a CasJ guide RNA; h) an mRNA encoding a CasJ fusion polypeptide of the present disclosure, a CasJ guide RNA, and a donor template nucleic acid; i) a recombinant expression vector comprising a nucleotide sequence encoding a CasJ polypeptide of the present disclosure and a nucleotide sequence encoding a CasJ guide RNA; j) a recombinant expression vector comprising a nucleotide sequence encoding a CasJ polypeptide of the present disclosure, a nucleotide sequence encoding a CasJ guide RNA, and a nucleotide sequence encoding a donor template nucleic acid; k) a recombinant expression vector comprising a nucleotide sequence encoding a CasJ fusion polypeptide of the present disclosure and a nucleotide sequence encoding a CasJ guide RNA; l) a recombinant expression vector comprising a nucleotide sequence encoding a CasJ fusion polypeptide of the present disclosure, a nucleotide sequence encoding a CasJ guide RNA, and a nucleotide sequence encoding a donor template nucleic acid; m) a first recombinant expression vector comprising a nucleotide sequence encoding a CasJ polypeptide of the present disclosure, and a second recombinant expression vector comprising a nucleotide sequence encoding a CasJ guide RNA; n) a first recombinant expression vector comprising a nucleotide sequence encoding a CasJ polypeptide of the present disclosure, and a second recombinant expression vector comprising a nucleotide sequence encoding a CasJ guide RNA; and a donor template nucleic acid; o) a first recombinant expression vector comprising a nucleotide sequence encoding a CasJ fusion polypeptide of the present disclosure, and a second recombinant expression vector comprising a nucleotide sequence encoding a CasJ guide RNA; p) a first recombinant expression vector comprising a nucleotide sequence encoding a CasJ fusion polypeptide of the present disclosure, and a second recombinant expression vector comprising a nucleotide sequence encoding a CasJ guide RNA; and a donor template nucleic acid; q) a recombinant expression vector comprising a nucleotide sequence encoding a CasJ polypeptide of the present disclosure, a nucleotide sequence encoding a first CasJ guide RNA, and a nucleotide sequence encoding a second CasJ guide RNA; or r) a recombinant expression vector comprising a nucleotide sequence encoding a CasJ fusion polypeptide of the present disclosure, a nucleotide sequence encoding a first CasJ guide RNA, and a nucleotide sequence encoding a second CasJ guide RNA; or some variation of one of (a) through (r). As a non-limiting example, a CasJ system of the present disclosure can be combined with a lipid. As another non-limiting example, a CasJ system of the present disclosure can be combined with a particle, or formulated into a particle.

Methods of introducing a nucleic acid into a host cell are known in the art, and any convenient method can be used to introduce a subject nucleic acid (e.g., an expression construct/vector) into a target cell (e.g., prokaryotic cell, eukaryotic cell, plant cell, animal cell, mammalian cell, human cell, and the like). Suitable methods include, e.g., viral infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: 50169-409X(12)00283-9. doi: 10.1016/j.addr.2012.09.023), and the like.

In some cases, a CasJ polypeptide of the present disclosure is provided as a nucleic acid (e.g., an mRNA, a DNA, a plasmid, an expression vector, a viral vector, etc.) that encodes the CasJ polypeptide. In some cases, the CasJ polypeptide of the present disclosure is provided directly as a protein (e.g., without an associated guide RNA or with an associate guide RNA, i.e., as a ribonucleoprotein complex). A CasJ polypeptide of the present disclosure can be introduced into a cell (provided to the cell) by any convenient method; such methods are known to those of ordinary skill in the art. As an illustrative example, a CasJ polypeptide of the present disclosure can be injected directly into a cell (e.g., with or without a CasJ guide RNA or nucleic acid encoding a CasJ guide RNA, and with or without a donor polynucleotide). As another example, a preformed complex of a CasJ polypeptide of the present disclosure and a CasJ guide RNA (an RNP) can be introduced into a cell (e.g, eukaryotic cell) (e.g., via injection, via nucleofection; via a protein transduction domain (PTD) conjugated to one or more components, e.g., conjugated to the CasJ protein, conjugated to a guide RNA, conjugated to a CasJ polypeptide of the present disclosure and a guide RNA; etc.). In some cases, a CasJ fusion polypeptide (e.g., dCasJ fused to a fusion partner, nickase CasJ fused to a fusion partner, etc.) of the present disclosure is provided as a nucleic acid (e.g., an mRNA, a DNA, a plasmid, an expression vector, a viral vector, etc.) that encodes the CasJ fusion polypeptide. In some cases, the CasJ fusion polypeptide of the present disclosure is provided directly as a protein (e.g., without an associated guide RNA or with an associate guide RNA, i.e., as a ribonucleoprotein complex). A CasJ fusion polypeptide of the present disclosure can be introduced into a cell (provided to the cell) by any convenient method; such methods are known to those of ordinary skill in the art. As an illustrative example, a CasJ fusion polypeptide of the present disclosure can be injected directly into a cell (e.g., with or without nucleic acid encoding a CasJ guide RNA and with or without a donor polynucleotide). As another example, a preformed complex of a CasJ fusion polypeptide of the present disclosure and a CasJ guide RNA (an RNP)

can be introduced into a cell (e.g., via injection, via nucleofection; via a protein transduction domain (PTD) conjugated to one or more components, e.g., conjugated to the CasJ fusion protein, conjugated to a guide RNA, conjugated to a CasJ fusion polypeptide of the present disclosure and a guide RNA; etc.).

In some cases, a nucleic acid (e.g., a CasJ guide RNA; a nucleic acid comprising a nucleotide sequence encoding a CasJ polypeptide of the present disclosure; etc.) is delivered to a cell (e.g., a target host cell) and/or a polypeptide (e.g., a CasJ polypeptide; a CasJ fusion polypeptide) in a particle, or associated with a particle. In some cases, a CasJ system of the present disclosure is delivered to a cell in a particle, or associated with a particle. The terms "particle" and nanoparticle" can be used interchangeable, as appropriate. A recombinant expression vector comprising a nucleotide sequence encoding a CasJ polypeptide of the present disclosure and/or a CasJ guide RNA, an mRNA comprising a nucleotide sequence encoding a CasJ polypeptide of the present disclosure, and guide RNA may be delivered simultaneously using particles or lipid envelopes; for instance, a CasJ polypeptide and a CasJ guide RNA, e.g., as a complex (e.g., a ribonucleoprotein (RNP) complex), can be delivered via a particle, e.g., a delivery particle comprising lipid or lipidoid and hydrophilic polymer, e.g., a cationic lipid and a hydrophilic polymer, for instance wherein the cationic lipid comprises 1,2-dioleoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the particle further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5). For example, a particle can be formed using a multistep process in which a CasJ polypeptide and a CasJ guide RNA are mixed together, e.g., at a 1:1 molar ratio, e.g., at room temperature, e.g., for 30 minutes, e.g., in sterile, nuclease free 1× phosphate-buffered saline (PBS); and separately, DOTAP, DMPC, PEG, and cholesterol as applicable for the formulation are dissolved in alcohol, e.g., 100% ethanol; and, the two solutions are mixed together to form particles containing the complexes).

A CasJ polypeptide of the present disclosure (or an mRNA comprising a nucleotide sequence encoding a CasJ polypeptide of the present disclosure; or a recombinant expression vector comprising a nucleotide sequence encoding a CasJ polypeptide of the present disclosure) and/or CasJ guide RNA (or a nucleic acid such as one or more expression vectors encoding the CasJ guide RNA) may be delivered simultaneously using particles or lipid envelopes. For example, a biodegradable core-shell structured nanoparticle with a poly ((3-amino ester) (PBAE) core enveloped by a phospholipid bilayer shell can be used. In some cases, particles/nanoparticles based on self-assembling bioadhesive polymers are used; such particles/nanoparticles may be applied to oral delivery of peptides, intravenous delivery of peptides and nasal delivery of peptides, e.g., to the brain. Other embodiments, such as oral absorption and ocular delivery of hydrophobic drugs are also contemplated. A molecular envelope technology, which involves an engineered polymer envelope which is protected and delivered to the site of the disease, can be used. Doses of about 5 mg/kg can be used, with single or multiple doses, depending on various factors, e.g., the target tissue.

Lipidoid compounds (e.g., as described in US patent application 20110293703) are also useful in the administration of polynucleotides, and can be used to deliver a CasJ polypeptide of the present disclosure, a CasJ fusion polypeptide of the present disclosure, an RNP of the present disclosure, a nucleic acid of the present disclosure, or a CasJ system of the present disclosure.

In one aspect, the aminoalcohol lipidoid compounds are combined with an agent to be delivered to a cell or a subject to form microparticles, nanoparticles, liposomes, or micelles. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

A poly(beta-amino alcohol) (PBAA) can be used to deliver a CasJ polypeptide of the present disclosure, a CasJ fusion polypeptide of the present disclosure, an RNP of the present disclosure, a nucleic acid of the present disclosure, or a CasJ system of the present disclosure, to a target cell. US Patent Publication No. 20130302401 relates to a class of poly(beta-amino alcohols) (PBAAs) that has been prepared using combinatorial polymerization.

Sugar-based particles may be used, for example GalNAc, as described with reference to WO2014118272 (incorporated herein by reference) and Nair, J K et al., 2014, Journal of the American Chemical Society 136 (49), 16958-16961) can be used to deliver a CasJ polypeptide of the present disclosure, a CasJ fusion polypeptide of the present disclosure, an RNP of the present disclosure, a nucleic acid of the present disclosure, or a CasJ system of the present disclosure, to a target cell.

In some cases, lipid nanoparticles (LNPs) are used to deliver a CasJ polypeptide of the present disclosure, a CasJ fusion polypeptide of the present disclosure, an RNP of the present disclosure, a nucleic acid of the present disclosure, or a CasJ system of the present disclosure, to a target cell. Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). Preparation of LNPs and is described in, e.g., Rosin et al. (2011) Molecular Therapy 19: 1286-2200). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinKDMA), 1,2-dilinoleyl-4-(2-dimethylaminoethyl)-[1,3]-dioxolane (DLinKC2-DM A), (3-o-[2"-(methoxypolyethyleneglycol 2000) succinoyl]-1,2-dimyristoyl-sn-glycol (PEG-S-DMG), and R-3-[(.omega.-methoxy-poly(ethylene glycol)2000) carbamoyl]-1,2-dimyristyloxlpropyl-3-amine (PEG-C-DOMG) may be used. A nucleic acid (e.g., a CasJ guide RNA; a nucleic acid of the present disclosure; etc.) may be encapsulated in LNPs containing DLinDAP, DLinDMA, DLinK-DMA, and DLinKC2-DMA (cationic lipid:DSPC:CHOL:PEGS-DMG or PEG-C-DOMG at 40:10:40:10 molar ratios). In some cases, 0.2% SP-DiOC18 is incorporated.

Spherical Nucleic Acid (SNA™) constructs and other nanoparticles (particularly gold nanoparticles) can be used to deliver a CasJ polypeptide of the present disclosure, a CasJ fusion polypeptide of the present disclosure, an RNP of the present disclosure, a nucleic acid of the present disclosure, or a CasJ system of the present disclosure, to a target cell. See, e.g., Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134: 1376-1391, Young et al., Nano Lett. 2012 12:3867-71, Zheng et al., Proc. Natl. Acad. Sci. USA. 2012 109: 11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19): 7625-7630, Jensen et al, Sci. Transl. Med. 5, 209ra152 (2013) and Mirkin, et al., Small, 10: 186-192.

Self-assembling nanoparticles with RNA may be constructed with polyethyleneimine (PEI) that is PEGylated with an Arg-Gly-Asp (RGD) peptide ligand attached at the distal end of the polyethylene glycol (PEG).

In general, a "nanoparticle" refers to any particle having a diameter of less than 1000 nm. In some cases, nanoparticles suitable for use in delivering a CasJ polypeptide of the present disclosure, a CasJ fusion polypeptide of the present disclosure, an RNP of the present disclosure, a nucleic acid of the present disclosure, or a CasJ system of the present disclosure, to a target cell have a diameter of 500 nm or less, e.g., from 25 nm to 35 nm, from 35 nm to 50 nm, from 50 nm to 75 nm, from 75 nm to 100 nm, from 100 nm to 150 nm, from 150 nm to 200 nm, from 200 nm to 300 nm, from 300 nm to 400 nm, or from 400 nm to 500 nm. In some cases, nanoparticles suitable for use in delivering a CasJ polypeptide of the present disclosure, a CasJ fusion polypeptide of the present disclosure, an RNP of the present disclosure, a nucleic acid of the present disclosure, or a CasJ system of the present disclosure, to a target cell have a diameter of from 25 nm to 200 nm. In some cases, nanoparticles suitable for use in delivering a CasJ polypeptide of the present disclosure, a CasJ fusion polypeptide of the present disclosure, an RNP of the present disclosure, a nucleic acid of the present disclosure, or a CasJ system of the present disclosure, to a target cell have a diameter of 100 nm or less In some cases, nanoparticles suitable for use in delivering a CasJ polypeptide of the present disclosure, a CasJ fusion polypeptide of the present disclosure, an RNP of the present disclosure, a nucleic acid of the present disclosure, or a CasJ system of the present disclosure, to a target cell have a diameter of from 35 nm to 60 nm.

Nanoparticles suitable for use in delivering a CasJ polypeptide of the present disclosure, a CasJ fusion polypeptide of the present disclosure, an RNP of the present disclosure, a nucleic acid of the present disclosure, or a CasJ system of the present disclosure, to a target cell may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically below 10 nm) that quantization of electronic energy levels occurs. Such nanoscale particles are used in biomedical applications as drug carriers or imaging agents and may be adapted for similar purposes in the present disclosure.

Semi-solid and soft nanoparticles are also suitable for use in delivering a CasJ polypeptide of the present disclosure, a CasJ fusion polypeptide of the present disclosure, an RNP of the present disclosure, a nucleic acid of the present disclosure, or a CasJ system of the present disclosure, to a target cell. A prototype nanoparticle of semi-solid nature is the liposome.

In some cases, an exosome is used to deliver a CasJ polypeptide of the present disclosure, a CasJ fusion polypeptide of the present disclosure, an RNP of the present disclosure, a nucleic acid of the present disclosure, or a CasJ system of the present disclosure, to a target cell. Exosomes are endogenous nano-vesicles that transport RNAs and proteins, and which can deliver RNA to the brain and other target organs.

In some cases, a liposome is used to deliver a CasJ polypeptide of the present disclosure, a CasJ fusion polypeptide of the present disclosure, an RNP of the present disclosure, a nucleic acid of the present disclosure, or a CasJ system of the present disclosure, to a target cell. Liposomes are spherical vesicle structures composed of a uni- or multilamellar lipid bilayer surrounding internal aqueous compartments and a relatively impermeable outer lipophilic phospholipid bilayer. Liposomes can be made from several different types of lipids; however, phospholipids are most commonly used to generate liposomes. Although liposome formation is spontaneous when a lipid film is mixed with an aqueous solution, it can also be expedited by applying force in the form of shaking by using a homogenizer, sonicator, or an extrusion apparatus. Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. A liposome formulation may be mainly comprised of natural phospholipids and lipids such as 1,2-distearoryl-sn-glycero-3-phosphatidyl choline (DSPC), sphingomyelin, egg phosphatidylcholines and monosialoganglioside.

A stable nucleic-acid-lipid particle (SNALP) can be used to deliver a CasJ polypeptide of the present disclosure, a CasJ fusion polypeptide of the present disclosure, an RNP of the present disclosure, a nucleic acid of the present disclosure, or a CasJ system of the present disclosure, to a target cell. The SNALP formulation may contain the lipids 3-N-[(methoxypoly(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio. The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulting SNALP liposomes can be about 80-100 nm in size. A SNALP may comprise synthetic cholesterol (Sigma-Aldrich, St Louis, Mo., USA), dipalmitoylphosphatidylcholine (Avanti Polar Lipids, Alabaster, Ala., USA), 3-N-[(w-methoxy poly(ethylene glycol)2000) carbamoyl]-1,2-dimyrestyloxypropylamine, and cationic 1,2-dilinoleyloxy-3-N,Ndimethylaminopropane. A SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N; N-dimethyl)aminopropane (DLinDMA).

Other cationic lipids, such as amino lipid 2,2-dilinoleyl-4-dimethylaminoethyl-[1,3]-dioxolane (DLin-KC2-DMA) can be used to deliver a CasJ polypeptide of the present disclosure, a CasJ fusion polypeptide of the present disclosure, an RNP of the present disclosure, a nucleic acid of the present disclosure, or a CasJ system of the present disclosure, to a target cell. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylenegly-col)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11.+−0.0.04 (n=56), the particles may be extruded up to three times through 80 nm membranes prior to adding the guide RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Lipids may be formulated with a CasJ system of the present disclosure or component(s) thereof or nucleic acids encoding the same to form lipid nanoparticles (LNPs). Suitable lipids include, but are not limited to, DLin-KC2-DMA4, CI 2-200 and colipids disteroylphosphatidyl choline, cholesterol, and PEG-DMG may be formulated with a CasJ system, or component thereof, of the present disclosure, using a spontaneous vesicle formation procedure. The component molar ratio may be about 50/10/38.5/1.5 (DLin-KC2-DMA or C12-200/disteroylphosphatidyl choline/cholesterol/PEG-DMG).

A CasJ system of the present disclosure, or a component thereof, may be delivered encapsulated in PLGA microspheres such as that further described in US published applications 20130252281 and 20130245107 and 20130244279.

Supercharged proteins can be used to deliver a CasJ polypeptide of the present disclosure, a CasJ fusion polypeptide of the present disclosure, an RNP of the present disclosure, a nucleic acid of the present disclosure, or a CasJ system of the present disclosure, to a target cell. Supercharged proteins are a class of engineered or naturally-occurring proteins with unusually high positive or negative net theoretical charge. Both supernegatively and superpositively charged proteins exhibit the ability to withstand thermally or chemically induced aggregation. Superpositively charged proteins are also able to penetrate mammalian cells. Associating cargo with these proteins, such as plasmid DNA, RNA, or other proteins, can facilitate the functional delivery of these macromolecules into mammalian cells both in vitro and in vivo.

Cell Penetrating Peptides (CPPs) can be used to deliver a CasJ polypeptide of the present disclosure, a CasJ fusion polypeptide of the present disclosure, an RNP of the present disclosure, a nucleic acid of the present disclosure, or a CasJ system of the present disclosure, to a target cell. CPPs typically have an amino acid composition that either contains a high relative abundance of positively charged amino acids such as lysine or arginine or has sequences that contain an alternating pattern of polar/charged amino acids and non-polar, hydrophobic amino acids.

The present disclosure provides a modified cell comprising a CasJ polypeptide of the present disclosure and/or a nucleic acid comprising a nucleotide sequence encoding a CasJ polypeptide of the present disclosure. The present disclosure provides a modified cell comprising a CasJ polypeptide of the present disclosure, where the modified cell is a cell that does not normally comprise a CasJ polypeptide of the present disclosure. The present disclosure provides a modified cell (e.g., a genetically modified cell) comprising nucleic acid comprising a nucleotide sequence encoding a CasJ polypeptide of the present disclosure. The present disclosure provides a genetically modified cell that is genetically modified with an mRNA comprising a nucleotide sequence encoding a CasJ polypeptide of the present disclosure. The present disclosure provides a genetically modified cell that is genetically modified with a recombinant expression vector comprising a nucleotide sequence encoding a CasJ polypeptide of the present disclosure. The present disclosure provides a genetically modified cell that is genetically modified with a recombinant expression vector comprising: a) a nucleotide sequence encoding a CasJ polypeptide of the present disclosure; and b) a nucleotide sequence encoding a CasJ guide RNA of the present disclosure. The present disclosure provides a genetically modified cell that is genetically modified with a recombinant expression vector comprising: a) a nucleotide sequence encoding a CasJ polypeptide of the present disclosure; b) a nucleotide sequence encoding a CasJ guide RNA of the present disclosure; and c) a nucleotide sequence encoding a donor template.

A cell that serves as a recipient for a CasJ polypeptide of the present disclosure and/or a nucleic acid comprising a nucleotide sequence encoding a CasJ polypeptide of the present disclosure and/or a CasJ guide RNA of the present disclosure, can be any of a variety of cells, including, e.g., in vitro cells; in vivo cells; ex vivo cells; primary cells; cancer cells; animal cells; plant cells; algal cells; fungal cells; etc. A cell that serves as a recipient for a CasJ polypeptide of the present disclosure and/or a nucleic acid comprising a nucleotide sequence encoding a CasJ polypeptide of the present disclosure and/or a CasJ guide RNA of the present disclosure is referred to as a "host cell" or a "target cell." A host cell or a target cell can be a recipient of a CasJ system of the present disclosure. A host cell or a target cell can be a recipient of a CasJ RNP of the present disclosure. A host cell or a target cell can be a recipient of a single component of a CasJ system of the present disclosure.

Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatos, rice, cassava, sugarcane, pumpkin, hay, potatos, cotton, *Brassica* sp. including oilseed rape, sorghum, sugarbeet, *Cannabis*, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens,* C. agardh, and the like), seaweeds (e.g., kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be an in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbial cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g., an embryonic stem (ES) cell, an induced pluripotent stem (iPS) cell; a germ cell (e.g., an oocyte, a sperm, an oogonia, a spermatogonia, etc.); a somatic cell, e.g., a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell. Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some embodiments, the stem cell is a hematopoietic stem cell (HSC). HSCs are mesoderm-derived cells that can be isolated from bone marrow, blood, cord blood, fetal liver and yolk sac. HSCs are characterized as $CD34^+$ and CD3. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other embodiments, the stem cell is a neural stem cell (NSC). NSCs are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, Chinese artichoke (crosnes), Chinese cabbage, Chinese celery, Chinese chives, choy sum, chrysanthemum leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

A cell is in some cases an arthropod cell. For example, the cell can be a cell of a suborder, a family, a sub-family, a group, a sub-group, or a species of, e.g., Chelicerata, Myriapodia, Hexipodia, Arachnida, Insecta, Archaeognatha, Thysanura, Palaeoptera, Ephemeroptera, Odonata, Anisoptera, Zygoptera, Neoptera, Exopterygota, Plecoptera, Embioptera, Orthoptera, Zoraptera, Dermaptera, Dictyoptera, Notoptera, Grylloblattidae, Mantophasmatidae, Phasmatodea, Blattaria, Isoptera, Mantodea, Parapneuroptera, Psocoptera, Thysanoptera, Phthiraptera, Hemiptera, Endopterygota or Holometabola, Hymenoptera, Coleoptera, Strepsiptera, Raphidioptera, Megaloptera, Neuroptera, Mecoptera, Siphonaptera, Diptera, Trichoptera, or Lepidoptera.

A cell is in some cases an insect cell. For example, in some cases, the cell is a cell of a mosquito, a grasshopper, a true bug, a fly, a flea, a bee, a wasp, an ant, a louse, a moth, or a beetle.

The present disclosure provides a kit comprising a CasJ system of the present disclosure, or a component of a CasJ system of the present disclosure. A kit of the present disclosure can comprise: a) a CasJ polypeptide of the present disclosure and a CasJ guide RNA; b) a CasJ polypeptide of the present disclosure, a CasJ guide RNA, and a donor template nucleic acid; c) a CasJ fusion polypeptide of the present disclosure and a CasJ guide RNA; d) a CasJ fusion polypeptide of the present disclosure, a CasJ guide RNA, and a donor template nucleic acid; e) an mRNA encoding a CasJ polypeptide of the present disclosure; and a CasJ guide RNA; f) an mRNA encoding a CasJ polypeptide of the present disclosure, a CasJ guide RNA, and a donor template nucleic acid; g) an mRNA encoding a CasJ fusion polypeptide of the present disclosure; and a CasJ guide RNA; h) an mRNA encoding a CasJ fusion polypeptide of the present disclosure, a CasJ guide RNA, and a donor template nucleic acid; i) a recombinant expression vector comprising a nucleotide sequence encoding a CasJ polypeptide of the present disclosure and a nucleotide sequence encoding a CasJ guide RNA; j) a recombinant expression vector comprising a nucleotide sequence encoding a CasJ polypeptide of the present disclosure, a nucleotide sequence encoding a CasJ guide RNA, and a nucleotide sequence encoding a donor template nucleic acid; k) a recombinant expression vector comprising a nucleotide sequence encoding a CasJ fusion polypeptide of the present disclosure and a nucleotide sequence encoding a CasJ guide RNA; l) a recombinant expression vector comprising a nucleotide sequence encoding a CasJ fusion polypeptide of the present disclosure, a nucleotide sequence encoding a CasJ guide RNA, and a nucleotide sequence encoding a donor template nucleic acid; m) a first recombinant expression vector comprising a nucleotide sequence encoding a CasJ polypeptide of the present disclosure, and a second recombinant expression vector comprising a nucleotide sequence encoding a CasJ guide RNA; n) a first recombinant expression vector comprising a nucleotide sequence encoding a CasJ polypeptide of the present disclosure, and a second recombinant expression vector comprising a nucleotide sequence encoding a CasJ guide RNA; and a donor template nucleic acid; o) a first recombinant expression vector comprising a nucleotide sequence encoding a CasJ fusion polypeptide of the present disclosure, and a second recombinant expression vector comprising a nucleotide sequence encoding a CasJ guide RNA; p) a first recombinant expression vector comprising a nucleotide sequence encoding a CasJ fusion polypeptide of the present disclosure, and a second recombinant expression vector comprising a nucleotide sequence encoding a CasJ guide RNA; and a donor template nucleic acid; q) a recombinant expression vector comprising a nucleotide sequence encoding a CasJ polypeptide of the present disclosure, a nucleotide sequence encoding a first CasJ guide RNA, and a nucleotide sequence encoding a second CasJ guide RNA; or r) a recombinant expression vector comprising a nucleotide sequence encoding a CasJ fusion polypeptide of the present disclosure, a nucleotide sequence encoding a first CasJ guide RNA, and a nucleotide sequence encoding a second CasJ guide RNA; or some variation of one of (a) through (r).

A kit of the present disclosure can comprise: a) a component, as described above, of a CasJ system of the present disclosure, or can comprise a CasJ system of the present disclosure; and b) one or more additional reagents, e.g., i) a buffer; ii) a protease inhibitor; iii) a nuclease inhibitor; iv) a reagent required to develop or visualize a detectable label; v) a positive and/or negative control target DNA; vi) a positive and/or negative control CasJ guide RNA; and the like. A kit of the present disclosure can comprise: a) a component, as described above, of a CasJ system of the present disclosure, or can comprise a CasJ system of the present disclosure; and b) a therapeutic agent. A kit of the present disclosure can comprise a recombinant expression vector comprising: a) an insertion site for inserting a nucleic acid comprising a nucleotide sequence encoding a portion of a CasJ guide RNA that hybridizes to a target nucleotide sequence in a target nucleic acid; and b) a nucleotide sequence encoding the CasJ-binding portion of a CasJ guide RNA. A kit of the present disclosure can comprise a recombinant expression vector comprising: a) an insertion site for inserting a nucleic acid comprising a nucleotide sequence encoding a portion of a CasJ guide RNA that hybridizes to a target nucleotide sequence in a target nucleic acid; b) a nucleotide sequence encoding the CasJ-binding portion of a CasJ guide RNA; and c) a nucleotide sequence encoding a CasJ polypeptide of the present disclosure.

A CasJ polypeptide of the present disclosure, or a CasJ fusion polypeptide of the present disclosure, finds use in a variety of methods (e.g., in combination with a CasJ guide RNA and in some cases further in combination with a donor template). For example, a CasJ polypeptide of the present disclosure can be used to (i) modify (e.g., cleave, e.g., nick; methylate; etc.) target nucleic acid (DNA or RNA; single stranded or double stranded); (ii) modulate transcription of a target nucleic acid; (iii) label a target nucleic acid; (iv) bind a target nucleic acid (e.g., for purposes of isolation, labeling, imaging, tracking, etc.); (v) modify a polypeptide (e.g., a histone) associated with a target nucleic acid; and the like. Thus, the present disclosure provides a method of modifying a target nucleic acid. In some cases, a method of the present disclosure for modifying a target nucleic acid comprises contacting the target nucleic acid with: a) a CasJ polypeptide of the present disclosure; and b) one or more (e.g., two) CasJ guide RNAs. In some cases, a method of the present disclosure for modifying a target nucleic acid comprises contacting the target nucleic acid with: a) a CasJ polypeptide of the present disclosure; b) a CasJ guide RNA; and c) a donor nucleic acid (e.g, a donor template). In some cases, the contacting step is carried out in a cell in vitro. In some cases, the contacting step is carried out in a cell in vivo. In some cases, the contacting step is carried out in a cell ex vivo.

Because a method that uses a CasJ polypeptide includes binding of the CasJ polypeptide to a particular region in a target nucleic acid (by virtue of being targeted there by an associated CasJ guide RNA), the methods are generally referred to herein as methods of binding (e.g., a method of binding a target nucleic acid). However, it is to be understood that in some cases, while a method of binding may result in nothing more than binding of the target nucleic acid, in other cases, the method can have different final results (e.g., the method can result in modification of the target nucleic acid, e.g., cleavage/methylation/etc, modulation of transcription from the target nucleic acid; modulation of translation of the target nucleic acid; genome editing; modulation of a protein associated with the target nucleic acid; isolation of the target nucleic acid; etc.).

For examples of suitable methods, see, for example, Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5): 1173-83; Wang et al., Cell. 2013 May 9; 153(4): 910-8; Auer et al, Genome Res. 2013 Oct. 31; Chen et al., Nucleic Acids Res. 2013 Nov. 1; 41(20):e19; Cheng et al., Cell Res. 2013 October; 23(10): 1163-71; Cho et al., Genetics. 2013 November; 195(3): 1177-80; DiCarlo et al., Nucleic Acids Res. 2013 April; 41(7):4336-43; Dickinson et al., Nat Methods. 2013 October; 10(10): 1028-34; Ebina et al., Sci Rep. 2013; 3:2510; Fujii et al, Nucleic Acids Res. 2013 Nov. 1; 41(20):e187; Hu et al., Cell Res. 2013 November; 23(11): 1322-5; Jiang et al., Nucleic Acids Res. 2013 Nov. 1; 41(20):e188; Larson et al, Nat Protoc. 2013 November; 8(11):2180-96; Mali et. at., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6): 1380-9; Upadhyay et al., G3 (Bethesda). 2013 Dec. 9; 3(12):2233-8; Walsh et al., Proc Natl Acad Sci USA. 2013 Sep. 24; 110(39): 15514-5; Xie et al., Mol Plant. 2013 Oct. 9; Yang et al., Cell. 2013 Sep. 12; 154(6): 1370-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; each of which is hereby incorporated by reference in its entirety.

For example, the present disclosure provides (but is not limited to) methods of cleaving a target nucleic acid; methods of editing a target nucleic acid; methods of modulating transcription from a target nucleic acid; methods of isolating a target nucleic acid, methods of binding a target nucleic acid, methods of imaging a target nucleic acid, methods of modifying a target nucleic acid, and the like.

As used herein, the terms/phrases "contact a target nucleic acid" and "contacting a target nucleic acid", for example, with a CasJ polypeptide or with a CasJ fusion polypeptide, etc., encompass all methods for contacting the target nucleic acid. For example, a CasJ polypeptide can be provided to a cell as protein, RNA (encoding the CasJ polypeptide), or DNA (encoding the CasJ polypeptide); while a CasJ guide RNA can be provided as a guide RNA or as a nucleic acid encoding the guide RNA. As such, when, for example, performing a method in a cell (e.g., inside of a cell in vitro, inside of a cell in vivo, inside of a cell ex vivo), a method that includes contacting the target nucleic acid encompasses the introduction into the cell of any or all of the components in their active/final state (e.g., in the form of a protein(s) for CasJ polypeptide; in the form of a protein for a CasJ fusion polypeptide; in the form of an RNA in some cases for the guide RNA), and also encompasses the introduction into the cell of one or more nucleic acids encoding one or more of the components (e.g., nucleic acid(s) comprising nucleotide sequence(s) encoding a CasJ polypeptide or a CasJ fusion polypeptide, nucleic acid(s) comprising nucleotide sequence(s) encoding guide RNA(s), nucleic acid comprising a nucleotide sequence encoding a donor template, and the like). Because the methods can also be performed in vitro outside of a cell, a method that includes contacting a target nucleic acid, (unless otherwise specified) encompasses contacting outside of a cell in vitro, inside of a cell in vitro, inside of a cell in vivo, inside of a cell ex vivo, etc.

In some cases, a method of the present disclosure for modifying a target nucleic acid comprises contacting a target nucleic acid with a CasJ polypeptide of the present disclosure, or with a CasJ fusion polypeptide of the present disclosure. In some cases, a method of the present disclosure for modifying a target nucleic acid comprises contacting a target nucleic acid with a CasJ polypeptide and a CasJ guide RNA. In some cases, a method of the present disclosure for modifying a target nucleic acid comprises contacting a target nucleic acid with a CasJ polypeptide, a first CasJ guide RNA, and a second CasJ guide RNA In some cases, a method of the present disclosure for modifying a target nucleic acid comprises contacting a target nucleic acid with a CasJ polypeptide of the present disclosure and a CasJ guide RNA and a DNA donor template.

A CasJ polypeptide of the present disclosure, or a CasJ fusion polypeptide of the present disclosure, when bound to a CasJ guide RNA, can bind to a target nucleic acid, and in some cases, can bind to and modify a target nucleic acid. A target nucleic acid can be any nucleic acid (e.g., DNA, RNA), can be double stranded or single stranded, can be any type of nucleic acid (e.g., a chromosome (genomic DNA), derived from a chromosome, chromosomal DNA, plasmid, viral, extracellular, intracellular, mitochondrial, chloroplast, linear, circular, etc.) and can be from any organism (e.g., as long as the CasJ guide RNA comprises a nucleotide sequence that hybridizes to a target sequence in a target nucleic acid, such that the target nucleic acid can be targeted).

A target nucleic acid can be DNA or RNA. A target nucleic acid can be double stranded (e.g., dsDNA, dsRNA) or single stranded (e.g., ssRNA, ssDNA). In some cases, a target nucleic acid is single stranded. In some cases, a target nucleic acid is a single stranded RNA (ssRNA). In some cases, a target ssRNA (e.g., a target cell ssRNA, a viral ssRNA, etc.) is selected from: mRNA, rRNA, tRNA, non-coding RNA (ncRNA), long non-coding RNA (lncRNA), and microRNA (miRNA). In some cases, a target nucleic acid is a single stranded DNA (ssDNA) (e.g., a viral DNA). As noted above, in some cases, a target nucleic acid is single stranded.

A target nucleic acid can be located anywhere, for example, outside of a cell in vitro, inside of a cell in vitro, inside of a cell in vivo, inside of a cell ex vivo. Suitable target cells (which can comprise target nucleic acids such as genomic DNA) include, but are not limited to: a bacterial cell; an archaeal cell; a cell of a single-cell eukaryotic organism; a plant cell; an algal cell, e.g., *Botryococcus braunii, Chlamydomonas reinhardtii, Nannochloropsis gaditana, Chlorella pyrenoidosa, Sargassum patens*, C. agardh, and the like; a fungal cell (e.g., a yeast cell); an animal cell; a cell from an invertebrate animal (e.g., fruit fly, a cnidarian, an echinoderm, a nematode, etc.); a cell of an insect (e.g., a mosquito; a bee; an agricultural pest; etc.); a cell of an arachnid (e.g., a spider; a tick; etc.); a cell from a vertebrate animal (e.g., a fish, an amphibian, a reptile, a bird, a mammal); a cell from a mammal (e.g., a cell from a rodent; a cell from a human; a cell of a non-human mammal; a cell of a rodent (e.g., a mouse, a rat); a cell of a lagomorph (e.g., a rabbit); a cell of an ungulate (e.g., a cow, a horse, a camel, a llama, a vicuna, a sheep, a goat, etc.); a cell of a marine mammal (e.g., a whale, a seal, an elephant seal, a dolphin, a sea lion; etc.) and the like. Any type of cell may be of interest (e.g., a stem cell, e.g., an embryonic stem (ES) cell, an induced pluripotent stem (iPS) cell, a germ cell (e.g., an oocyte, a sperm, an oogonia, a spermatogonia, etc.), an adult stem cell, a somatic cell, e.g., a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.).

Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e., splittings, of the culture. For example, primary cultures are cultures that may have been passaged 0 times, 1 time, 2 times, 4 times, 5 times, 10 times, or 15 times, but not enough times go through the crisis stage. Typically, the primary cell lines are maintained for fewer than 10 passages in vitro. Target cells can be unicellular organisms and/or can be grown in culture. If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. can be conveniently harvested by biopsy.

In some of the above applications, the subject methods may be employed to induce target nucleic acid cleavage, target nucleic acid modification, and/or to bind target nucleic acids (e.g., for visualization, for collecting and/or analyzing, etc.) in mitotic or post-mitotic cells in vivo and/or ex vivo and/or in vitro (e.g., to disrupt production of a protein encoded by a targeted mRNA, to cleave or otherwise modify target DNA, to genetically modify a target cell, and the like). Because the guide RNA provides specificity by hybridizing to target nucleic acid, a mitotic and/or post-mitotic cell of interest in the disclosed methods may include a cell from any organism (e.g., a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens*, C. agardh, and the like, a fungal cell (e.g., a yeast cell), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal, a cell from a rodent, a cell from a human, etc.). In some cases, a subject CasJ protein (and/or nucleic acid encoding the protein such as DNA and/or RNA), and/or CasJ guide RNA (and/or a DNA encoding the guide RNA), and/or donor template, and/or RNP can be introduced into an individual (e.g., the target cell can be in vivo) (e.g., a mammal, a rat, a mouse, a pig, a primate, a non-human primate, a human, etc.). In some case, such an administration can be for the purpose of treating and/or preventing a disease, e.g., by editing the genome of targeted cells.

Plant cells include cells of a monocotyledon, and cells of a dicotyledon. The cells can be root cells, leaf cells, cells of the xylem, cells of the phloem, cells of the cambium, apical meristem cells, parenchyma cells, collenchyma cells, sclerenchyma cells, and the like. Plant cells include cells of agricultural crops such as wheat, corn, rice, sorghum, millet, soybean, etc. Plant cells include cells of agricultural fruit and nut plants, e.g., plant that produce apricots, oranges, lemons, apples, plums, pears, almonds, etc.

Non-limiting examples of cells can be found in the section "Modified host cells".

Guided by a CasJ dual or single guide RNA, a CasJ protein in some cases generates site-specific double strand breaks (DSBs) or single strand breaks (SSBs) (e.g., when the CasJ protein is a nickase variant) within double-stranded DNA (dsDNA) target nucleic acids, which are repaired either by non-homologous end joining (NHEJ) or homology-directed repair (HDR).

In some cases, contacting a target DNA (with a CasJ protein and a CasJ guide RNA) occurs under conditions that are permissive for nonhomologous end joining or homology-directed repair. Thus, in some cases, a subject method includes contacting the target DNA with a donor polynucleotide or DNA donor template (e.g., by introducing the donor polynucleotide or DNA donor template into a cell), wherein the donor polynucleotide or DNA donor template, a portion of the donor polynucleotide or DNA donor template, a copy of the donor polynucleotide or DNA donor template, or a portion of a copy of the donor polynucleotide or DNA donor template integrates into the target DNA. In some cases, the method does not comprise contacting a cell with a donor polynucleotide or DNA donor template, and the target DNA is modified such that nucleotides within the target DNA are deleted.

In some cases, CasJ guide RNA (or DNA encoding same) and a CasJ protein (or a nucleic acid encoding same, such as an RNA or a DNA, e.g, one or more expression vectors) are coadministered (e.g., contacted with a target nucleic acid, administered to cells, etc.) with a donor polynucleotide sequence or DNA donor template that includes at least a segment with homology to the target DNA sequence, the subject methods may be used to add, e.g., insert or replace, nucleic acid material to a target DNA sequence (e.g., to "knock in" a nucleic acid, e.g., one that encodes for a protein, an siRNA, an miRNA, etc.), to add a tag (e.g., 6×His, a fluorescent protein (e.g., a green fluorescent protein; a yellow fluorescent protein, etc.), hemagglutinin (HA), FLAG, etc.), to add a regulatory sequence to a gene (e.g., promoter, polyadenylation signal, internal ribosome entry sequence (IRES), 2A peptide, start codon, stop codon, splice signal, localization signal, etc.), to modify a nucleic acid sequence (e.g., introduce a mutation, remove a disease causing mutation by introducing a correct sequence), and the like. As such, a complex comprising a CasJ guide RNA and CasJ protein is useful in any in vitro or in vivo application in which it is desirable to modify DNA in a site-specific, i.e., "targeted", way, for example gene knock-out, gene knock-in, gene editing, gene tagging, etc., as used in, for example, conferring a trait, gene therapy, e.g., to treat a disease or as an antiviral, antipathogenic, or anticancer therapeutic, the production of genetically modified organisms in agriculture, the large scale production of proteins by cells for therapeutic, diagnostic, or research purposes, the induction of iPS cells, biological research, the targeting of genes of pathogens for deletion or replacement, etc.

In applications in which it is desirable to insert a polynucleotide sequence into the genome where a target sequence is cleaved, a donor polynucleotide or DNA donor template (a nucleic acid comprising a donor sequence) can also be provided to the cell. By a "donor sequence" or "donor polynucleotide" or "donor template" or "DNA donor template" it is meant a nucleic acid sequence to be inserted at the site cleaved by the CasJ protein (e.g., after dsDNA cleavage, after nicking a target DNA, after dual nicking a target DNA, and the like). The donor polynucleotide or DNA donor template can contain sufficient homology to a genomic sequence at the target site, e.g., 70%, 80%, 85%, 90%, 95%, or 100% homology with the nucleotide sequences flanking the target site, e.g., within about 50 bases or less of the target site, e.g., within about 30 bases, within about 15 bases, within about 10 bases, within about 5 bases, or immediately flanking the target site, to support homology-directed repair between it and the genomic sequence to which it bears homology. Approximately 25, 50, 100, or 200 nucleotides, or more than 200 nucleotides, of sequence homology between a donor and a genomic sequence (or any integral value between 10 and 200 nucleotides, or more) can support homology-directed repair. Donor polynucleotides or DNA donor template can be of any length, e.g., 10 nucleotides or more, 50 nucleotides or more, 100 nucleotides or more, 250 nucleotides or more, 500 nucleotides or more, 1000 nucleotides or more, 5000 nucleotides or more, etc.

The donor sequence or DNA donor template is typically not identical to the genomic sequence that it replaces. Rather, the donor sequence or DNA donor template may contain at least one or more single base changes, insertions, deletions, inversions or rearrangements with respect to the genomic sequence, so long as sufficient homology is present to support homology-directed repair (e.g., for gene correction, e.g., to convert a disease-causing base pair to a non-disease-causing base pair). In some embodiments, the donor sequence or DNA donor template comprises a nonhomologous sequence flanked by two regions of homology, such that homology-directed repair between the target DNA region and the two flanking sequences results in insertion of the non-homologous sequence at the target region. Donor sequences or DNA donor template may also comprise a vector backbone containing sequences that are not homologous to the DNA region of interest and that are not intended for insertion into the DNA region of interest. Generally, the homologous region(s) of a donor sequence or DNA donor template will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

The donor sequence or DNA donor template may comprise certain sequence differences as compared to the genomic sequence, e.g., restriction sites, nucleotide polymorphisms, selectable markers (e.g., drug resistance genes, fluorescent proteins, enzymes etc.), etc., which may be used to assess for successful insertion of the donor sequence at the cleavage site or in some cases may be used for other purposes (e.g., to signify expression at the targeted genomic locus). In some cases, if located in a coding region, such nucleotide sequence differences will not change the amino acid sequence, or will make silent amino acid changes (e.g., changes which do not affect the structure or function of the protein). Alternatively, these sequences differences may include flanking recombination sequences such as FLPs, loxP sequences, or the like, that can be activated at a later time for removal of the marker sequence.

In some cases, the donor sequence or DNA donor template is provided to the cell as single-stranded DNA. In some cases, the donor sequence or DNA donor template is provided to the cell as double-stranded DNA. It may be introduced into a cell in linear or circular form. If introduced in linear form, the ends of the donor sequence may be protected (e.g., from exonucleolytic degradation) by any convenient method and such methods are known to those of skill in the art. For example, one or more dideoxynucleotide residues can be added to the 3' terminus of a linear molecule and/or self-complementary oligonucleotides can be ligated to one or both ends. See, for example, Chang et al. (1987) Proc. Natl. Acad Sci USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphor amidates, and O-methyl ribose or deoxyribose residues. As an alternative to protecting the termini of a linear donor sequence, additional lengths of sequence may be included outside of the regions of homology that can be degraded without impacting recombination. A donor sequence or DNA donor template can be introduced into a cell as part of a vector molecule having additional sequences such as, for example, replication origins, promoters and genes encoding antibiotic resistance. Moreover, donor sequences can be introduced as naked nucleic acid, as nucleic acid complexed with an agent such as a liposome or poloxamer, or can be delivered by viruses (e.g., adenovirus, AAV, geminiviruses), as described elsewhere herein for nucleic acids encoding a CasJ guide RNA and/or a CasJ fusion polypeptide and/or donor polynucleotide.

In some embodiments the disclosed RNA-guided nucleases can be used in systems and methods for detecting one or more specific target DNA molecules in a sample. Examples of target DNA molecule detection schemes that were implemented with distinct RNA guided nucleases are described in in US20190241954, which is hereby incorporated by reference in its entirety. In certain embodiments, the methods and reagents (e.g., reporter molecules) described in US20190241954 and incorporated herein by reference can be adapted for use with the CasJ polypeptides, CasJ fusion polypeptides, and CasJ guide RNA molecules disclosed herein.

Guide RNAs for a CasJ polypeptide or fusion polypeptide are designed to recognize a target DNA molecule having target sequences in samples potentially or suspected of having the target DNA of interest. The DNA having the target sequence can be single stranded or double stranded. If the sample contains the target DNA molecule, binding of the target DNA molecule by the CasJ guide RNA/CasJ polypeptide or fusion polypeptide complex will trigger the CasJ polypeptide or fusion polypeptide's collateral nuclease activity (i.e., cleavage of a single stranded DNA (ssDNA) that does not contain the target DNA sequences). Consequently, a DNA-based reporter molecule produces an output following cleavage by the CasJ polypeptide or fusion polypeptide collateral nuclease activity that can be assayed. Presence or absence of the output, therefore, indicates presence or absence of a target DNA molecule having the target DNA sequence in the sample.

In some cases, a subject method includes a step of measuring (e.g., measuring a detectable signal produced by CasJ-mediated ssDNA cleavage). Because a CasJ cleaves non-targeted ssDNA once activated, which occurs when a guide RNA hybridizes with a target DNA in the presence of a CasJ, a detectable signal can be any signal that is produced when ssDNA is cleaved. In certain embodiments, the reporter molecule is a ssDNA molecule that further comprises a detectable label. In certain embodiments, the detectable label is covalently linked to the ssDNA. For example, in some cases the step of measuring can include one or more of: gold nanoparticle based detection (e.g., see Xu et al., Angew Chem Int Ed Engl. 2007; 46(19):3468-70; and Xia et al., Proc Natl Acad Sci USA. 2010 Jun. 15; 107(24): 10837-41), fluorescence polarization, colloid phase transition/dispersion (e.g., Baksh et al., Nature. 2004 Jan. 8; 427(6970):139-41), electrochemical detection, semiconductor-based sensing (e.g., Rothberg et al., Nature. 2011 Jul. 20; 475(7356):348-52; e.g., one could use a phosphatase to generate a pH change after ssDNA cleavage reactions, by opening 2'-3' cyclic phosphates, and by releasing inorganic phosphate into solution), and detection of a labeled detector ssDNA (DNA reporter molecule). The readout of such detection methods can be any convenient readout. Examples of possible readouts include but are not limited to: a measured amount of detectable fluorescent signal; a visual analysis of bands on a gel (e.g., bands that represent cleaved product versus uncleaved substrate), a visual or sensor based detection of the presence or absence of a color (i.e., color detection method), and the presence or absence of (or a particular amount of) an electrical signal.

The measuring can in some cases be quantitative, e.g., in the sense that the amount of signal detected can be used to determine the amount of a target DNA molecule present in the sample. The measuring can in some cases be qualitative, e.g., in the sense that the presence or absence of detectable signal can indicate the presence or absence of a target DNA molecule (e.g., virus, cDNA from a viral RNA, SNP, etc.). In some cases, a detectable signal will not be present (e.g., above a given threshold level) unless the target DNA(s) (e.g., virus, cDNA from a viral RNA, SNP, etc.) is present above a particular threshold concentration. In some cases, the threshold of detection can be titrated by modifying the amount of CasJ, guide RNA, sample volume, and/or detector ssDNA (if one is used). As such, for example, as would be understood by one of ordinary skill in the art, a number of controls can be used if desired in order to set up one or more reactions, each set up to detect a different threshold level of target DNA, and thus such a series of reactions could be used to determine the amount of a target DNA molecule present in a sample (e.g., one could use such a series of reactions to determine that a target DNA molecule is present in the sample "at a concentration of at least X"). The compositions and methods of this disclosure can be used to detect any DNA target, including DNA targets obtained from RNA targets. For example, any virus that integrates nucleic acid material into the genome can be detected because a subject sample can include cellular genomic DNA, and the guide RNA can be designed to detect integrated nucleotide sequence.

In some cases, a method of the present disclosure can be used to determine the amount of a target DNA molecule in a sample (e.g., a sample comprising the target DNA molecules and a plurality of non-target DNAs). Determining the amount of a target DNA molecule in a sample can comprise comparing the amount of detectable signal generated from a test sample to the amount of detectable signal generated from a reference sample. Determining the amount of a target DNA molecule in a sample can comprise: measuring the detectable signal to generate a test measurement; measuring a detectable signal produced by a reference sample to generate a reference measurement; and comparing the test measurement to the reference measurement to determine an amount of a target DNA molecule present in the sample.

For example, in some cases, a method of the present disclosure for determining the amount of a target DNA molecule in a sample comprises: a) contacting the sample (e.g., a sample comprising the target DNA and a plurality of non-target DNAs) with: (i) a guide RNA that hybridizes with the target DNA, (ii) a CasJ that cleaves target DNAs present in the sample that hybridize to the guide RNA, and (iii) a reporter molecule (e.g., a detector ssDNA); b) measuring a detectable signal produced by CasJ-mediated ssDNA cleavage (e.g., cleavage of the detector ssDNA), generating a test measurement; c) measuring a detectable signal produced by a reference sample to generate a reference measurement; and d) comparing the test measurement to the reference measurement to determine an amount of target DNA present in the sample.

As another example, in some cases, a method of the present disclosure for determining the amount of a target DNA molecule in a sample comprises: a) contacting the sample (e.g., a sample comprising the target DNA molecule and a plurality of non-target DNAs) with: i) a precursor CasJ guide RNA array comprising two or more guide RNAs each of which has a different guide sequence; (ii) a CasJ that cleaves the precursor guide RNA array into individual guide RNAs, and also cleaves RNAs of the sample; and (iii) a DNA reporter molecule (e.g., a detector ssDNA); b) measuring a detectable signal produced by CasJ-mediated ssDNA cleavage (e.g., cleavage of the detector ssDNA), generating a test measurement; c) measuring a detectable signal produced by each of two or more reference samples to generate two or more reference measurements; and d) comparing the test measurement to the reference measurements to determine an amount of target DNA present in the sample.

In some cases, a subject method includes contacting a sample (e.g., a sample comprising a target DNA molecule and a plurality of non-target ssDNAs) with: i) a CasJ polypeptide; ii) a CasJ guide RNA (or precursor guide RNA array); and iii) a DNA-based reporter (detector DNA) that is single stranded and does not hybridize with the guide sequence of the guide RNA. For example, in some cases, a subject method includes contacting a sample with a labeled single stranded reporter DNA molecule (detector ssDNA) that includes a fluorescence-emitting dye pair; the CasJ cleaves the labeled detector ssDNA after it is activated (by binding to the guide RNA in the context of the guide RNA hybridizing to a target DNA); and the detectable signal that is measured is produced by the fluorescence-emitting dye pair. For example, in some cases, a subject method includes contacting a sample with a labeled detector ssDNA comprising a fluorescence resonance energy transfer (FRET) pair or a quencher/fluor pair, or both. In some cases, a subject method includes contacting a sample with a DNA reporter molecule comprising a detectably labeled ssDNA comprising a FRET pair. In some cases, a subject method includes contacting a sample with a DNA reporter molecule comprising a detectably labeled ssDNA comprising a fluor/quencher pair.

In certain embodiments, fluorescence-emitting dye pairs used in a DNA reporter molecule comprise a FRET pair or a quencher/fluor pair. In both cases of a FRET pair and a quencher/fluor pair, the emission spectrum of one of the dyes overlaps a region of the absorption spectrum of the other dye in the pair. As used herein, the term "fluorescence-emitting dye pair" is a generic term used to encompass both a "fluorescence resonance energy transfer (FRET) pair" and a "quencher/fluor pair. The term "fluorescence-emitting dye pair" is used interchangeably with the phrase "a FRET pair and/or a quencher/fluor pair."

In some cases (e.g., when the detector ssDNA includes a FRET pair) the DNA reporter molecule comprising a detectably labeled ssDNA produces an amount of detectable signal prior to being cleaved, and the amount of detectable signal that is measured is reduced when the detectably labeled ssDNA is cleaved. In some cases, the labeled detector ssDNA produces a first detectable signal prior to being cleaved (e.g., from a FRET pair) and a second detectable signal when the detectably labeled ssDNA is cleaved (e.g., from a quencher/fluor pair). As such, in some cases, the detectably labeled ssDNA comprises a FRET pair and a quencher/fluor pair.

In some cases, the detectably labeled detector ssDNA comprises a FRET pair. FRET is a process by which radiationless transfer of energy occurs from an excited state fluorophore to a second chromophore in close proximity The range over which the energy transfer can take place is limited to approximately 10 nanometers (100 angstroms), and the efficiency of transfer is extremely sensitive to the separation distance between fluorophores. Thus, as used herein, the term "FRET" ("fluorescence resonance energy transfer"; also known as "Forster resonance energy transfer") refers to a physical phenomenon involving a donor fluorophore and a matching acceptor fluorophore selected so that the emission spectrum of the donor overlaps the excitation spectrum of the acceptor, and further selected so that when donor and acceptor are in close proximity (usually 10 nm or less) to one another, excitation of the donor will cause excitation of and emission from the acceptor, as some of the energy passes from donor to acceptor via a quantum coupling effect. Thus, a FRET signal serves as a proximity gauge of the donor and acceptor; only when they are in close proximity to one another is a signal generated. The FRET donor moiety (e.g., donor fluorophore) and FRET acceptor moiety (e.g., acceptor fluorophore) are collectively referred to herein as a "FRET pair".

The donor-acceptor pair (a FRET donor moiety and a FRET acceptor moiety) is referred to herein as a "FRET pair" or a "signal FRET pair." Thus, in some cases, a subject labeled detector ssDNA includes two signal partners (a signal pair), when one signal partner is a FRET donor moiety and the other signal partner is a FRET acceptor moiety. A subject labeled detector ssDNA that includes such a FRET pair (a FRET donor moiety and a FRET acceptor moiety) will thus exhibit a detectable signal (a FRET signal) when the signal partners are in close proximity (e.g., while on the same DNA molecule), but the signal will be reduced (or absent) when the partners are separated (e.g., after cleavage of the detectably labelled ssDNA molecule by a CasJ polypeptide or fusion polypeptide/guide RNA complex associated with a DNA target molecule).

FRET donor and acceptor moieties (FRET pairs) will be known to one of ordinary skill in the art and any convenient FRET pair (e.g., any convenient donor and acceptor moiety pair) can be used. Examples of suitable FRET pairs include but are not limited to ECFP-EYFP, mTurquoise2-sEYFP, mTurquoise2-mVenus, Clover-mRuby2, mClover3-mRuby3, mNeonGreen-mRuby3, eqFP650-iRFP, mAmetrine-tdTomato, LSSmOrange-mKate2, EGFP-sREACh, EGFP-ShadowG, EGFP-activated PA-GFP, EGFP-Phanta, mTagBFP-sfGFP, mVenus-mKOK, and CyOFP1-mCardinal. See also: Bajar et al. Sensors (Basel). 2016 Sep. 14; 16(9); and Abraham et al. PLoS One. 2015 Aug. 3; 10(8):e0134436.

In some cases, a detectable signal that can be assayed is produced when the DNA reporter molecule comprising the labeled detector ssDNA is cleaved (e.g., in some cases, the labeled detector ssDNA comprises a quencher/fluor pair). One signal partner of a signal quenching pair produces a detectable signal and the other signal partner is a quencher moiety that quenches the detectable signal of the first signal partner (i.e., the quencher moiety quenches the signal of the signal moiety such that the signal from the signal moiety is reduced (quenched) when the signal partners are in proximity to one another, e.g., when the signal partners of the signal pair are in close proximity).

For example, in some cases, an amount of detectable signal increases when the DNA reporter molecule comprising the labeled detector ssDNA is cleaved. For example, in some cases, the signal exhibited by one signal partner (a signal moiety) is quenched by the other signal partner (a quencher signal moiety), e.g., when both are present on the same ssDNA molecule prior to cleavage by a CasJ. Such a signal pair is referred to herein as a "quencher/fluor pair", "quenching pair", or "signal quenching pair." For example, in some cases, one signal partner (e.g., the first signal partner) is a signal moiety that produces a detectable signal that is quenched by the second signal partner (e.g., a quencher moiety). The signal partners of such a quencher/fluor pair will thus produce a detectable signal when the partners are separated (e.g., after cleavage of the detector ssDNA by a CasJ polypeptide or fusion polypeptide/guide RNA complex associated with a DNA target molecule, but the signal will be quenched when the partners are in close proximity (e.g., prior to cleavage of the detector ssDNA by a CasJ polypeptide or fusion polypeptide/guide RNA complex associated with a DNA target molecule).

In some cases, the signal moiety used in the DNA reporter molecule is a fluorescent label. In some such cases, the quencher moiety quenches the signal (the light signal) from the fluorescent label (e.g., by absorbing energy in the emission spectra of the label). Thus, when the quencher moiety is not in proximity with the signal moiety, the emission (the signal) from the fluorescent label is detectable because the signal is not absorbed by the quencher moiety. Any convenient donor acceptor pair (signal moiety/quencher moiety pair) can be used and many suitable pairs are known in the art.

In some cases the quencher moiety used in the DNA reporter molecule absorbs energy from the signal moiety (also referred to herein as a "detectable label") and then emits a signal (e.g., light at a different wavelength). Thus, in some cases, the quencher moiety is itself a signal moiety (e.g., a signal moiety can be 6-carboxyfluorescein while the quencher moiety can be 6-carboxy-tetramethylrhodamine), and in some such cases, the pair could also be a FRET pair. In some cases, a quencher moiety is a dark quencher. A dark quencher can absorb excitation energy and dissipate the energy in a different way (e.g., as heat). Thus, a dark quencher has minimal to no fluorescence of its own (does not emit fluorescence). Examples of dark quenchers are further described in U.S. Pat. Nos. 8,822,673 and 8,586,718; U.S. patent publications 20140378330, 20140349295, and 20140194611; and international patent applications: WO200142505 and WO200186001, which are each hereby incorporated by reference in their entirety.

Examples of fluorescent labels that can be used in the DNA reporter molecule include, but are not limited to: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein isothiocyanate (FITC), tetramethylrhodamine (TRITC), Texas Red, Oregon Green, Pacific Blue, Pacific Green, Pacific Orange, quantum dots, and a tethered fluorescent protein.

In some cases, a detectable label that can be used in the DNA reporter molecule is a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, and Pacific Orange.

In some cases, a detectable label that can be used in the DNA reporter molecule is a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, Pacific Orange, a quantum dot, and a tethered fluorescent protein.

Examples of ATTO dyes that can be used in the DNA reporter molecule include, but are not limited to: ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, and ATTO 740.

Examples of AlexaFluor dyes that can be used in the DNA reporter molecule include, but are not limited to: Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, Alexa Fluor® 750, Alexa Fluor® 790, and the like.

Examples of quencher moieties that can be used in the DNA reporter molecule include, but are not limited to: a dark quencher, a Black Hole Quencher® (BHQ®) (e.g., BHQ-0, BHQ-1, BHQ-2, BHQ-3), a Qx1 quencher, an ATTO quencher (e.g., ATTO 540Q, ATTO 580Q, and ATTO 612Q), dimethylaminoazobenzenesulfonic acid (Dabsyl), Iowa Black RQ, Iowa Black FQ, IRDye QC-1, a QSY dye (e.g., QSY 7, QSY 9, QSY 21), AbsoluteQuencher, Eclipse, and metal clusters such as gold nanoparticles, and the like.

In some cases, a quencher moiety that can be used in the DNA reporter molecule is selected from: a dark quencher, a Black Hole Quencher® (BHQ®) (e.g., BHQ-0, BHQ-1, BHQ-2, BHQ-3), a Qx1 quencher, an ATTO quencher (e.g., ATTO 540Q, ATTO 580Q, and ATTO 612Q), dimethylaminoazobenzenesulfonic acid (Dabsyl), Iowa Black RQ, Iowa Black FQ, IRDye QC-1, a QSY dye (e.g., QSY 7, QSY 9, QSY 21), AbsoluteQuencher, Eclipse, and a metal cluster.

Examples of an ATTO quencher that can be used in the DNA reporter molecule include, but are not limited to: ATTO 540Q, ATTO 580Q, and ATTO 612Q. Examples of a Black Hole Quencher® (BHQ®) include, but are not limited to: BHQ-0 (493 nm), BHQ-1 (534 nm), BHQ-2 (579 nm) and BHQ-3 (672 nm).

For examples of some detectable labels (e.g., fluorescent dyes) and/or quencher moieties that can be used in the DNA reporter molecule, are set forth in, Bao et al., Annu Rev Biomed Eng. 2009; 11:25-47; as well as U.S. Pat. Nos. 8,822,673 and 8,586,718; U.S. patent publications 20140378330, 20140349295, 20140194611, 20130323851, 20130224871, 20110223677, 20110190486, 20110172420, 20060179585, and 20030003486; and international patent applications: WO200142505 and WO200186001, all of which are hereby incorporated by reference in their entireties.

In some cases, cleavage of the DNA reporter molecule comprising a labeled detector ssDNA can be detected by measuring a colorimetric read-out. For example, the liberation of a fluorophore (e.g., liberation from a FRET pair, liberation from a quencher/fluor pair, and the like) can result in a wavelength shift (and thus color shift) of a detectable signal. Thus, in some cases, cleavage of a subject labeled detector ssDNA can be detected by a color-shift. Such a shift can be expressed as a loss of an amount of signal of one color (wavelength), a gain in the amount of another color, a change in the ration of one color to another, and the like.

As described above, in some cases, a nucleic acid (e.g., a recombinant expression vector) of the present disclosure (e.g., a nucleic acid comprising a nucleotide sequence encoding a CasJ polypeptide of the present disclosure; a nucleic acid comprising a nucleotide sequence encoding a CasJ fusion polypeptide of the present disclosure; etc.), is used as a transgene to generate a transgenic non-human organism (e.g., a plant) that produces a CasJ polypeptide, or a CasJ fusion polypeptide, of the present disclosure. The present disclosure provides a transgenic-non-human organism comprising a nucleotide sequence encoding a CasJ polypeptide, or a CasJ fusion polypeptide, of the present disclosure.

The present disclosure provides a transgenic non-human animal, which animal comprises a transgene comprising a nucleic acid comprising a nucleotide sequence encoding a CasJ polypeptide or a CasJ fusion polypeptide. In some embodiments, the genome of the transgenic non-human animal comprises a nucleotide sequence encoding a CasJ polypeptide or a CasJ fusion polypeptide, of the present disclosure. In some cases, the transgenic non-human animal is homozygous for the genetic modification. In some cases, the transgenic non-human animal is heterozygous for the genetic modification. In some embodiments, the transgenic non-human animal is a vertebrate, for example, a fish (e.g., salmon, trout, zebra fish, gold fish, puffer fish, cave fish, etc.), an amphibian (frog, newt, salamander, etc.), a bird (e.g., chicken, turkey, etc.), a reptile (e.g., snake, lizard, etc.), a non-human mammal (e.g., an ungulate, e.g., a pig, a cow, a goat, a sheep, etc.; a lagomorph (e.g., a rabbit); a rodent (e.g., a rat, a mouse); a non-human primate; etc.), etc. In some cases, the transgenic non-human animal is an invertebrate. In some cases, the transgenic non-human animal is an insect (e.g., a mosquito; an agricultural pest; etc.). In some cases, the transgenic non-human animal is an arachnid.

Nucleotide sequences encoding a CasJ polypeptide or a CasJ fusion polypeptide, of the present disclosure can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters (e.g., CMV promoter), inducible promoters (e.g., heat shock promoter, tetracycline-regulated promoter, steroid-regulated promoter, metal-regulated promoter, estrogen receptor-regulated promoter, etc.), spatially restricted and/or temporally restricted promoters (e.g., a tissue specific promoter, a cell type specific promoter, etc.), etc.

As described above, in some cases, a nucleic acid (e.g., a recombinant expression vector) of the present disclosure (e.g., a nucleic acid comprising a nucleotide sequence encoding a CasJ polypeptide of the present disclosure; a nucleic acid comprising a nucleotide sequence encoding a CasJ fusion polypeptide of the present disclosure; etc.), is used as a transgene to generate a transgenic plant that produces a CasJ polypeptide, or a CasJ fusion polypeptide, of the present disclosure. The present disclosure provides a transgenic plant comprising a nucleotide sequence encoding a CasJ polypeptide, or a CasJ fusion polypeptide, of the present disclosure. In some embodiments, the genome of the transgenic plant comprises a subject nucleic acid. In some embodiments, the transgenic plant is homozygous for the genetic modification. In some embodiments, the transgenic plant is heterozygous for the genetic modification.

Methods of introducing exogenous nucleic acids into plant cells are well known in the art. Such plant cells are considered "transformed," as defined above. Suitable methods include viral infection (such as double stranded DNA viruses including geminiviruses), transfection, conjugation, protoplast fusion, electroporation, particle gun technology, calcium phosphate precipitation, direct microinjection, silicon carbide whiskers technology, *Agrobacterium*-mediated transformation and the like. The choice of method is generally dependent on the type of cell being transformed and the circumstances under which the transformation is taking place (e.g., in vitro, ex vivo, or in vivo).

Transformation methods based upon the soil bacterium *Agrobacterium tumefaciens* are particularly useful for introducing an exogenous nucleic acid molecule into a vascular plant. The wild type form of *Agrobacterium* contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An *Agrobacterium*-based vector is a modified form of a Ti plasmid, in which the tumor inducing functions are replaced by the nucleic acid sequence of interest to be introduced into the plant host.

*Agrobacterium*-mediated transformation generally employs cointegrate vectors or binary vector systems, in which the components of the Ti plasmid are divided between a helper vector, which resides permanently in the *Agrobacterium* host and carries the virulence genes, and a shuttle vector, which contains the gene of interest bounded by T-DNA sequences. A variety of binary vectors is well known in the art and are commercially available, for example, from Clontech (Palo Alto, Calif.). Methods of coculturing *Agrobacterium* with cultured plant cells or wounded tissue such as leaf tissue, root explants, hypocotyledons, stem pieces or tubers, for example, also are well known in the art. See, e.g., Glick and Thompson, (eds.), Methods in Plant Molecular Biology and Biotechnology, Boca Raton, Fla.: CRC Press (1993).

Microprojectile-mediated transformation also can be used to produce a subject transgenic plant. This method, first described by Klein et al. (Nature 327:70-73 (1987)), relies on microprojectiles such as gold or tungsten that are coated with the desired nucleic acid molecule by precipitation with calcium chloride, spermidine or polyethylene glycol. The microprojectile particles are accelerated at high speed into an angiosperm tissue using a device such as the BIOLISTIC PD-1000 (Biorad; Hercules Calif.). A nucleic acid of the present disclosure (e.g., a nucleic acid (e.g., a recombinant expression vector) comprising a nucleotide sequence encoding a CasJ polypeptide, or a CasJ fusion polypeptide, of the present disclosure) may be introduced into a plant in a manner such that the nucleic acid is able to enter a plant cell(s), e.g., via an in vivo or ex vivo protocol. By "in vivo," it is meant in the nucleic acid is administered to a living body of a plant e.g., infiltration. By "ex vivo" it is meant that cells or explants are modified outside of the plant, and then such cells or organs are regenerated to a plant. A number of vectors suitable for stable transformation of plant cells or for the establishment of transgenic plants have been described, including those described in Weissbach and Weissbach, (1989) Methods for Plant Molecular Biology Academic Press, and Gelvin et al., (1990) Plant Molecular Biology Manual, Kluwer Academic Publishers. Specific examples include those derived from a Ti plasmid of *Agrobacterium tumefaciens*, as well as those disclosed by Herrera-Estrella et al. (1983) Nature 303: 209, Bevan (1984) Nucl Acid Res. 12: 8711-8721, Klee (1985) Bio/Technolo 3: 637-642. Alternatively, non-Ti vectors can be used to transfer the DNA into plants and cells by using free DNA delivery techniques. By using these methods transgenic plants such as wheat, rice (Christou (1991) Bio/Technology 9:957-9 and 4462) and corn (Gordon-Kamm (1990) Plant Cell 2: 603-618) can be produced. An immature embryo can also be a good target tissue for monocots for direct DNA delivery techniques by using the particle gun (Weeks et al. (1993) Plant Physiol 102: 1077-1084; Vasil (1993) Bio/Technolo 10: 667-674; Wan and Lemeaux (1994) Plant Physiol 104: 37-48 and for *Agrobacterium*-mediated DNA transfer (Ishida et al. (1996) Nature Biotech 14: 745-750). Methods for introduction of DNA into chloroplasts are biolistic bombardment, polyethylene glycol transformation of protoplasts, and microinjection (Danieli et al Nat. Biotechnol 16:345-348, 1998; Staub et al Nat. Biotechnol 18: 333-338, 2000; O'Neill et al Plant J. 3:729-738, 1993; Knoblauch et al Nat. Biotechnol 17: 906-909; U.S. Pat. Nos. 5,451,513, 5,545,817, 5,545,818, and 5,576,198; in Intl. Application No. WO 95/16783; and in Boynton et al., Methods in Enzymology 217: 510-536 (1993), Svab et al., Proc. Natl. Acad. Sci. USA 90: 913-917 (1993), and McBride et al., Proc. Natl. Acad. Sci. USA 91: 7301-7305 (1994)). Any vector suitable for the methods of biolistic bombardment, polyethylene glycol transformation of protoplasts and microinjection will be suitable as a targeting vector for chloroplast transformation. Any double stranded DNA vector may be used as a transformation vector, especially when the method of introduction does not utilize *Agrobacterium*.

Plants which can be genetically modified include grains, forage crops, fruits, vegetables, oil seed crops, palms, forestry, and vines. Specific examples of plants which can be modified follow: maize, banana, peanut, field peas, sunflower, tomato, canola, tobacco, wheat, barley, oats, potato, soybeans, cotton, carnations, sorghum, lupin and rice.

The present disclosure provides transformed plant cells, tissues, plants and products that contain the transformed plant cells. A feature of the subject transformed cells, and tissues and products that include the same is the presence of a subject nucleic acid integrated into the genome, and production by plant cells of a CasJ polypeptide, or a CasJ fusion polypeptide, of the present disclosure.

Recombinant plant cells of the present invention are useful as populations of recombinant cells, or as a tissue, seed, whole plant, stem, fruit, leaf, root, flower, stem, tuber, grain, animal feed, a field of plants, and the like.

Nucleotide sequences encoding a CasJ polypeptide, or a CasJ fusion polypeptide, of the present disclosure can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters, inducible promoters, spatially restricted and/or temporally restricted promoters, etc.

Table of biological sequences and mutations referred to in the specification and claims

| Name | SEQ ID NO | Sequence |
|---|---|---|
| CasJ | 1 | MQQYQVSKTVRFGLTLKNSEKKHATHLLLKDLVNVSEERIKNEIT KDDKNQSELSFFNEVIETLDLMDKYIKDWENCFYRTDQIQLTKEYY KVIAKKACEDWFWTNDRGMKEPTSSIISENSLKSSDKSKTSDNLDR KKKILDYWKGNIFKTQKAIKDVLDITEDIQKAIEEKKSHREINRVNH RKMGIHLIHLINDTLVPLCNGSIFFGNISKLDFCESENEKLIDFASTE KQDERKFLLSKINEIKQYFEDNGGNVPFARATLNRHTANQKPDRY NEEIKKLVNELGVNSLVRSLKSKTIEEIKTHFEFENKNKINELKNSF VLSIVEKIQLFKYKTIPASVRELLADYFEEQKLSTKEEALTIFEEIGKP QNIGFDYIQLKEKDNFTLKKYPLKQAFDYAWENLARLDQNPKANQ FSVDECKRFFKEVF SMEMDNINFKTYALLLALKEKTTAFDKKGEG AAKNKSEIIEQIKGVFEELDQPFKIIANTLREEVIKKEDELNVLKRQY RETDRKIKTLQNEIKKIKNQIKNLENSKKYSFPEIIKWIDLTEQEQLL DKNKQAKSNYQKAKGDLGLIRGSQKTSINDYFYLTDKVYRKLAQ DFGKKMADLREKLLDKNDVNKIKYLSYIVKDNQGYQYTLLKPLE DKNAEIIELKSEPNGDLKLFEIKSLTSKTLNKFIKNKGAYKEFHSAEF EHKKIKEDWKNYKYNSDFIVKLKKCLSHSDMANTQNWKAFGWD LDKCKSYETIEKEIDQKSYQLVEIKLSKTTIEKWVKENNYLLLPIVN QDITAEKLKVNTNQFTKDWQHIFEKNPNHRLHPEFNIAYRQPTKDY AKEGEKRYSREQLTGQEMYEYIPQDANYISRKEQITLENDKEEQKI QVETENNQIAKILNAEDFYV<u>IGIDRGI</u>TQLATLCVLNKNGVIQGGFE IFTREFDYTNKQWKHTKLKENRNILDISNLKVETTVNGEKVLVDLS EVKTYLRDENGEPMKNEKGVILTKDNLQKIKLKQLAYDRKLQYK MQHEPELVLSELDRLENKEQIPNLLASTKLISAYKEGTAYADIDIEQ FWNILQTFQTIVDKEGGIENAKKTMEFRQYTELDASFDLKNGVVA NMVGVVKFIMEKYNYKTF<u>IALEDL</u>TFAFGQSIDGINGERLRSTKED KEVDFKEQENSTLAGLGTYHFFEMQLLKKLSKTQIGNEIKHFVPAF RSTENYEKIVRKDKNVKAKIVSYPEGIVSFVNPRNTSISCPNCKNAN KSNRIKKENDRILCKHNIEKTKGNCGFDTANFDENKLRAENKGKN FKYI<u>SSGDANAA</u>YNIAVKLLEDKIFEINKK |
| Direct repeat (DR; residues 19-36 underlined) | 2 | GTTTAAAAAACCTTTAAA<u>ATTTCTACTATTGTAGAT</u> |
| CTP 1 | 3 | MASMISSSAVTTVSRASRGQSAAMAPFGGLKSMTGFPVRKVNTDI TSITSNGGRVKCMQVWPPIGKKKFETLSYLPPLTRDSRA |
| CTP 2 | 4 | MASMISSSAVTTVSRASRGQSAAMAPFGGLKSMTGFPVRKVNTDI TSITSNGGRVKS |
| CTP 3 | 5 | MASSMLSSATMVASPAQATMVAPFNGLKSSAAFPATRKANNDITS ITSNGGRVNCMQVWPPIEKKKFETLSYLPDLTDSGGRVNC |
| CTP 4 | 6 | MAQVSRICNGVQNPSLISNLSKSSQRKSPLSVSLKTQQHPRAYPISS SWGLKKSGMTLIGSELRPLKVMSSVSTAC |

-continued

| Name | SEQ ID NO | Sequence |
|---|---|---|
| CTP 5 | 7 | MAQVSRICNGVWNPSLISNLSKSSQRKSPLSVSLKTQQHPRAYPISS SWGLKKSGMTLIGSELRPLKVMSSVSTAC |
| CTP 6 | 8 | MAQINNMAQGIQTLNPNSNFHKPQVPKSSSFLVFGSKKLKNSANS MLVLKKDSIFMQLFCSFRISASVATAC |
| CTP 7 | 9 | MAALVTSQLATSGTVLSVTDRFRRPGFQGLRPRNPADAALGMRTV GASAAPKQSRKPHRFDRRCLSMVV |
| CTP 8 | 10 | MAALTTSQLATSATGFGIADRSAPSSLLRHGFQGLKPRSPAGGDAT SLSVTTSARATPKQQRSVQ RGSRRFPSVVVC |
| CTP 9 | 11 | MASSVLSSAAVATRSNVAQANMVAPFTGLKSAASFPVSRKQNLDI TSIASNGGRVQC |
| CTP 10 | 12 | MESLAATSVFAPSRVAVPAARALVRAGTVVPTRRTSSTSGTSGVK CSAAVTPQASPVISRSAAAA |
| CTP 11 | 13 | MGAAATSMQSLKFSNRLVPPSRRLSPVPNNVTCNNLPKSAAPVRT VKCCASSWNSTINGAAATTNGASAASS |
| CasJ tracrRNA 1 of the CasJ locus | 14 | AGUUACUAUUGUAACAAUUGCAAACCUAGGUCUUAAUAUUCU AUAAUAUGACAAAAAGCAUAAAAACAAGCCAAGAAGCAUUGU UUUUU |
| Residues 19-36 of SEQ ID NO: 2 | 15 | ATTTCTACTATTGTAGAT |
| EEP 1 | 16 | GLFXALLXLLXSLWXLLLXA wherein each X is independently selected from lysine, histidine, and arginine |
| EEP 2 | 17 | GLFHALLHLLHSLWHLLLHA |
| NLS 3 | 18 | KRPAATKKAGQAKKKK |
| NLS 4 | 19 | PAAKRVKLD |
| NLS 5 | 20 | RQRRNELKRSP |
| NLS 6 | 21 | NQSSNFGPMKGGNFGGRSSGPYGGGGQYFAKPRNQGGY |
| NLS 7 | 22 | RMRIZFKNKGKDTAELRRRRVEVSVELRKAKKDEQILKRRNV |
| NLS 8 | 23 | VSRKRPRP |
| NLS 9 | 24 | PPKKARED |
| NLS 10 | 25 | PQPKKKPL |
| NLS 11 | 26 | SALIKKKKKMAP |
| NLS 12 | 27 | DRLRR |
| NLS 13 | 28 | PKQKKRK |
| NLS 14 | 29 | RKLKKKIKKL |
| NLS 15 | 30 | REKKKFLKRR |
| NLS 16 | 31 | KRKGDEVDGVDEVAKKKSKK |
| NLS 17 | 32 | RKCLQAGMNLEARKTKK |
| PTD 1 | 33 | YGRKKRRQRRR |
| PTD 2 | 34 | RRQRRTSKLMKR |
| PTD 3 | 35 | GWTLNSAGYLLGKINLKALAALAKKIL |
| PTD 4 | 36 | KALAWEAKLAKALAKALAKHLAKALAKALKCEA |
| PTD 5 | 37 | RQIKIWFQNRRMKWKK |

-continued

| Name | SEQ ID NO | Sequence |
|---|---|---|
| PTD 6 | 38 | YGRKKRRQRRR |
| PTD 7 | 39 | RKKRRQRRR |
| PTD 8 | 40 | YGRKKRRQRRR |
| PTD 9 | 41 | RKKRRQRR |
| PTD 10 | 42 | YARAAARQARA |
| PTD 11 | 43 | THRLPRRRRRR |
| PTD 12 | 44 | GGRRARRRRRR |
| Linker 1 | 45 | GSGGS$_n$, where n is an integer of at least one |
| Linker 2 | 46 | GGSGGS$_n$, where n is an integer of at least one |
| Linker 3 | 47 | GGGS$_n$, where n is an integer of at least one |
| Linker 4 | 48 | GGSG |
| Linker 5 | 49 | GGSGG |
| Linker 6 | 50 | GSGSG |
| Linker 7 | 51 | GSGGG |
| Linker 8 | 52 | GGGSG |
| Linker 9 | 53 | GSSSG |
| RuvCI | 54 | IGIDRGI |
| RuvCII | 55 | IALEDL |
| RuvCIII | 56 | SSGDANAA |
| NLS1 | 57 | PKKKRKV |
| penetratin | 58 | RQIKIWFQNRRMKWKK |
| CasJ tracrRNA 2 RNA sequence | 59 | UUUUAUGCUUUUUGUCAUAUUAUAGAAUAUUAAGACCUAGGU UUGCAAUUGUUACAAUAGUAACUUUUUU |
| FIG. 3 Activator RNA | 60 | AAUUUCUACUAUUGUAGAU |
| dCasJ mutations (comprise or correspond to position in SEQ ID NO: 1) | | D901A; E1128A; D1298A |
| Enhanced CasJ mutations (comprise or correspond to position in SEQ ID NO: 1) | | K356F, L593N, D604K, K1113A, K1122N, D1139F or D1139Q, T1185L, S1200L, Y1221K, and L1309G |

-continued

| Name | SEQ ID NO | Sequence |
|---|---|---|
| Enhanced CR CasJ Mutations (comprise or correspond to position in SEQ ID NO: 1) | | E834I |

EXAMPLES

The following examples are not intended to limit the scope of what the inventors regard as their invention.

Example 1—Nuclease Effector Sequence

Sequence data from samples of microbial communities is analyzed to identify new Class 2 CRISPR-Cas systems. Candidate sequences are proposed based on proximity to CRISPR arrays and the presence of conserved sequence domains.

A nuclease sequence now termed CasJ is shown in SEQ ID NO: 1. CasJ contains a RuvC split domain in the C-terminal region (RuvC-I (SEQ ID NO: 54), RuvC-II (SEQ ID NO: 55), and RuvC-III (SEQ ID NO: 56)).

Example 2—crRNA

A CRISPR array adjacent to the nuclease of Example 1 points functional RNA components. The direct repeat (DR) sequences flanking many spacer sequences about 22 residues long of the CRISPR array are shown in SEQ ID NO: 2.

Example 3—Single Guide Sequence

A vector is made having an Arabidopsis U6 (Pol III) promoter driving expression of an RNA made up of the RNA encoded by the SEQ ID NO: 15 sequence fused to a 22 residue guide RNA directed to the Phytoene desaturase (PDS) gene of soybean.

Example 4—CasJ

An effector nuclease vector is made by making a vector having a 35S promoter operably linked to drive expression of a soybean codon-optimized mRNA encoding an amino acid sequence of CasJ flanked at both the N and C termini by nuclear localization sequences.

Example 5—Genome Editing

The vectors of examples 3 and 4 are co-transformed into a soybean plant. Transformed plants are regenerated, and the albino phenotype of PDS mutants is observed. The PDS genomic sequence of plants material with albino phenotype is sequenced. Mutations in the PDS gene are found.

Although the foregoing invention has been described in some detail by way of illustration and example for purposes of clarity of understanding, it will be obvious that certain changes and modifications may be practiced within the scope of the appended claims.

What is claimed is:

1. A composition comprising:
   a) a CasJ fusion polypeptide comprising a heterologous polypeptide fused to an amino acid sequence having 80% or more identity to the amino acid sequence set forth in SEQ ID NO: 1, or a nucleic acid molecule encoding the CasJ fusion polypeptide; and
   b) a CasJ guide RNA, or one or more DNA molecules encoding the CasJ guide RNA.

2. The composition of claim 1, wherein the CasJ guide RNA is a single guide RNA.

3. The composition of claim 1, wherein the CasJ guide RNA comprises an RNA encoded by SEQ ID NO:15.

4. The composition of claim 1, wherein the composition comprises a lipid or is within a liposome.

5. The composition of claim 1, wherein the CasJ fusion polypeptide and the CasJ guide RNA are within and/or at least partially coat a particle.

6. The composition of claim 1, wherein the composition further comprises one or more of: a buffer, a nuclease inhibitor, and a protease inhibitor.

7. A composition comprising:
   a) a CasJ polypeptide comprising an amino acid sequence having at least 80% but less than 100% identity to the amino acid sequence of SEQ ID NO: 1, or a nucleic acid molecule encoding the CasJ polypeptide, wherein the CasJ polypeptide is a catalytically inactive CasJ Polypeptide (dCasJ) and
   b) a CasJ guide RNA, or one or more DNA molecules encoding the CasJ guide RNA.

8. The composition of claim 7, wherein the CasJ polypeptide comprises one or more mutations at a position corresponding to those selected from D901, E1128, and/or D1298 of SEQ ID NO: 1.

9. The composition of claim 1, further comprising a DNA donor template.

10. A CasJ fusion polypeptide comprising a heterologous polypeptide fused to a CasJ polypeptide comprising an amino acid sequence having 80% or more identity to the amino acid sequence set forth in SEQ ID NO: 1.

11. The CasJ fusion polypeptide of claim 10, wherein the CasJ polypeptide is a catalytically inactive CasJ Polypeptide (dCasJ).

12. The CasJ fusion polypeptide of claim 11, wherein the CasJ polypeptide comprises one or more mutations selected from D901A, E1128A, and/or D1298A by reference to SEQ ID NO: 1.

13. The CasJ fusion polypeptide of claim 10, wherein the heterologous polypeptide is operably linked to the N-terminus and/or the C-terminus of the CasJ polypeptide.

14. The CasJ fusion polypeptide of claim 10, wherein the heterologous polypeptide comprises a comprising a nuclear localization signal (NLS), and endosomal escape peptide, and/or a chloroplast transit peptide.

15. The CasJ fusion polypeptide of claim 10, wherein the heterologous polypeptide exhibits an enzymatic activity that modifies target DNA.

16. The CasJ fusion polypeptide of claim 15, wherein the heterologous polypeptide exhibits one or more enzymatic activities selected from: nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity, and/or glycosylase activity.

17. The CasJ fusion polypeptide of claim 14, wherein the chloroplast transit peptide comprises an amino acid sequence selected from the group consisting of SEQ ID NO:3-12, and 13.

18. The CasJ fusion polypeptide of claim 11, wherein the heterologous polypeptide protein increases or decreases transcription of a gene when the CasJ fusion polypeptide is bound to the gene and a guide RNA in comparison to when the CasJ fusion polypeptide is not bound to the gene and a guide RNA.

19. The CasJ fusion polypeptide of claim 18, wherein the heterologous polypeptide is a transcriptional repressor domain.

20. The CasJ fusion polypeptide of claim 18, wherein the heterologous polypeptide is a transcriptional activation domain.

* * * * *